US009623088B2

(12) United States Patent
Maloney et al.

(10) Patent No.: US 9,623,088 B2
(45) Date of Patent: Apr. 18, 2017

(54) FACTOR VIII POLYPEPTIDE FORMULATIONS

(71) Applicant: Bioverativ Therapeutics Inc., Waltham, MA (US)

(72) Inventors: Kevin Maloney, Cambridge, MA (US); Daniel Gage, Cambridge, MA (US); Ahmad Abdul-Fattah, Cambridge, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 246 days.

(21) Appl. No.: 14/213,180

(22) Filed: Mar. 14, 2014

(65) Prior Publication Data

US 2014/0308280 A1     Oct. 16, 2014

Related U.S. Application Data

(60) Provisional application No. 61/800,293, filed on Mar. 15, 2013, provisional application No. 61/817,085, filed on Apr. 29, 2013, provisional application No. 61/829,884, filed on May 31, 2013, provisional application No. 61/839,477, filed on Jun. 26, 2013, provisional application No. 61/863,860, filed on Aug. 8, 2013, provisional application No. 61/876,927, filed on Sep. 12, 2013, provisional application No. 61/879,955, filed on Sep. 19, 2013, provisional application No. 61/897,742, filed on Oct. 30, 2013.

(51) Int. Cl.
*A61K 38/37* (2006.01)
*C07K 14/755* (2006.01)
*C07K 16/28* (2006.01)

(52) U.S. Cl.
CPC ............ *A61K 38/37* (2013.01); *C07K 14/755* (2013.01); *C07K 16/2833* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,757,006 A | 7/1988 | Toole, Jr. et al. |
| 4,868,112 A | 9/1989 | Toole, Jr. |
| 4,965,199 A | 10/1990 | Capon et al. |
| 4,994,371 A | 2/1991 | Davie et al. |
| 5,004,803 A | 4/1991 | Kaufman et al. |
| 5,112,950 A | 5/1992 | Meulien et al. |
| 5,171,844 A | 12/1992 | van Ooyen et al. |
| 5,364,771 A | 11/1994 | Lollar et al. |
| 5,543,502 A | 8/1996 | Nordfang et al. |
| 5,595,886 A | 1/1997 | Chapman et al. |
| 5,610,278 A | 3/1997 | Nordfang et al. |
| 5,712,122 A | 1/1998 | Boime et al. |
| 5,733,873 A * | 3/1998 | Osterberg ............ A61K 9/0019 514/13.7 |
| 5,789,203 A | 8/1998 | Chapman et al. |
| 5,859,204 A | 1/1999 | Lollar |
| 5,972,885 A | 10/1999 | Spira et al. |
| 6,048,720 A | 4/2000 | Dalborg et al. |
| 6,060,447 A | 5/2000 | Chapman et al. |
| 6,228,620 B1 | 5/2001 | Chapman et al. |
| 6,251,632 B1 | 6/2001 | Lillicrap et al. |
| 6,316,226 B1 | 11/2001 | Van Ooyen et al. |
| 6,346,513 B1 | 2/2002 | Van Ooyen et al. |
| 6,376,463 B1 | 4/2002 | Lollar |
| 6,458,563 B1 | 10/2002 | Lollar |
| 6,686,179 B2 | 2/2004 | Fleer et al. |
| 7,041,635 B2 | 5/2006 | Kim et al. |
| 7,348,004 B2 | 3/2008 | Peters et al. |
| 7,404,956 B2 | 7/2008 | Peters et al. |
| 7,592,010 B2 | 9/2009 | Rosen et al. |
| 7,632,921 B2 | 12/2009 | Pan et al. |
| 2005/0100990 A1 | 5/2005 | Saenko et al. |
| 2009/0087411 A1 | 4/2009 | Fares et al. |
| 2009/0163699 A1 | 6/2009 | Chamberlain et al. |
| 2009/0264627 A1 | 10/2009 | Gillies et al. |
| 2010/0286067 A1 | 11/2010 | Defrees |
| 2010/0292130 A1 | 11/2010 | Skerra et al. |
| 2012/0093840 A1 | 4/2012 | Oestergaard et al. |

FOREIGN PATENT DOCUMENTS

| | | | |
|---|---|---|---|
| DE | WO 2008077616 A1 * | 7/2008 | ........... C07K 14/745 |
| EP | 0154316 A2 | 9/1985 | |
| EP | 0295597 A2 | 12/1988 | |
| EP | 0401384 A1 | 12/1990 | |
| EP | 2173890 B1 | 3/2011 | |
| WO | WO-8704187 A1 | 7/1987 | |
| WO | WO-8800831 A1 | 2/1988 | |
| WO | WO-8803558 A1 | 5/1988 | |
| WO | WO-8808035 A1 | 10/1988 | |
| WO | WO-9109122 A1 | 6/1991 | |
| WO | WO-9216221 A1 | 10/1992 | |
| WO | WO-9320093 A1 | 10/1993 | |
| WO | WO-9407510 A1 | 4/1994 | |
| WO | WO-9411503 A2 | 5/1994 | |
| WO | WO-9526750 A1 | 10/1995 | |

(Continued)

OTHER PUBLICATIONS

Armour, K.L., et al., "Recombinant human IgG molecules lacking Fcgamma receptor I binding and monocyte triggering activities," European Journal of Immunology 29(8):2613-2624, Wiley-VCH Verlag GmbH, Germany (1999).

(Continued)

*Primary Examiner* — Michael Szperka
(74) *Attorney, Agent, or Firm* — Sterne, Kessler, Goldstein & Fox P.L.L.C.

(57) ABSTRACT

The present invention provides a formulation of a Factor VIII polypeptide, e.g., FVIII-Fc, and methods of using the same. The FVIII polypeptide can be a recombinant FVIII protein, a short-acting FVIII protein, or a long-acting FVIII protein. The pharmaceutical formulation comprising a FVIII polypeptide can be used for individual prophylaxis, weekly prophylaxis, episodic (on-demand) treatment, or perioperative management of hemophilia.

35 Claims, 2 Drawing Sheets

(56) References Cited

FOREIGN PATENT DOCUMENTS

| WO | WO-9534326 A1 | 12/1995 | | |
|---|---|---|---|---|
| WO | WO-0048635 A1 | 8/2000 | | |
| WO | WO-2004101740 A2 | 11/2004 | | |
| WO | WO-2005058283 A2 | 6/2005 | | |
| WO | WO-2006074199 A1 | 7/2006 | | |
| WO | WO 2007092772 A2 | * | 8/2007 | ....... A61K 39/39591 |
| WO | WO-2007092772 A2 | | 8/2007 | |
| WO | WO-2008077616 A1 | 7/2008 | | |
| WO | WO-2008155134 A1 | 12/2008 | | |
| WO | WO-2010115866 A1 | 10/2010 | | |
| WO | WO-2011069164 A2 | 6/2011 | | |
| WO | WO 2011069164 A2 | * | 6/2011 | ............ A61K 38/37 |
| WO | WO-2013009627 A2 | 1/2013 | | |
| WO | WO-2013057219 A1 | 4/2013 | | |
| WO | WO-2014026954 A1 | 2/2014 | | |

OTHER PUBLICATIONS

Bai, Y., et al., "Recombinant granulocyte colony-stimulating factor-transferrin fusion protein as an oral myelopoietic agent," Proceedings of the National Academy of Sciences USA 102(20):7292-7296, National Academy of Sciences, United States (2005).

Brandsma, M,E., et al., "Recombinant human transferrin: beyond iron binding and transport," Biotechnology Advances 29(2):230-238, Elsevier, United States (2011).

Brutlag, D.L., et al., "Improved sensitivity of biological sequence database searches," Computer Applications in the Biosciences 6(3):237-245, Oxford University Press, England (1990).

Burmeister, W.P., et al., "Crystal structure of the complex of rat neonatal Fc receptor with Fc," Nature 372(6504):379-383, Nature Publishing Group, UK (1994).

Cameron, C., et al., "The canine factor VIII cDNA and 5' flanking sequence," Journal of Thrombosis and Haemostasis 79(2):317-322, International Society on Thrombosis and Haemostasis, UK (1998).

Cutler, J.A., et al., "The identification and classification of 41 novel mutations in the factor VIII gene (F8C)," Human Mutation 19(3):274-278, John Wiley & Sons, UK (2002).

Dennis, M., et al., "Albumin Binding as a General Strategy for Improving the Pharmacokinetics of Proteins," The Journal of Biological Chemistry 277(38):35035-35043, The American Society for Biochemistry and Molecular Biology, Inc., United States (2002).

Dobeli, H., et al., "Role of the carboxy-terminal sequence on the biological activity of human interferon (IFN-y)," Journal of Biotechnology 7:199-216, Elsevier, Netherlands (1988).

Eaton, D.L., et al., "Construction and characterization of an active factor VIII variant lacking the central one-third of the molecule," Biochemistry 25(26):8343-8347, The American Chemical Society, United States (1986).

Fatouros, A., et al., "Recombinant factor VIII SQ—influence of oxygen, metal ions, pH and ionic strength on its stability in aqueous solution," International Journal of Pharmaceutics 155(1):121-131, Elsevier, United States (1997).

Francis, G.E., "Protein Modification and Fusion Proteins," Focus on Growth Factors 3(2):4-10, Mediscript, England (1992).

Friend, P.J., et al., "Phase I study of an engineered aglycosylated humanized CD3 antibody in renal transplant rejection," Transplantation 68(11):1632-1637, Lippincott Wilkins, Inc., United States (1999).

Gayle, R.B. III., et al., "Identification of Regions in Interleukin-1alpha Important for Activity," The Journal of Biological Chemistry 268(29):22105-22111, The American Society for Biochemistry and Molecular Biology, Inc., United States (1993).

GenBank, "*Homo sapiens* transferrin (TF), mRNA", Accession No. NM001063.1, accessed at http://www.ncbi.nlm.nih.gov/nuccore/NM_001063, May 25, 2014, 5 pages.

GenBank, "*Homo sapiens* transferrin (TF), mRNA," Accession No. XM002793 accessed at https://www.ncbi.nlm.nih.gov/nuccore/XM_002793.7?report=genbank, May 13, 2002, 2 pages.

GenBank, "*Homo sapiens* transferrin (TF), mRNA," Accession No. XM039845 accessed at https://www.ncbi.nlm.nih.gov/nuccore/XM_039845.1?report=genbank, Jul. 16, 2001, 2 pages.

GenBank, "*Homo sapiens* transferrin (TF), mRNA," Accession No. XM039847 accessed at http://www.ncbi.nlm.nih.gov/nuccore/XM_039847.1?report=genbank, Jul. 16, 2001, 2 pages.

GenBank, "Human transferrin mRNA, complete cds", Accession No. M12530.1, accessed at http://www.ncbi.nlm.nih.gov/nuccore/M1253014, Jan. 14, 1995, 2 pages.

GenBank, "Transferrin [human, liver, mRNA, 2347 nt]", Accession No. S95936.1, accessed at http://www.ncbi.nlm.nih.gov/nuccore/S95936, May 7, 1993, 2 pages.

Gitschier, J., et al., "Characterization of the human factor VIII gene," Nature 312(5992):326-330, Nature Publishing Group, UK (1984).

Healey, J.F., et al., "The cDNA and derived amino acid sequence of porcine factor VIII," Blood 88(11):4209-4214, The American Society of Hematology, United States of America (1996).

Hoeben, R.C., et al., "Expression of functional factor VIII in primary human skin fibroblasts after retrovirus-mediated gene transfer," The Journal of Biological Chemistry 265(13):7318-7323, The American Society for Biochemistry and Molecular Biology, Inc., United States (1990).

Holt, L.J., et al., "Anti-serum albumin domain antibodies for extending the half-lives of short lived drugs," Protein Engineering, Design and Selection 21(5):283-288, Oxford University Press, United Kingdom, (2008).

International Search Report and Written Opinion of the International Searching Authority for Application No. PCT/US2014/029354, European Patent Office, Netherlands, mailed on Aug. 7, 2014, 16 pages.

Kim, B.J., et al., "Transferrin fusion technology: a novel approach to prolonging biological half-life of insulinotropic peptides," The Journal of Pharmacology and Experimental Therapeutics 334(3):682-692, American Society for Pharmacology and Experimental Therapeutics, United States (2010).

Kraulis, P.J., et al., "The serum albumin-binding domain of streptococcal protein G is a three-helical bundle: a heteronuclear NMR study," FEBS Letters 378(2):190-194, Federation of American Societies for Experimental Biology, United States (1996).

Langner, K.D., et al., "Synthesis of biologically active deletion mutants of human factor VIII:C," Behring Institute Mitteilungen 82:16-25, Behringwerke AG, Germany, (1988).

Li, H., et al., "The role of the transferrin-transferrin-receptor system in drug delivery and targeting," Trends in Pharmacological Sciences 23(5):206-209, Elsevier, England (2002).

Linhult, M., et al., "Mutational analysis of the interaction between albumin-binding domain from streptococcal protein G and human serum albumin," Protein Science 11(2):206-213, Wiley-Blackwell, United States (2002).

Lollar, P., et al., "Coagulant Properties of Hybrid Human/Porcine Factor VIII Molecules," Journal of Biological Chemistry 267(33):23652-23657, The American Society for Biochemistry and Molecular Biology, Inc., United States (1992).

Lollar, P., et al., "Structural Basis for the Decreased Procoagulant Activity of Human Factor VIII Compared to the Porcine Homolog," Journal of Biological Chemistry 266(19):12481-12486, The American Society for Biochemistry and Molecular Biology, Inc., United States (1991).

Mahlangu, J., et al., "Phase 3 study of recombinant factor VIII Fc fusion protein in severe hemophilia A," Blood 123(3):317-325, The American Society of Hematology, United States (Jan. 16, 2014).

Malik, F., et al., "Polyethylene Glycol (PEG)-Modified Granulocyte-Macrophage Colony-Stimulating Factor (GM-CSF) With Conserved Biological Activity," Experimental Hematology 20(8):1028-1035, International Society for Experimental Hematology, United States (1992).

Mannucci, P.M., et al., "The hemophilias—from royal genes to gene therapy," The New England Journal of Medicine 344(23):1773-1779, Massachusetts Medical Society, United States (2001).

Mei, B., et al., "Expression of Human Coagulation Factor VIII in a Human Hybrid Cell Line, HKB11," Biotechnology 34(2):165-178, Humana Press Inc., United States (2006).

(56) References Cited

OTHER PUBLICATIONS

Mei, B., et al., "Rational Design of a Fully Active, Long-Acting PEGylated Factor VIII for Hemophilia A Treatment," Blood 116(2):270-279, The American Society of Hematology, United States (2010).
Meulien, P., et al., "A new recombinant procoagulant protein derived from the cDNA encoding human factor VIII," Protein Engineering 2(4):301-306, IRL Press Ltd, England (1988).
Muller, D., et al., "Recombinant bispecific antibodies for cellular cancer immunotherapy," Current opinion in molecular therapeutics 9(4):319-326, Current Drugs Ltd., UK (2007).
Neumann, E., et al., "Gene Transfer into Mouse Lyoma Cells by Electroporation in High Electric Fields," EMBO J 1(7):841-845, IRL Press Ltd, England (1982).
Oganesyan, V., et al., "Structural characterization of a human Fc fragment engineered for extended serum half-life," Molecular Immunology 46(8-9):1750-1755, Elsevier, United States (2009).
Peyvandi, F., et al., "Genetic Diagnosis of Haemophilia and Other Inherited Bleeding Disorders," Haemophilia 12(Suppl 3):82-89, Blackwell Publishing Ltd., England (2006).
Powell, J.S., et al., "Safety and prolonged activity of recombinant factor VIII Fc fusion protein in hemophilia a patients," Blood 119(13):3031-3037, The American Society of Hematology, United States (2012).
Rodriguez-Merchan, E.C., "Management of musculoskeletal complications of hemophilia," Seminars in Thrombosis and Hemostasis 29(1):87-96, Thieme Medical Publishers, Inc., United States (2003).
Ron, D., et al., "Expression of biologically active recombinant keratinocyte growth factor: Structure/function analysis of amino-terminal truncation mutants," The Journal of Biological Chemistry 268(4):2984-2988, American Society for Biochemistry and Molecular Biology, United States (1993).
Roovers, R.C., et al., "Efficient inhibition of EGFR signaling and of tumour growth by antagonistic anti-EFGR Nanobodies," Cancer Immunology, Immunotherapy 56(3):303-317, Springer, United States (2007).
Routledge, E.G., et al., "The effect of aglycosylation on the immunogenicity of a humanized therapeutic CD3 monoclonal antibody," Transplantation 60(8):847-853, Williams & Wilkins, United States (1995).
Sarver, N., et al., "Stable expression of recombinant factor VIII molecules using a bovine papillomavirus vector," DNA 6(6):553-564, Mary Ann Liebert, Inc., United States (1987).
Schulte, S., "Half-life extension through albumin fusion technologies," Thrombosis Research 124(2):S6-S8, Elsevier, United States (2009).
Shields, R.L., et al., "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R," Journal of Biological Chemistry 276(9):6591-6604, The American Society for Biochemistry and Molecular Biology, Inc., United States (2001).
Story, C.M., et al., "A major histocompatibility complex class I-like Fc receptor cloned from human placenta: possible role in transfer of immunoglobulin G from mother to fetus," The Journal of Experimental Medicine 180(6):2377-2381, The Rockefeller University Press, United States (1994).
Toole, J.J., et al., "A large region (approximately equal to 95 kDa) of human factor VIII is dispensable for in vitro procoagulant activity," Proceedings of the National Academy of Sciences USA 83(16):5939-5942, National Academy of Sciences, United States (1986).
Toole, J.J., et al., "Molecular cloning of a cDNA encoding human antihaemophilic factor," Nature 312(5992):342-347, Nature Publishing Group, UK (1984).
Trussel, S., et al., "New strategy for the extension of the serum half-life of antibody fragments," Bioconjugate Chemistry 20(12):2286-2292, American Chemical Society, United States (2009).
Vaccaro, C., et al., "Engineering the Fc region of immunoglobulin G to modulate in vivo antibody levels," Nature Biotechnology 23(10):1283-1288, Nature Publishing Group, United States (2005).
Vehar, G.A., et al., "Structure of human factor VIII," Nature 312(5992):337-342, Nature Publishing Group, UK (1984).
Wakabayashi, H., et al., "Residues 110-126 in the A1 domain of factor VIII contain a Ca2+ binding site required for cofactor activity," The Journal of Biological Chemistry 279(13):12677-12684, The American Society for Biochemistry and Molecular Biology, Inc., United States (2004).
Wang, Y., et al., "Receptor-mediated activation of a proinsulin-transferrin fusion protein in hepatoma cells," The Journal of Controlled Release 155(3):386-392, Elsevier, Netherlands (2011).
Ward, E.S., et al., "The effector functions of immunoglobulins: implications for therapy," Therapeutic Immunology 2(2):77-94, Blackwell Science Ltd., England (1995).
Weidler, B., et al., "Pharmacokinetic parameters as criteria for clinical use of hydroxyethyl starch preparations," Arzneimittelforschung Drug Research 41(5):494-498, Thieme, Germany (1991).
Wigler, M., et al., "Biochemical Transfer of Single-Copy Eucaryotic Genes Using Total Cellular DNA as Donor," Cell 14(3):725-731, Cell Press, United States (1978).
Wood, W.I., et al., "Expression of active human factor VIII from recombinant DNA clones," Nature 312(5992):330-337, Nature Publishing Group, UK (1984).
Sommermeyer, V. K., et al., "Klinisch verwendete Hydroxyethylstarke: Physikalisch-chemische Charakterisierung," Krankenhauspharmazie 8(8):271-278, Stuttgart, Germany (1987).

* cited by examiner

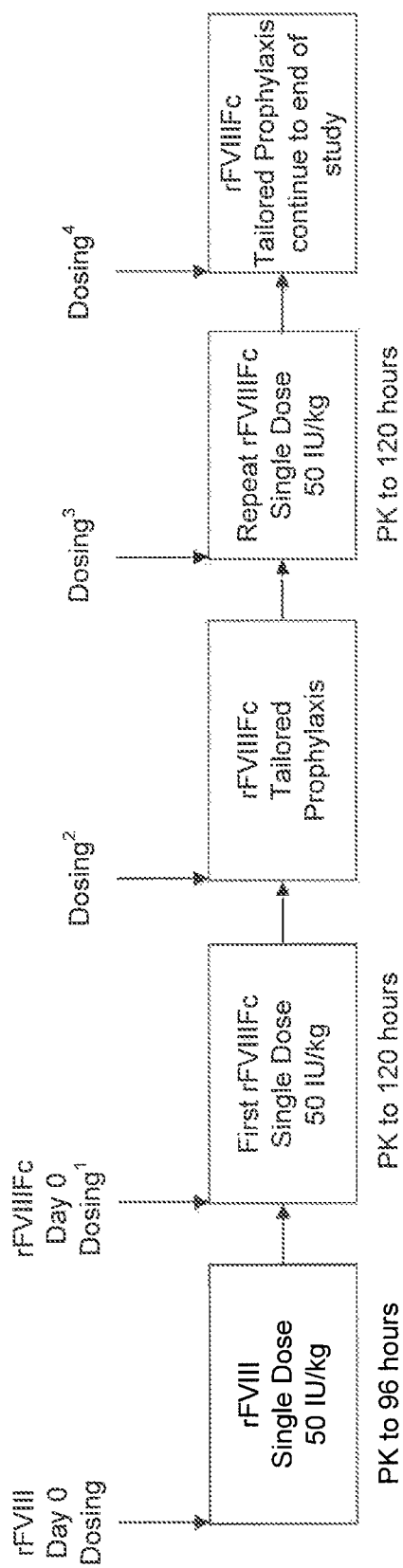

FIG. 1

1. Minimum interval of 96 hours, maximum interval of 8 weeks from rFVIII injection to first injection of 50 IU/kg rFVIIIFc for sequential PK profiling.
2. Starting regimen for twice weekly individualized (tailored) prophylaxis of 25 IU/kg on first day of week followed by 50 IU/kg on fourth day, with dose and interval adjusted to achieve target trough level of approximately 1% to 3% (or higher, as clinically indicated). FVIII level assessed at peak and trough.
3. Repeat dose of 50 IU/kg rFVIIIFc for sequential PK profiling administered at Week 14, or at 12 to 24 weeks after first injection of rFVIIIFc.
4. Continued individualized prophylaxis regimen until 28 (±2) weeks up to 52 (±2) weeks.

PK, pharmacokinetic

FACTOR VIII POLYPEPTIDE FORMULATIONS

REFERENCE TO RELATED APPLICATIONS

The present application claims the benefit of U.S. 61/800,293, filed Mar. 15, 2013, U.S. 61/817,085, filed Apr. 29, 2013, U.S. 61/829,884, filed May 31, 2013, U.S. 61/839,477, filed Jun. 26, 2013, U.S. 61/863,860, filed Aug. 8, 2013, U.S. 61/876,927, filed Sep. 12, 2013, U.S. 61/879,955, filed Sep. 19, 2013, and U.S. 61/897,742, filed Oct. 30, 2013, all of which are incorporated herein by reference in their entireties.

REFERENCE TO SEQUENCE LISTING SUBMITTED ELECTRONICALLY

The content of the electronically submitted sequence listing in ASCII text file (Name: 2159436000C_sequence_listing.txt; Size: 61,414 bytes; and Date of Creation: Mar. 14, 2014) is incorporated herein by reference in its entirety.

BACKGROUND OF THE INVENTION

Field of the Invention

The present invention relates generally to the field of therapeutics for hemostatic disorders.

Background Art

Hemophilia A is an X-linked bleeding disorder caused by mutations and/or deletions in the factor VIII (FVIII) gene resulting in a deficiency of FVIII activity (Peyvandi, F. et al. *Haemophilia* 12:82-89 (2006). The disease is characterized by spontaneous hemorrhage and excessive bleeding after trauma. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., *Semin. Thromb. Hemost.* 29:87-96 (2003), which is herein incorporated by reference in its entirety).

The A2 domain is necessary for the procoagulant activity of the factor VIII molecule. Studies show that porcine factor VIII has six-fold greater procoagulant activity than human factor VIII (Lollar, P., and E. T. Parker, *J. Biol. Chem.* 266:12481-12486 (1991)), and that the difference in coagulant activity between human and porcine factor VIII appears to be based on a difference in amino acid sequence between one or more residues in the human and porcine A2 domains (Lollar, P., et al., *J. Biol. Chem.* 267:23652-23657 (1992)), incorporated herein by reference in its entirety.

Treatment of hemophilia A is by replacement therapy targeting restoration of FVIII activity to 1 to 5% of normal levels to prevent spontaneous bleeding (Mannucci, P. M., et al., *N. Engl. J. Med.* 344:1773-1779 (2001), which is herein incorporated by reference in its entirety). There are plasma-derived and recombinant FVIII products available to treat bleeding episodes on-demand or to prevent bleeding episodes from occurring by treating prophylactically.

Reduced mortality, prevention of joint damage, and improved quality of life have been important achievements due to the development of plasma-derived and recombinant FVIII. Prolonged protection from bleeding would represent another key advancement in the treatment of hemophilia A patients.

BRIEF SUMMARY OF THE INVENTION

The present invention comprises a pharmaceutical composition comprising: (a) a FVIII polypeptide; (b) one or more stabilizing agents selected from sucrose, trehalose, raffinose, arginine, or mixture thereof; (c) sodium chloride (NaCl); (d) L-histidine; (e) calcium chloride; and (f) polysorbate 20 or polysorbate 80. In one embodiment, mannitol, glycine, alanine, or hydroxyethyl starch is not included in the pharmaceutical composition. In another embodiment, NaCl is the only bulking agent. In other embodiments, the FVIII polypeptide is a long-acting polypeptide or a short-acting polypeptide.

In other embodiments, the pharmaceutical composition comprises about 1% (w/v) to about 2.5% (w/v) sucrose, about 1.3% (w/v) sucrose to about 2.0% (w/v) sucrose, about 1.33% (w/v) sucrose or about 2.0% (w/v) sucrose, about 10 mg/ml to about 25 mg/ml sucrose, about 13 mg/ml to about 20 mg/ml sucrose, about 13.3 mg/ml sucrose, or about 20.0 mg/ml sucrose. In still other embodiments, the pharmaceutical composition comprises about 150 mM to about 250 mM NaCl, about 175 mM to about 225 mM NaCl, about 200 mM to about 210 mM NaCl, about 205 mM NaCl, about 8.8 mg/ml to about 14.6 mg/ml NaCl, about 10 mg/ml to about 13 mg/ml NaCl, about 12.0 mg/ml NaCl, about 250 mM to about 350 mM NaCl, about 275 mM to about 325 mM NaCl, about 308 mM NaCl, about 14.6 mg/ml to about 20.5 mg/ml NaCl, about 16 mg/ml to about 19 mg/ml NaCl, or about 18.0 mg/ml NaCl.

In yet other embodiments, the pharmaceutical composition comprises about 5 mM to about 15 mM L-histidine, about 6.64 mM L-histidine to about 9.8 mM L-histidine, about 0.75 mg/ml to about 2.25 mg/ml L-histidine, or about 1.03 mg/ml L-histidine to about 1.55 mg/ml L-histidine. In certain embodiments, the pharmaceutical composition comprises about 5 mM to about 10 mM calcium chloride, about 5.4 mM calcium chloride to about 8 mM calcium chloride, about 0.75 mg/ml to about 1.5 mg/ml calcium chloride dihydrate, or about 0.8 mg/ml calcium chloride dihydrate to about 1.18 mg/ml calcium chloride dihydrate.

In some embodiments, the pharmaceutical composition comprises about 0.008% (w/v) to about 0.025% (w/v) polysorbate 20 or polysorbate 80, about 0.013% (w/v) polysorbate 20 or polysorbate 80 or about 0.02% (w/v) polysorbate 20 or polysorbate 80, about 0.08 mg/ml to about 0.25 mg/ml polysorbate 20 or polysorbate 80, about 0.13 mg/ml polysorbate 20 or polysorbate 80 or about 0.20 mg/ml polysorbate 20 or polysorbate 80.

In other embodiments, the pharmaceutical composition comprises the rFVIIIFc polypeptide, which comprises a first subunit comprising an amino acid sequence at least 90% or 95% identical to amino acids 20 to 1684 of SEQ ID NO:2 or 20 to 2578 of SEQ ID NO:6, and a second subunit comprising an amino acid sequence at least 90% to 95% identical to amino acids 21 to 247 of SEQ ID NO:4. In certain embodiments, wherein the rFVIIIFc polypeptide comprises a first subunit comprising amino acids 20 to 1684 of SEQ ID NO:2 or 20 to 2578 of SEQ ID NO:6, and a second subunit comprising amino acids 21 to 247 of SEQ ID NO:4.

In certain embodiments, a FVIII polypeptide is present in a pharmaceutical composition at a concentration of about 50 IU/ml to about 2500 IU/ml, e.g., 83 IU/ml, 167 IU/ml, 250 IU/ml, 333 IU/ml, 500 IU/ml, 667 IU/ml, 1000 IU/ml, 1333 IU/ml, 1667 IU/ml, or 2000 IU/ml of the FVIII polypeptide. In some embodiments, a FVIII polypeptide is present in a pharmaceutical composition at a concentration of about 100 IU/ml to about 4000 IU/ml, e.g., 150 IU/ml, 287.5 IU/ml, 431.25 IU/ml, 575 IU/ml, 862.5 IU/ml, 1150 IU/ml, 1725 IU/ml, 2300 IU/ml, 2875 IU/ml, or 3450 IU/ml of the FVIII polypeptide.

In other embodiments, a pharmaceutical composition comprises: (a) about 50 IU/ml to about 2500 IU/ml of a long-acting FVIII polypeptide; (b) about 1% (w/v) to about 2.5% (w/v) of sucrose; (c) about 150 mM to about 250 mM NaCl; (d) about 5 mM to about 15 mM L-histidine; (e) about 5 mM to about 10 mM calcium chloride; and (f) about 0.008% (w/v) to about 0.025% of polysorbate 20 or polysorbate 80. In other embodiments, the pharmaceutical composition comprises about 175 mM to about 225 mM NaCl or about 200 mM to about 210 mM NaCl.

In yet other embodiments, a pharmaceutical composition comprises (a) about 83 IU/ml, about 167 IU/ml, about 250 IU/ml, about 333 IU/ml, about 500 IU/ml, about 667 IU/ml, about 1000 IU/ml, about 1333 IU/ml, about 1667 IU/ml, or about 2000 IU/ml of a FVIII polypeptide; (b) about 1.33% (w/v) of sucrose; (c) about 205 mM NaCl; (d) about 6.64 mM L-histidine; (e) about 5.4 mM calcium chloride; and (1) about 0.013% (w/v) of polysorbate 20 or polysorbate 80.

In some embodiments, a pharmaceutical composition comprises: (a) about 100 IU/ml to about 4000 IU/ml of a FVIII polypeptide; (b) about 1% (w/v) to about 2.5% (w/v) of sucrose; (c) about 250 mM to about 350 mM NaCl; (d) about 5 mM to about 15 mM L-histidine; (e) about 5 mM to about 10 mM calcium chloride; and (f) about 0.008% (w/v) to about 0.025% of polysorbate 20 or polysorbate 80. In other embodiments, the pharmaceutical composition comprises about 275 mM to about 325 mM NaCl.

In certain embodiments, a pharmaceutical composition comprises: (a) about 150 IU/ml, about 287.5 IU/ml, about 431.25 IU/ml, about 575 IU/ml, about 862.5 IU/ml, about 1150 IU/ml, about 1725 IU/ml, about 2300 IU/ml, about 2875 IU/ml, or about 3450 IU/ml of a FVIII polypeptide; (b) about 2.0% (w/v) of sucrose; (c) about 308 mM NaCl; (d) about 9.8 mM L-histidine; (e) about 8 mM calcium chloride; and (f) about 0.020% (w/v) of polysorbate 20 or polysorbate 80. In other embodiments, a pharmaceutical composition comprises: (a) about 50 IU/ml to about 2500 IU/ml of a FVIII polypeptide; (b) about 10 mg/ml to about 25 mg/ml of sucrose; (c) about 8.8 mg/ml to about 14.6 mg/ml NaCl; (d) about 0.75 mg/ml to about 2.25 mg/ml L-histidine; (e) about 0.75 mg/ml to about 1.5 mg/ml calcium chloride dihydrate; and (1) about 0.08 mg/ml to about 0.25 mg/ml of polysorbate 20 or polysorbate 80. In some embodiments, a pharmaceutical composition comprises: (a) about 83 IU/ml, about 167 IU/ml, about 250 IU/ml, about 333 IU/ml, about 500 IU/ml, about 667 IU/ml, about 1000 IU/ml, about 1333 IU/ml, about 1667 IU/ml, or about 2000 IU/ml of a FVIII polypeptide; (b) about 13.3 mg/ml of sucrose; (c) about 12.0 mg/ml NaCl; (d) about 1.03 mg/ml L-histidine; (e) about 0.8 mg/ml calcium chloride dihydrate; and (f) about 0.13 mg/ml of polysorbate 20 or polysorbate 80.

In other embodiments, a pharmaceutical composition comprises: (a) about 100 IU/ml to about 4000 IU/ml of a FVIII polypeptide; (b) about 10 mg/ml to about 25 mg/ml of sucrose; (c) about 14.6 mg/ml to about 20.5 mg/ml NaCl; (d) about 0.75 mg/ml to about 2.25 mg/ml L-histidine; (e) about 0.75 mg/ml to about 1.5 mg/ml calcium chloride dihydrate; and (f) about 0.08 mg/ml to about 0.25 mg/ml of polysorbate 20 or polysorbate 80. In certain embodiments, a pharmaceutical composition comprises: (a) about 150 IU/ml, about 287.5 IU/ml, about 431.25 IU/ml, about 575 IU/ml, about 862.5 IU/ml, about 1150 IU/ml about 1725 IU/ml, about 2300 IU/ml, about 2875 IU/ml, or about 3450 IU/ml of a FVIII polypeptide; (c) about 20.0 mg/ml of sucrose; (c) about 18.0 mg/ml NaCl; (d) about 1.55 mg/ml L-histidine; (e) about 1.18 mg/ml calcium chloride dihydrate; and (f) about 0.20 mg/ml of polysorbate 20 or polysorbate 80.

In some embodiments, the present invention includes a pharmaceutical kit comprising: (a) a first container comprising a lyophilized powder, wherein the powder comprises (i) a FVIII polypeptide, (ii) one or more stabilizing agents selected from sucrose, trehalose, raffinose, arginine, or mixture thereof; (iii) sodium chloride (NaCl); (iv) L-histidine; (v) calcium chloride; and (vi) polysorbate 20 or polysorbate 80; and (b) a second container comprising sterilized water for injections to be combined with the lyophilized powder of the first container. In other embodiments, a pharmaceutical kit comprises: (a) a first container comprising a lyophilized powder, where the powder comprises (i) about 250 IU, about 500 IU, about 750 IU, about 1000 IU, about 1500 IU, about 2000 IU, about 3000 IU, about 4000 IU, about 5000 IU, or about 6000 IU of a FVIII polypeptide, (ii) about 40 mg of sucrose; (iii) about 36 mg of sodium chloride; (iv) about 3.1 mg of L-histidine; (v) about 2.40 mg of calcium chloride dihydrate; and (v) about 0.40 mg of polysorbate 20 or polysorbate 80; and (b) a second container comprising sterilized water for injections at a volume sufficient to produce, when combined with the lyophilized powder of the first container, a solution comprising: (i) about 83 IU/ml, about 167 IU/ml, about 250 IU/ml, about 333 IU/ml, about 500 IU/ml, about 667 IU/ml, about 1000 IU/ml, about 1333 IU/ml, about 1667 IU/ml, or about 2000 IU/ml of a FVIII polypeptide, respectively; (ii) about 1.33% (w/v) of sucrose; (iii) about 205 mM NaCl; (iv) about 6.64 mM L-histidine; (v) about 5.4 mM of calcium chloride; and (vi) about 0.013% (w/v) of polysorbate 20 or polysorbate 80.

In other embodiments, a pharmaceutical kit comprises: (a) a first container comprising a lyophilized powder, where the powder comprises (i) about 250 IU, about 500 IU, about 750 IU, about 1000 IU, about 1500 IU, about 2000 IU, about 3000 IU, about 4000 IU, about 5000 IU, or about 6000 IU of a FVIII polypeptide, (ii) about 40 mg of sucrose; (iii) about 36 mg of sodium chloride; (iv) about 3.1 mg of L-histidine; (v) about 2.40 mg of calcium chloride dihydrate; and (v) about 0.40 mg of polysorbate 20 or polysorbate 80; and (b) a second container comprising sterilized water for injections at a volume sufficient to produce, when combined with the lyophilized powder of the first container, a solution comprising: (i) about 83 IU/ml, about 167 IU/ml, about 250 IU/ml, about 333 IU/ml, about 500 IU/ml, about 667 IU/ml, about 1000 IU/ml, about 1333 IU/ml, about 1667 IU/ml, or about 2000 IU/ml of a FVIII polypeptide, respectively; (ii) about 13.3 mg/ml of sucrose; (iii) about 12.0 mg/ml of NaCl; (iv) about 1.03 mg/ml of L-histidine; (v) about 0.80 mg/ml of calcium chloride; and (vi) about 0.13 mg/ml of polysorbate 20 or polysorbate 80.

The invention also includes a method of reducing or decreasing a bleeding episode or treating or preventing a bleeding condition comprising administering a pharmaceutical composition comprising a FVIII polypeptide.

BRIEF DESCRIPTION OF THE DRAWINGS

FIG. 1 shows details on the design of the sequential PK subgroup (Arm 1) dosing and PK sampling.

DETAILED DESCRIPTION OF THE INVENTION

Figure 2:
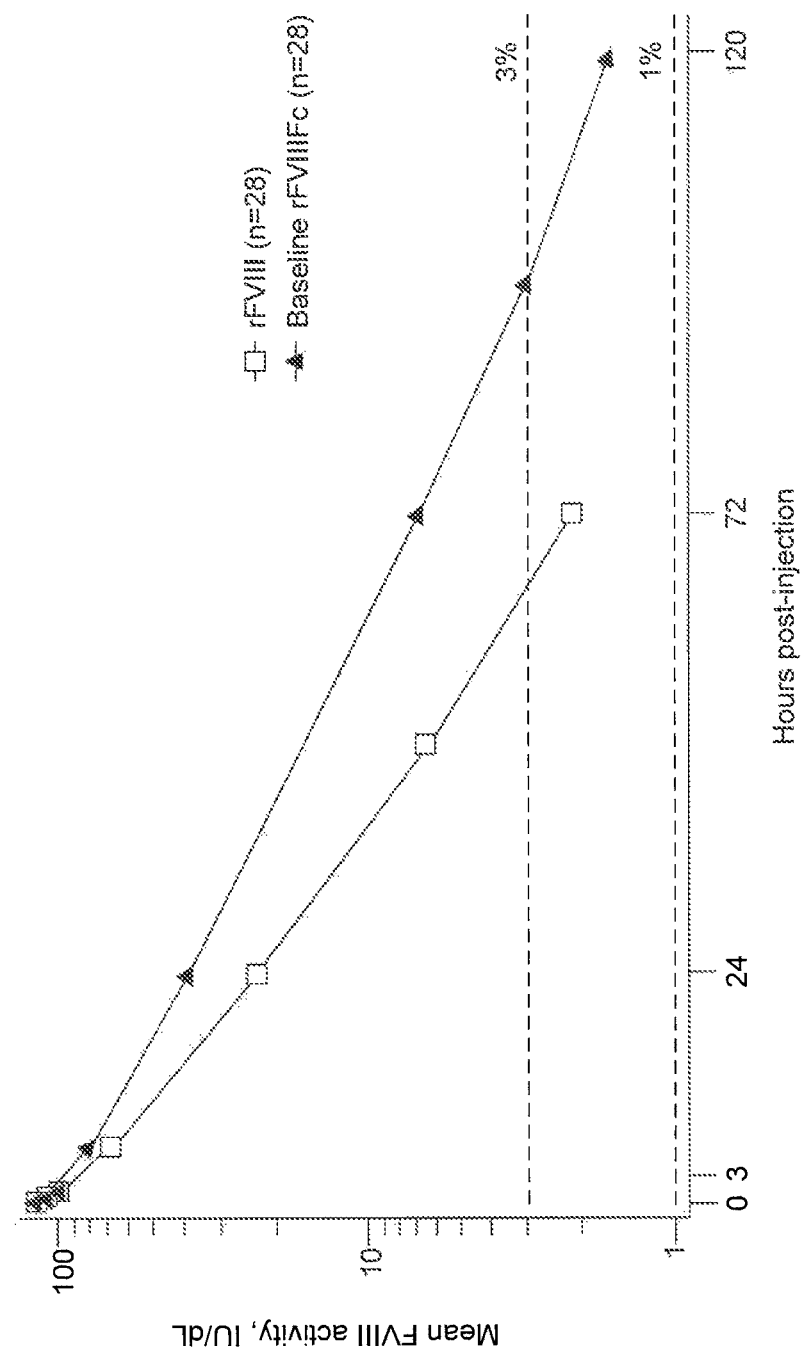
FIG. 2 shows the mean observed FVIII activity with rFVIIIFc and rFVIII over time: one stage clotting assay (logarithmic scale) in the sequential pharmacokinetic subgroup. rFVIIIFc demonstrated an approximate 50% longer elimination half-life and mean residence time compared with wild-type Factor VIII (a short-acting FVIII polypeptide) ($P<0.001$).

The present invention provides a formulation for a Factor VIII polypeptide, e.g., FVIII-Fc, and methods of using thereof.

I. Definitions

It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising," otherwise analogous embodiments described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety. Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The term "polypeptide," "peptide" and "protein" are used interchangeably and refer to a polymeric compound comprised of covalently linked amino acid residues.

The term "polynucleotide" and "nucleic acid" are used interchangeably and refer to a polymeric compound comprised of covalently linked nucleotide residues. Polynucleotides can be DNA, cDNA, RNA, single stranded, or double stranded, vectors, plasmids, phage, or viruses. Polynucleotides include those in Table 10, which encode the polypeptides of Table 11 (see Table 10). Polynucleotides also include fragments of the polynucleotides of Table 10, e.g., those that encode fragments of the polypeptides of Table 11, such as the Factor VIII, Fc, signal sequence, propeptide, and other fragments of the polypeptides of Table 11.

"Administering," as used herein, means to proscribe or give a pharmaceutical composition comprising a Factor VIII polypeptide of the invention to a subject via a pharmaceutically acceptable route. Examples of routes of administration include, but are not limited to, intravenous, e.g., intravenous injection and intravenous infusion, e.g., via central venous access. Additional routes of administration include subcutaneous, intramuscular, oral, nasal, and pulmonary administration. Advantages of the present invention include: improved regimen compliance; reduced break through bleeds; increased protection of joints from bleeds; prevention of joint damage; reduced morbidity; reduced mortality; prolonged protection from bleeding; decreased thrombotic events; and improved quality of life.

The terms "long-acting" and "long-lasting" are used interchangeably herein. In one embodiment, the term "long-acting" or "long-lasting" indicates that a FVIII activity as a result of administration of the "long-acting" FVIII polypeptide is longer than the FVIII activity of a wild-type FVIII (e.g., ADVATE® or plasma-derived FVIII ("pdFVIII")). The "longer" FVIII activity can be measured by any known methods in the art, e.g., aPTT assay, chromogenic assay, ROTEM®, TGA, etc. In one embodiment, the "longer" FVIII activity can be shown by the $T_{1/2beta}$ (activity). In another embodiment, the "longer" FVIII activity can be shown by the level of FVIII antigen present in plasma, e.g., by the $T_{1/2beta}$ (antigen). In other embodiments, the long-acting or long-lasting FVIII polypeptide works longer in a coagulation cascade, e.g., is active for a longer period, compared to a wild-type FVIII polypeptide, i.e., a polypeptide consisting of amino acids 20 to 1457 of SEQ ID NO: 2, i.e., SQ BDD FVIII (REFACTO®) or a polypeptide consisting of amino acids 20 to 2351 of SEQ ID NO: 6 (ADVATE®).

The terms "short-acting" and "short-lasting" are used interchangeably herein. The term "short-acting" or "short-lasting" indicates that a FVIII activity as a result of administration of the "short-acting" FVIII polypeptide is similar to or the same as the FVIII activity of a wild-type FVIII (e.g., ADVATE® (amino acids 20 to 2351 of SEQ ID NO: 6), REFACTO® (amino acids 20 to 1457 of SEQ ID NO: 2), or plasma-derived FVIII ("pdFVIII")) or shorter than the FVIII activity of a long-acting FVIII polypeptide. The "shorter" FVIII activity can be measured by any known methods in the art, e.g., aPTT assay, chromogenic assay, ROTEM®, TGA, etc. Exemplary short-acting FVIII polypeptides include, but are not limited to, wild-type mature FVIII polypeptide (ADVATE®, RECOMBINATE®, or HELIXATE®) or B-domain deleted FVIII polypeptides such as SQ BDD FVIII (REFACTO® and XYNTHA®) or FVIII polypeptides containing 21 amino acids from B-domain (i.e., SFSQNSRHPSQNPPVLKRHQR, SEQ ID NO: 17) (e.g., NOVOEIGHT®).

The term "chimeric polypeptide," as used herein, means a polypeptide that includes within it at least two polypeptides (or portions thereof such as subsequences or peptides) from different sources. Chimeric polypeptides can include two, three, four, five, six, seven, or more polypeptides or portions thereof from different sources, such as different genes, different cDNAs, or different animal or other species. Chimeric polypeptides can include one or more linkers joining the different polypeptides or portions thereof. Thus, the polypeptides or portions thereof can be joined directly or they can be joined indirectly, via linkers, or both, within a single chimeric polypeptide. Chimeric polypeptides can include additional peptides such as signal sequences and sequences such as 6His and FLAG that aid in protein purification or detection. In addition, chimeric polypeptides can have amino acid or peptide additions to the N- and/or C-termini. In some embodiments, a chimeric polypeptide is a long-acting FVIII polypeptide. Exemplary chimeric polypeptides of the invention are Factor VIII-FcRn BP chimeric polypeptides, e.g., Factor VIII-Fc polypeptides such as the FVIIIFc, SEQ ID NO:2 or 6 (Table 11) with or without its signal sequence and propeptide.

"Hybrid" polypeptides and proteins, as used herein, means a combination of a chimeric polypeptide with a second polypeptide. The chimeric polypeptide and the second polypeptide in a hybrid can be associated with each other via protein-protein interactions, such as charge-charge or hydrophobic interactions. The chimeric polypeptide and the second polypeptide in a hybrid can be associated with each other via disulfide or other covalent bond(s). Hybrids are described in WO 2004/101740 and WO 2006/074199, each of which is incorporated herein by reference in its entirety. See also U.S. Pat. Nos. 7,404,956 and 7,348,004, each of which is incorporated herein by reference in its entirety. The second polypeptide can be a second copy of the same chimeric polypeptide or it can be a non-identical chimeric polypeptide. See, e.g., Table 11. In one embodiment, the second polypeptide is a polypeptide comprising an FcRn binding partner. FcRn binding partners binds to FcRn and protects the FcRn binding partner containing molecule from catabolism, thus extending the plasma half-life. In another embodiment, the chimeric polypeptide is a chimeric Factor VIII-Fc polypeptide and the second polypeptide consists essentially of Fc, e.g., a rFVIII Fc recombinant fusion protein consisting of a single molecule of recombinant B-domain deleted human FVIII (BDD-rFVIII) fused to the dimeric Fc domain of the human IgG1, with no intervening linker sequence. This hybrid polypeptide is referred to herein as FVIIIFc monomeric Fc fusion protein, FVIIIFc monomer hybrid, monomeric FVIIIFc hybrid, and FVIIIFc monomer-dimer. See Table 11A. The Examples provide preclinical and clinical data for this hybrid polypeptide.

The second polypeptide in a hybrid can comprise or consist essentially of a sequence at least 90% or 95% identical to the amino acid sequence shown in Table 11A(ii) without a signal sequence (amino acids 21 to 247 of SEQ ID NO:4) or at least 90% or 95% identical to the amino acid sequence shown in Table 11A(ii) with a signal sequence (amino acids 1 to 247 of SEQ ID NO:4). The second polypeptide can comprise or consist essentially of a sequence identical to the amino acid sequence shown in Table 11A(ii) without a signal sequence (amino acids 21 to 247 of SEQ ID NO:4) or identical to the amino acid sequence shown in Table 11A(ii) with a signal sequence (amino acids 1 to 247 of SEQ ID NO:4).

Factor VIII coagulant activity is expresses as International Unit(s) (IU). One IU of Factor VIII activity corresponds approximately to the quantity of Factor VIII in one milliliter of normal human plasma. Several assays are available for measuring Factor VIII activity, including the one stage clotting assay (activated partial thromboplastin time; aPTT), thrombin generation time (TGA) and rotational thromboelastometry (ROTEM®).

The term "lyophilisate" as used herein in connection with the formulation according to the invention denotes a formulation which is manufactured by freeze-drying methods known in the art per se. The solvent (e.g. water) is removed by freezing following sublimation under vacuum and desorption of residual water at elevated temperature. In the pharmaceutical field, the lyophilisate has usually a residual moisture of about 0.1 to 5% (w/w) and is present as a powder or a physical stable cake. The lyophilisate is characterized by a fast dissolution after addition of a reconstitution medium.

The term "reconstituted formulation" as used herein denotes a formulation which is lyophilized and re-dissolved by addition of a diluent. The diluent can contain, without limitation, water for injection (WFI), bacteriostatic water for injection (BWFI), sodium chloride solutions (e.g. 0.9% (w/v) NaCl), glucose solutions (e.g. 5% glucose), surfactant containing solutions (e.g. 0.01% polysorbate 20 or polysorbate 80), a pH-buffered solution (e.g. phosphate-buffered solutions) and combinations thereof.

"Dosing interval," as used herein, means the amount of time that elapses between multiple doses being administered to a subject. Dosing interval can thus be indicated as ranges. The dosing interval in the methods of the invention using a chimeric FVIII-FcRn BP, e.g., a chimeric FVIII-Fc, can be at least about one and one-half to eight times longer than the dosing interval required for an equivalent amount (in IU/kg) of the Factor VIII without the FcRn BP, e.g., Fc portion (i.e., a polypeptide consisting of said FVIII). The dosing interval when administering. e.g., a Factor VIII-Fc chimeric polypeptide (or a hybrid) of the invention can be at least about one and one-half times longer than the dosing interval required for an equivalent amount of the Factor VIII without the FcRn BP, e.g., Fc portion (i.e., a polypeptide consisting of the Factor VIII). The dosing interval can be at least about one and one-half to eight times longer than the dosing interval required for an equivalent amount of the Factor VIII without, e.g., the Fc portion (or a polypeptide consisting of the Factor VIII).

The term "dosing frequency" as used herein refers to the frequency of administering doses of a FVIII polypeptide in a given time. Dosing frequency can be indicated as the number of doses per a given time, e.g., once a week or once in two weeks.

The term "prophylaxis of one or more bleeding episode" or "prophylactic treatment" as used herein means administering a FVIII polypeptide in multiple doses to a subject over a course of time to increase the level of FVIII activity in a subject's plasma. In one embodiment, "prophylaxis of one or more bleeding episode" indicates use of a FVIII polypeptide to prevent or inhibit occurrence of one or more spontaneous or uncontrollable bleeding or bleeding episodes or to reduce the frequency of one or more spontaneous or uncontrollable bleeding or bleeding episodes. In another embodiment, the increased FVIII activity level is sufficient to decrease the incidence of spontaneous bleeding or to prevent bleeding in the event of an unforeseen injury. Prophylactic treatment decreases or prevents bleeding episodes, for example, those described under on-demand treatment. Prophylactic treatment can be individualized, as discussed under "dosing interval", e.g., to compensate for inter-patient variability.

The term "about twice weekly" as used herein means approximate number, and "about twice weekly" can include twice in one week, e.g., a first dose in three days and a second dose in three days, a first dose in three days and a second dose in four days, a first dose in four days and a second dose in three days, a first dose in four days and a second dose in four days. The term "about twice weekly" can also include every three days, every four days, or every five days.

The term "about once a week" as used herein means approximate number, and "about once a week" can include every seven days±two days, i.e., every five days to every nine days. The dosing frequency of "once a week" thus can be every five days, every six days, every seven days, every eight days, or every nine days.

The term "individualized prophylaxis" or "prophylactic and individualized" as used herein means use of a FVIII polypeptide for an individualized dosing and/or dosing interval or frequency to prevent or inhibit occurrence of one or more spontaneous and/or uncontrollable bleeding or bleeding episodes or to reduce the frequency of one or more spontaneous and/or uncontrollable bleeding or bleeding episodes. "Individualized" within the context of prophylaxis is used synonymous with "tailored" throughout this application. For example, "individualized prophylaxis" also means "tailored prophylaxis" and "prophylactic and individualized" also means "prophylactic and tailored." In one embodiment, the "individualized interval" includes every 3 days±2 days, i.e., every day to every five days. The dosing frequency of the "individualized interval prophylaxis" thus can be every day, every two days, every three days, every four days, or every five days.

The term "on-demand treatment," as used herein, means treatment that is intended to take place over a short course of time and is in response to an existing condition, such as a bleeding episode, or a perceived short term need such as planned surgery. The "on-demand treatment" is used interchangeably with "episodic" treatment. Conditions that can require on-demand treatment include a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. Bleeding episodes other than these are also included. The subject can be in need of surgical prophylaxis, peri-operative management, or treatment for surgery. Such surgeries include minor surgery, major surgery, tooth extraction, tonsillectomy, other dental/thoraco-facial surgeries, inguinal herniotomy, synovectomy, total knee replacement, other joint replacement, craniotomy, osteosynthesis, trauma surgery, intracranial surgery, intra-abdominal surgery, or intrathoracic surgery. Surgeries other than these are also included.

Additional conditions that can require on-demand treatment include minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Additional reasons for on-demand treatment include the need for peri-operative management for surgery or dental extraction, major surgery, extensive oral surgery, urologic surgery, hernia surgery, orthopedic surgery such as replacement of knee, hip, or other major joint.

The term "treatment" or "treating" as used herein means amelioration or reduction of one or more symptoms of bleeding diseases or disorders including, but not limited to, hemophilia B. In one embodiment, "treatment of" or "treating" a bleeding disease or disorder includes prevention of one or more symptoms of a bleeding disease or disorder. In a bleeding disease or disorder caused by a FVIII deficiency (e.g., a low baseline FVIII activity), the term "treatment" or "treating" means a FVIII replacement therapy. By administering a pharmaceutical composition comprising a FVIII polypeptide to a subject, the subject can achieve and/or maintain a plasma trough level of a FVIII activity at about 1 IU/dl or above 1 IU/dl. In other embodiments, "treatment" or "treating" means reduction of the frequency of one or more symptoms of bleeding diseases or disorders, e.g., spontaneous or uncontrollable bleeding episodes. "Treatment," however, need not be a cure.

The term "perioperative management" as used herein means use of a pharmaceutical composition comprising a FVIII polypeptide before, concurrently with, or after an operative procedure, e.g., a surgical operation. The use for "perioperative management" of one or more bleeding episode includes surgical prophylaxis before (i.e., preoperative), during (i.e., intraoperative), or after (i.e., postoperative) a surgery to prevent one or more bleeding or bleeding episode or reducing or inhibiting spontaneous and/or uncontrollable bleeding episodes before, during, and after a surgery.

"Baseline," as used herein, is the lowest measured plasma Factor VIII level in a subject prior to administering a dose. The FVIII plasma levels can be measured at two time points prior to dosing: at a screening visit and immediately prior to dosing. Alternatively, (a) the baseline in patients whose pretreatment FVIII activity is <1%, who have no detectable FVIII antigen, and have nonsense genotypes can be defined as 0%, (b) the baseline for patients with pretreatment FVIII activity <1% and who have detectable FVIII antigen can be set at 0.5%, (c) the baseline for patients whose pretreatment FVIII activity is between 1-2% is Cmin (the lowest activity throughout the PK study), and (d) the baseline for patients whose pretreatment FVIII activity is ≥2% can be set at 2%. Activity above the baseline pre-dosing can be considered residue drug from prior treatment, and can be decayed to baseline and subtracted from the PK data following rFVIIIFc dosing.

"$T_{1/2\beta}$," or "$T_{1/2\ beta}$" or "Beta HL," as used herein, is half-life associated with elimination phase, $t\frac{1}{2}\beta=(\ln 2)$/elimination rate constant associated with the terminal phase. The $T_{1/2\ beta}$ can be measured by FVIII activity or by FVIII antigen level in plasma. The $T_{1/2\ beta}$ based on activity is shown as $T_{1/2\ beta}$ (activity), and the $T_{1/2\ beta}$ based on the FVIII antigen level can be shown as $T_{1/2\ beta}$ (antigen). Both $T_{1/2\ beta}$ (activity) and $T_{1/2\ beta}$ (antigen) can be shown as ranges or a geometric mean.

"Trough," as used herein, is the lowest plasma FVIII activity level reached after administering a dose of chimeric polypeptide of the invention or another FVIII molecule and before the next dose is administered, if any. Trough is used interchangeably herein with "threshold." Baseline FVIII levels are subtracted from measured FVIII levels to calculate the trough level.

The term "annualized bleeding rate" ("ABR") as used herein refers to the number of bleeding episodes (including spontaneous and traumatic bleeds) experienced by a subject during a defined time period, extrapolated to 1 year. For example two bleeds in six months would indicate an ABR of four. The median ABR provides the middle value among all observed ABRs, indicating that half of the subjects had individual ABRs less than or equal to the median and half had ABRs greater than or equal to the median.

The term "inter quartile range" ("IQR") as used herein refers to a measure of statistical dispersion, being equal to the difference between the upper and lower quartiles. Unlike (total) range, the interquartile range is a robust statistic, having a breakdown point of 25%, and is thus often preferred to the total range. For a symmetric distribution (where the median equals the midline, the average of the first and third quartiles), half the IQR equals the median absolute deviation (MAD). The median is the corresponding measure of central tendency.

"Subject," as used herein means a human. Subject as used herein includes an individual who is known to have at least one incidence of uncontrolled bleeding episodes, who has been diagnosed with a disease or disorder associated with uncontrolled bleeding episodes, e.g., a bleeding disease or disorder, e.g., hemophilia A, who is susceptible to uncontrolled bleeding episodes, e.g., hemophilia, or any combinations thereof. Subjects can also include an individual who is in danger of one or more uncontrollable bleeding episodes prior to a certain activity, e.g., a surgery, a sport activity, or any strenuous activities. The subject can have a baseline FVIII activity less than 1%, less than 0.5%, less than 2%, less than 2.5%, less than 3%, or less than 4%. Subjects also include pediatric humans. Pediatric human subjects are birth to 20 years, preferably birth to 18 years, birth to 16 years, birth to 15 years, birth to 12 years, birth to 11 years, birth to 6 years, birth to 5 years, birth to 2 years, or 2 to 11 years of age.

"Therapeutic dose," "dose," "effective dose," or "dosing amount" as used herein, means a dose that achieves a plasma trough level of a FVIII activity at least about 1 IU/dl or above 1 IU/dl in the subject administered with a pharmaceutical composition comprising a FVIII polypeptide. For the purpose of this invention, in one embodiment, the "dose" refers to the amount of the doses that a plasma trough level of a FVIII activity is maintained at least about 1 IU/dl or above 1 IU/dl, at least about 2 IU/dl or above 2 IU/dl, at least about 3 IU/dl or above 3 IU/dl, at least about 4 IU/dl or above 4 IU/dl, or at least about 5 IU/dl or above 5 IU/dl throughout the administration of a pharmaceutical composition comprising a FVIII polypeptide. In another embodiment, the "dose" reduces or decreases frequency of bleeding or bleeding disorder. In other embodiments, the "dose" stops on-going, uncontrollable bleeding or bleeding episodes. In still other embodiments, the "dose" prevents spontaneous bleeding or bleeding episodes in a subject susceptible to such spontaneous bleeding or bleeding episodes. The "dose" or "therapeutic dose" need not cure hemophilia.

The term "target joint" is defined as a major joint (e.g., hip, elbow, wrist, shoulder, knee, and ankle) into which repeated bleeding occurs (frequency of ≥3 bleeding episodes into the same joint in a consecutive 6-month period).

The term "bleeding episode" as used herein adopts a standardized definition of a bleeding episode. A bleeding episode started from the first sign of bleeding, and ended 72 hours after the last treatment for the bleeding, within which any symptoms of bleeding at the same location, or injections less than or equal to 72 hours apart, were considered the same bleeding episode. Any injection to treat the bleeding episode, taken more than 72 hours after the preceding one, was considered the first injection to treat a new bleeding episode at the same location. Any bleeding at a different location was considered a separate bleeding episode regardless of time from last injection. This definition has been proposed by the Subcommittee on Standards and Criteria, FVIII/FIX subcommittee of the International Society of Thrombosis and Hemostasis and has been used by the PedNet multicenter study in hemophilia.

The term "annualized bleeding rates (ABRs) as used herein refers to the number of bleeding episodes that are annualized for each patient using the following formula:

$$ABR = \frac{\text{Number of bleeding episodes during efficacy period}}{\text{Total number of days during the efficacy period}} \times 365.25$$

"Variant," as used herein, refers to a polynucleotide or polypeptide differing from the original polynucleotide or polypeptide, but retaining essential properties thereof, e.g., Factor VIII coagulant activity or Fc (FcRn binding) activity. Generally, variants are overall closely similar, and, in many regions, identical to the original polynucleotide or polypeptide. Variants include polypeptide and polynucleotide fragments, deletions, insertions, and modified versions of original polypeptides.

II. Pharmaceutical Composition

The present invention is directed to a FVIII polypeptide formulated as a pharmaceutical composition. The pharmaceutical composition can be formulated for administration to humans. The FVIII polypeptide can be a short-acting FVIII polypeptide or a long-acting FVIII polypeptide. The pharmaceutical compositions comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Various methods of formulating the invention are well known in the art.

In certain formulations provided herein, a FVIII polypeptide is formulated as a sterile, preservative-free, non-pyrogenic, lyophilized, white to off-white powder to cake, for intravenous (IV) administration. The formulation can be provided in a single-use vial.

In certain embodiments, a FVIII polypeptide (e.g., a long-acting or short-acting FVIII polypeptide, e.g., rFVIIIFc) formulation is provided in a single-use vial manufactured to contain, following reconstitution with an appropriate amount of diluent, about 83 IU/ml, 167 IU/ml, 250 IU/ml, 333 IU/ml, 500 IU/ml, 667 IU/ml, 1000 IU/ml, 1333 IU/ml, 1667 IU/ml, or 2000 IU/ml of the long-acting FVIII polypeptide. In certain embodiments in which diluent is added to a final volume of about 3 ml, a single-use vial can nominally contain about 250, about 500, about 750, about 1000, about 1500, about 2000, about 3000, about 4000, about 5000, or about 6000 International Units (IU) of the FVIII polypeptide (e.g., a long-acting or short-acting FVIII polypeptide, e.g., rFVIIIFc).

In certain embodiments the formulation includes, in addition to the active FVIII polypeptide (e.g., a long-acting or short-acting FVIII polypeptide, e.g., rFVIIIFc): sucrose (which can act as a stabilizer), sodium chloride (which can act as a bulking agent), L-histidine (which can act as a buffer), calcium chloride, and polysorbate 20 or polysorbate 80 (which can act as a stabilizer). The formulation is provided with a diluent comprising a sterile sodium chloride solution. In certain embodiments, the diluent is provided in a pre-filled syringe.

Accordingly, provided herein is a pharmaceutical composition comprising a specified amount of a FVIII polypeptide (e.g., a long-acting or short-acting FVIII polypeptide, e.g., rFVIIIFc) (in IU), along with the excipients sucrose, NaCl, L-histidine, calcium chloride, and polysorbate 20 or polysorbate 80. The compositions provided herein comprise various concentrations of the various excipients, and the concentrations can be expressed in various ways. For example, the concentration of a given excipient can be expressed as a molar concentration (e.g., M or mM), as a weight/volume percent, (e.g., grams per 100 ml diluent), or as milligrams per milliliter (mg/ml). Formulations provided herein can contain specified amounts of the various excipients at a level of precision ranging from approximate, e.g., concentrations expressed only to one significant figure (e.g., about 0.1% (w/v)), or with more precision, e.g., out to 2, 3, 4, 5, or 6 significant figures (e.g., about 3.88 mg/ml, with precision out to three significant figures). The necessary level of precision can vary depending on, e.g., the requirements of a given regulatory agency, or the manufacturing process. In certain embodiments the pharmaceutical composition comprises a reconstituted formulation, which can be provided as a lyophilisate, optionally accompanied by a diluent.

In certain embodiments, the pharmaceutical composition comprises about 50 IU/ml to about 2500 IU/ml rFVIIIFc, e.g., 83 IU/ml, 167 IU/ml, 250 IU/ml, 333 IU/ml, 500 IU/ml, 667 IU/ml, 1000 IU/ml, 1333 IU/ml, 1667 IU/ml, or 2000 IU/ml of a FVIII polypeptide (e.g., a long-acting or short-acting FVIII polypeptide, e.g., rFVIIIFc). In certain embodiments, the pharmaceutical composition comprises 83 IU/ml, 167 IU/ml, 250 IU/ml, 333 IU/ml, 500 IU/ml, 667 IU/ml, 1000 IU/ml, 1333 IU/ml, 1667 IU/ml, or 2000 IU/ml of a FVIII polypeptide (e.g., a long-acting or short-acting FVIII polypeptide, e.g., rFVIIIFc) in a formulation comprising about 13.3 mg/ml or about 1.33% (w/v) sucrose, about 12.0 mg/ml or about 205 mM NaCl, about 1.03 mg/ml or about 6.64 mM L-histidine, about 0.80 mg/ml or about 5.4 mM calcium chloride dihydrate, and about 0.13 mg/ml or about 0.013% (w/v) polysorbate 20 or polysorbate 80.

In certain embodiments, the pre-lyophilization pharmaceutical composition comprises about 100 IU/ml to about 4000 IU/ml rFVIIIFc, e.g., 150 IU/ml, 287.5 IU/ml, 431.25 IU/ml, 575 IU/ml, 862.5 IU/ml, 1150 IU/ml, 1725 IU/ml, 2300 IU/ml, 2875 IU/ml, or 3450 IU/ml of a FVIII polypeptide (e.g., a long-acting or short-acting FVIII polypeptide, e.g., rFVIIIFc). In certain embodiments, the pharmaceutical composition comprises 150 IU/ml, 287.5 IU/ml, 431.25 IU/ml, 575 IU/ml, 862.5 IU/ml, 1150 IU/ml, 1725 IU/ml, 2300 IU/ml, 2875 IU/ml, or 3450 IU/ml of a FVIII polypeptide (e.g., a long-acting or short-acting FVIII polypeptide, e.g., rFVIIIFc) in a formulation comprising about 20.0 mg/ml or about 2.0% (w/v) sucrose, about 18.0 mg/ml or about 308 mM NaCl, about 1.55 mg/ml or about 9.8 mM L-histidine, about 1.18 mg/ml or about 8.0 mM calcium chloride dihydrate, and about 0.2 mg/ml or about 0.02% (w/v) polysorbate 20 or polysorbate 80.

In certain embodiments, the pharmaceutical composition comprises a pharmaceutically acceptable amount of sucrose. In certain embodiments, the pharmaceutical composition comprises about 1% (w/v) to about 2.5% (w/v) sucrose, preferably about 1.3% (w/v) to about 2% sucrose (w/v) e.g., about 1.33% (w/v) sucrose or about 2.0% (w/v) sucrose. In certain related embodiments the pharmaceutical composition comprises about 10 mg/ml to about 25 mg/ml sucrose, preferably about 13 mg/ml to about 20 mg/ml sucrose, e.g., about 13.3 mg/ml sucrose or about 20.0 mg/ml sucrose. In still other embodiments, stabilizing agents such as trehalose, raffinose and/or arginine can be used at these concentrations in lieu of or in combination with sucrose.

In certain embodiments, the pharmaceutical composition comprises about 150 mM to about 250 mM NaCl, about 175 mM to about 225 mM NaCl, and about 200 mM to about 210 mM NaCl, e.g., about 205 mM NaCl. In certain related embodiments, the pharmaceutical composition comprises about 8.8 mg/ml to about 14.6 mg/ml NaCl, about 10 mg/ml NaCl to about 13 mg/ml, e.g., about 12.0 mg/ml NaCl. In certain embodiments, NaCl is provided at the desired concentration in a diluent solution in which a lyophilisate comprising a FVIII polypeptide (e.g., a long-acting or short-acting FVIII polypeptide, e.g., rFVIIIFc) is reconstituted.

In another embodiment, the compositions of the invention do not include bulking agents such as mannitol, glycine, alanine and/or hydroxyethyl starch. In other embodiments, NaCl is the sole bulking agent.

In certain embodiments, the pre-lyophilization pharmaceutical composition comprises about 250 mM to about 350 mM NaCl, about 275 mM to about 325 mM NaCl, e.g., about 308 mM NaCl. In certain related embodiments, the pharmaceutical composition comprises about 14.6 mg/ml to about 20.5 mg/ml NaCl, about 16 mg/ml to about 19 mg/ml, e.g., about 18.0 mg/ml NaCl.

In certain embodiments, the pharmaceutical composition comprises a pharmaceutically acceptable amount of L-histidine. In certain embodiments, the pharmaceutical composition comprises about 5 mM to about 15 mM L-histidine, e.g., about 6.64 mM L-histidine or about 9.8 mM L-histidine. In certain related embodiments the pharmaceutical composition comprises about 0.75 mg/ml to about 2.25 mg/ml L-histidine, e.g., about 1.03 mg/ml L-histidine or about 1.55 mg/ml L-histidine. In certain embodiments, L-histidine is provided as part of a lyophilisate, which, upon reconstitution with an appropriate amount of diluent provides L-histidine at the desired concentration.

In certain embodiments, the pharmaceutical composition comprises a pharmaceutically acceptable amount of calcium chloride. In certain embodiments, the pharmaceutical composition comprises about 5 mM to about 10 mM calcium chloride, e.g., about 5.4 mM calcium chloride or about 8 mM calcium chloride. In certain related embodiments the pharmaceutical composition comprises about 0.75 mg/ml to about 1.5 mg/ml calcium chloride dihydrate, e.g., about 0.8 mg/ml calcium chloride dihydrate or about 1.18 mg/ml calcium chloride dihydrate. In certain embodiments, calcium chloride is provided as part of a lyophilisate, which, upon reconstitution with an appropriate amount of diluent provides calcium chloride at the desired concentration.

In certain embodiments, the pharmaceutical composition comprises a pharmaceutically acceptable amount of polysorbate 20 or polysorbate 80. In certain related embodiments the pharmaceutical composition comprises about 0.008% (w/v) to about 0.025% (w/v) polysorbate 20 or polysorbate 80, e.g., about 0.013% (w/v) polysorbate 20 or polysorbate 80 or about 0.02% (w/v) polysorbate 20 or polysorbate 80. In certain related embodiments the pharmaceutical composition comprises about 0.08 mg/ml to about 0.25 mg/ml polysorbate 20 or polysorbate 80, e.g., about 0.13% mg/ml polysorbate 20 or polysorbate 80 or about 0.20 mg/ml polysorbate 20 or polysorbate 80. In certain embodiments, polysorbate 20 or polysorbate 80 is provided as part of a lyophilisate, which, upon reconstitution with an appropriate amount of diluent provides polysorbate 20 or polysorbate 80 at the desired concentration.

In certain embodiments, the pharmaceutical composition comprises: about 50 IU/ml to about 2500 IU/ml of a FVIII polypeptide (e.g., a long-acting or short-acting FVIII polypeptide, e.g., rFVIIIFc); about 1% (w/v) to about 2.5% (w/v) of sucrose; about 150 mM to about 250 mM NaCl; about 5 mM to about 15 mM L-histidine; about 5 mM to about 10 mM calcium chloride; and about 0.008% (w/v) to about 0.025% of polysorbate 20 or polysorbate 80. In certain embodiments the pharmaceutical composition is provided as a lyophilisate and a diluent. In certain embodiments the amount of lyophilizate provides about 3 ml of a pharmaceutical composition with the desired ingredients at the desired concentrations.

In certain embodiments, the pharmaceutical composition comprises: about 50 IU/ml to about 2500 IU/ml of a FVIII polypeptide (e.g., a long-acting or short-acting FVIII polypeptide, e.g., rFVIIIFc); about 10 mg/ml to about 25 mg/ml of sucrose; about 8.8 mg/ml to about 14.6 mg/ml NaCl; about 0.75 mg/ml to about 2.25 mg/ml L-histidine; about 0.75 mg/ml to about 1.5 mg/ml calcium chloride dihydrate; and about 0.08 mg/ml to about 0.25 mg/ml of polysorbate 20 or polysorbate 80. In certain embodiments the pharmaceutical composition is provided as a lyophilisate and a diluent. In certain embodiments the amount of lyophilizate provides about 3 ml of a pharmaceutical composition with the desired ingredients at the desired concentrations.

Exemplary compositions are provided in Table 1 and in Table 2 in the Examples.

For example, the disclosure provides a pharmaceutical composition comprising: about 83 IU/ml of a FVIII polypeptide (e.g., a long-acting or short-acting FVIII polypeptide, e.g., rFVIIIFc); about 1.33% (w/v) of sucrose; about 205 mM NaCl; about 6.64 mM L-histidine; about 5.4 mM calcium chloride dihydrate, and about 0.013% (w/v) of polysorbate 20 or polysorbate 80. The disclosure further provides a pharmaceutical composition comprising: about 167 IU/ml of a FVIII polypeptide (e.g., a long-acting or short-acting FVIII polypeptide, e.g., rFVIIIFc); about 1.33% (w/v) of sucrose; about 205 nM NaCl; about 6.64 mM L-histidine; about 5.4 mM calcium chloride dihydrate, and about 0.013% (w/v) of polysorbate 20 or polysorbate 80. The disclosure further provides a pharmaceutical composition comprising: about 250 IU/ml of a FVIII polypeptide (e.g., a long-acting or short-acting FVIII polypeptide, e.g., rFVIIIFc); about 1.33% (w/v) of sucrose; about 205 mM NaCl; about 6.64 mM L-histidine; about 5.4 mM calcium chloride dihydrate, and about 0.013% (w/v) of polysorbate 20 or polysorbate 80. The disclosure further provides a pharmaceutical composition comprising: about 333 IU/ml of a FVIII polypeptide (e.g., a long-acting or short-acting FVIII polypeptide, e.g., rFVIIIFc); about 1.33% (w/v) of sucrose; about 205 mM NaCl; about 6.64 mM L-histidine; about 5.4 mM calcium chloride dihydrate, and about 0.013% (w/v) of polysorbate 20 or polysorbate 80. The disclosure further provides a pharmaceutical composition comprising: about 500 IU/ml of a FVIII polypeptide (e.g., a long-acting or short-acting FVIII polypeptide, e.g., rFVIIIFc); about 1.33% (w/v) of sucrose; about 205 mM NaCl; about 6.64 mM L-histidine; about 5.4 mM calcium chloride dihydrate, and about 0.013% (w/v) of polysorbate 20 or polysorbate 80. The disclosure further provides a pharmaceutical composition comprising: about 667 IU/ml of a FVIII polypeptide (e.g., a long-acting or short-acting FVIII polypeptide, e.g., rFVIIIFc); about 1.33% (w/v) of sucrose; about 205 mM NaCl; about 6.64 mM L-histidine; about 5.4 mM calcium chloride dihydrate, and about 0.013% (w/v) of polysorbate 20 or polysorbate 80. The disclosure further provides a pharmaceutical composition comprising: about 1000 IU/ml of a FVIII polypeptide (e.g., a long-acting or short-acting FVIII polypeptide, e.g., rFVIIIFc); about 1.33% (w/v) of sucrose; about 205 mM NaCl; about 6.64 mM L-histidine; about 5.4 mM calcium chloride, and about 0.013% (w/v) of polysorbate 20 or polysorbate 80. The disclosure also provides a pharmaceutical composition comprising: about 1333 IU/ml of a FVIII polypeptide (e.g., a long-acting or short-acting FVIII polypeptide, e.g., rFVIIIFc); about 1.33% (w/v) of sucrose; about 205 mM NaCl; about 6.64 mM L-histidine; about 5.4 mM calcium chloride, and about 0.013% (w/v) of polysorbate 20 or polysorbate 80. In some embodiments, the disclosure provides a pharmaceutical composition comprising: about 1667 IU/ml of a FVIII polypeptide (e.g., a long-acting or short-acting FVIII polypeptide, e.g., rFVIIIFc); about 1.33% (w/v) of sucrose; about 205 mM NaCl; about 6.64 mM L-histidine; about 5.4 mM calcium chloride, and about 0.013% (w/v) of polysorbate 20 or polysorbate 80. In other embodiments, the disclosure provides a pharmaceutical composition comprising: about 2000 IU/ml of a FVIII polypeptide (e.g., a long-acting or short-acting FVIII polypeptide, e.g., rFVIIIFc); about 1.33% (w/v) of sucrose; about 205 mM NaCl; about 6.64 mM L-histidine; about 5.4 mM calcium chloride, and about 0.013% (w/v) of polysorbate 20 or polysorbate 80.

The disclosure further provides a pharmaceutical composition comprising: about 83 IU/ml of a FVIII polypeptide (e.g., a long-acting or short-acting FVIII polypeptide, e.g., rFVIIIFc); about 13.3 mg/ml of sucrose; about 12.0 mg/ml NaCl; about 1.03 mg/ml L-histidine; about 0.80 mg/ml calcium chloride dihydrate, and about 0.10 mg/ml of polysorbate 20 or polysorbate 80. The disclosure further provides a pharmaceutical composition comprising: about 1673 IU/ml of a FVIII polypeptide (e.g., a long-acting or short-acting FVIII polypeptide, e.g., rFVIIIFc); about 13.3 mg/ml of sucrose; about 12.0 mg/ml NaCl; about 1.03 mg/ml L-histidine; about 0.80 mg/ml calcium chloride dihydrate, and about 0.10 mg/ml of polysorbate 20 or polysorbate 80. The disclosure further provides a pharmaceutical composition comprising: about 250 IU/ml of a FVIII polypeptide (e.g., a long-acting or short-acting FVIII polypeptide, e.g., rFVIIIFc); about 13.3 mg/ml of sucrose; about 12.0 mg/ml NaCl; about 1.03 mg/ml L-histidine; about 0.80 mg/ml calcium chloride dihydrate, and about 0.10 mg/ml of polysorbate 20 or polysorbate 80. The disclosure further provides a pharmaceutical composition comprising: about 333 IU/ml of a FVIII polypeptide (e.g., a long-acting or short-acting FVIII polypeptide, e.g., rFVIIIFc); about 13.3 mg/ml of sucrose; about 12.0 mg/ml NaCl; about 1.03 mg/ml L-histidine; about 0.80 mg/ml calcium chloride dihydrate, and about 0.10 mg/ml of polysorbate 20 or polysorbate 80. The disclosure further provides a pharmaceutical composition comprising: about 500 IU/ml of a FVIII polypeptide (e.g., a long-acting or short-acting FVIII polypeptide, e.g., rFVIIIFc); about 13.3 mg/ml of sucrose; about 12.0 mg/ml NaCl; about 1.03 mg/ml L-histidine; about 0.80 mg/ml calcium chloride dihydrate, and about 0.10 mg/ml of polysorbate 20 or polysorbate 80. The disclosure further provides a pharmaceutical composition comprising: about 667 IU/ml of a FVIII polypeptide (e.g., a long-acting or short-acting FVIII polypeptide, e.g., rFVIIIFc); about 13.3 mg/ml of sucrose;

about 12.0 mg/ml NaCl; about 1.03 mg/ml L-histidine; about 0.80 mg/ml calcium chloride dihydrate, and about 0.10 mg/ml of polysorbate 20 or polysorbate 80. The disclosure further provides a pharmaceutical composition comprising: about 1000 IU/ml of a FVIII polypeptide (e.g., a long-acting or short-acting FVIII polypeptide, e.g., rFVIIIFc); about 13.3 mg/ml of sucrose; about 12.0 mg/ml NaCl; about 1.03 mg/ml L-histidine; about 0.80 mg/ml calcium chloride dihydrate, and about 0.10 mg/ml of polysorbate 20 or polysorbate 80. The disclosure also provides a pharmaceutical composition comprising: about 1333 IU/ml of a FVIII polypeptide (e.g., a long-acting or short-acting FVIII polypeptide, e.g., rFVIIIFc); about 13.3 mg/ml of sucrose; about 12.0 mg/ml NaCl; about 1.03 mg/ml L-histidine; about 0.80 mg/ml calcium chloride dihydrate, and about 0.10 mg/ml of polysorbate 20 or polysorbate 80. In some embodiments, the disclosure provides a pharmaceutical composition comprising: about 1667 IU/ml of a FVIII polypeptide (e.g., a long-acting or short-acting FVIII polypeptide, e.g., rFVIIIFc); about 13.3 mg/ml of sucrose; about 12.0 mg/ml NaCl; about 1.03 mg/ml L-histidine; about 0.80 mg/ml calcium chloride dihydrate, and about 0.10 mg/ml of polysorbate 20 or polysorbate 80. In other embodiments, the disclosure provides a pharmaceutical composition comprising: about 2000 IU/ml of a FVIII polypeptide (e.g., a long-acting or short-acting FVIII polypeptide, e.g., rFVIIIFc); about 13.3 mg/ml of sucrose; about 12.0 mg/ml NaCl; about 1.03 mg/ml L-histidine; about 0.80 mg/ml calcium chloride dihydrate, and about 0.10 mg/ml of polysorbate 20 or polysorbate 80.

This disclosure also provides the components of a pharmaceutical kit. Such a kit includes one or more containers and optional attachments. A kit as provided herein facilitates administration of an effective amount of the FVIII polypeptide (e.g., a long-acting or short-acting FVIII polypeptide, e.g., rFVIIIFc) to a subject in need thereof. In certain embodiments, the kit facilitates administration of the FVIII polypeptide (e.g., a long-acting or short-acting FVIII polypeptide, e.g., rFVIIIFc) via intravenous infusion. In certain embodiments, the kit facilitates self-administration of the FVIII polypeptide (e.g., a long-acting or short-acting FVIII polypeptide, e.g., rFVIIIFc) via intravenous infusion.

In certain embodiments, the disclosure provides a pharmaceutical kit comprising: a first container comprising a lyophilized powder or cake, where the powder or cake comprises: (i) a FVIII polypeptide (e.g., a long-acting or short-acting FVIII polypeptide, e.g., rFVIIIFc), (ii) sucrose (and/or trehalose, raffinose or arginine); (iii) NaCl; (iv) L-histidine; (v) calcium chloride dihydrate; and (vi) polysorbate 20 or polysorbate 80; and a second container comprising sterilized water for injections to be combined with the lyophilized powder of the first container. In certain embodiments, sufficient diluent is provided to produce about 3 ml of a FVIII polypeptide (e.g., a long-acting or short-acting FVIII polypeptide, e.g., rFVIIIFc) formulation with desired properties as disclosed herein. In certain embodiments, the second container is a pre-filled syringe associated with a plunger, to allow addition of the diluent to the first container, reconstitution of the contents of the first container, and transfer back into the syringe. In certain embodiments, the kit further provides an adaptor for attaching the syringe to the first container. In certain embodiments the kit further provides a needle and infusion tubing, to be attached to the syringe containing the reconstituted FVIII polypeptide (e.g., a long-acting or short-acting FVIII polypeptide, e.g., rFVIIIFc) formulation to allow IV infusion of the formulation.

In certain embodiments a FVIII polypeptide (e.g., a long-acting or short-acting FVIII polypeptide, e.g., rFVIIIFc) is provided in a total amount from about 200 IU to about 6000 IU, e.g., about 250 IU, about 500 IU, about 750 IU, about 1000 IU, about 1500 IU, about 2000 IU, about 3000 IU, about 4000 IU, about 5000 IU, or about 6000 IU.

In one embodiment, a pharmaceutical kit is provided which comprises a first container comprising a lyophilized powder, where the powder comprises (i) about 250 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 83 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 500 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 167 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 750 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 250 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 1000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 333 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 1500 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 500 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 2000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 667 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 3000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 1000 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 4000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 1333 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 5000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 1667 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 6000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 2000 IU/ml of a FVIII polypeptide (e.g., a long-acting or short-acting FVIII polypeptide, e.g., rFVIIIFc); (ii) about 1.33% (w/v) of sucrose; (iii) about 205 mM of NaCl; (iv) about 6.64 mM L-histidine; (v) about 5.4 mM of calcium chloride; and (vi) about 0.013% (w/v) of polysorbate 20 or polysorbate 80.

In a further embodiment, a pharmaceutical kit is provided which comprises a first container comprising a lyophilized powder, where the powder comprises: (i) about 250 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 83 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In a further embodiment, a pharmaceutical kit is provided which comprises a first container comprising a lyophilized powder, where the powder comprises: (i) about 500 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 167 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In a further embodiment, a pharmaceutical kit is provided which comprises a first container comprising a lyophilized powder, where the powder comprises: (i) about 750 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 250 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In a further embodiment, a pharmaceutical kit is provided which comprises a first container comprising a lyophilized powder, where the powder comprises: (i) about 1000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 333 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In a further embodiment, a pharmaceutical kit is provided which comprises a first container comprising a lyophilized powder, where the powder comprises: (i) about 1500 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 500 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In a further embodiment, a pharmaceutical kit is provided which comprises a first container comprising a lyophilized powder, where the powder comprises: (i) about 2000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 667 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In a further embodiment, a pharmaceutical kit is provided which comprises a first container comprising a lyophilized powder, where the powder comprises: (i) about 3000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 1000 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In a further embodiment, a pharmaceutical kit is provided which comprises a first container comprising a lyophilized powder, where the powder comprises: (i) about 4000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 1333 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In a further embodiment, a pharmaceutical kit is provided which comprises a first container comprising a lyophilized powder, where the powder comprises: (i) about 5000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v) about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 1667 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In a further embodiment, a pharmaceutical kit is provided which comprises a first container comprising a lyophilized powder, where the powder comprises: (i) about 6000 IU of a FVIII polypeptide (e.g., a long-acting or short-acting FVIII polypeptide, e.g., rFVIIIFc), (ii) about 40 mg of sucrose; (iii) about 36 mg of NaCl; (iv) about 3.1 mg of L-histidine; (v)

about 2.4 mg of calcium chloride dihydrate; and (vi) about 0.40 mg of polysorbate 20 or polysorbate 80; and a second container comprising sterilized water for injections at a volume sufficient to produce, when combined with the lyophilized powder of the first container, a solution comprising: (i) about 2000 IU/ml of a FVIII polypeptide (e.g., a long-acting or short-acting FVIII polypeptide, e.g., rFVIIIFc); (ii) about 13.3 mg/ml of sucrose; (iii) about 12.0 mg/ml of NaCl; (iv) about 1.03 mg/ml L-histidine; (v) about 0.80 mg/ml of calcium chloride dihydrate; and (vi) about 0.13 mg/ml of polysorbate 20 or polysorbate 80.

In certain embodiments the first container of a pharmaceutical kit provided herein is a glass vial comprising a rubber stopper. In certain embodiments, the second container a pharmaceutical kit provided herein is a syringe body, associated with a plunger. In certain embodiments, the syringe is a pre-filled syringe containing the diluent. In certain embodiments, a pharmaceutical kit provided herein further comprises an adaptor to connect the glass vial to the syringe body. In certain embodiments a pharmaceutical kit provided herein further comprises infusion tubing associated with a needle to be connected to the syringe, suitable for intravenous infusion.

In certain embodiments, a desired dose of a FVIII polypeptide (e.g., a long-acting or short-acting FVIII polypeptide, e.g., rFVIIIFc) can be achieved through the use of one pharmaceutical kit as provided herein. In certain embodiments, more than one pharmaceutical kit can be used to achieve a desired dose. Provided herein is a method of combining, or pooling the formulations contained in two or more pharmaceutical kits as provided herein in order to achieve a desired dose.

In some embodiments, the FVIII polypeptide for the pharmaceutical composition is a short-acting FVIII polypeptide. In other embodiments, the FVIII polypeptide for the pharmaceutical composition is a long-acting FVIII polypeptide.

In some embodiments, a long-acting FVIII polypeptide in a pharmaceutical composition comprises a Factor VIII portion and a non-Factor VIII portion, e.g., a heterologous moiety. In one embodiment, the heterologous moiety is capable of extending in vivo or in vitro half-life of the FVIII polypeptide. Exemplary non-Factor VIII portions include, but are not limited to, Fc, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, albumin-binding small molecules, or any combination thereof. Exemplary long-acting polypeptides of the invention include, e.g., Factor VIII-Fc polypeptides, Factor VIII-albumin polypeptides, Factor VIII-PAS polypeptides, Factor VIII-transferrin polypeptides, Factor VIII-CTP polypeptides, Factor VIII-PEG polypeptides, Factor VIII-HES polypeptides, Factor VIII-albumin binding polypeptide polypeptides, or Factor VIII-albumin-binding small molecule polypeptides.

The Factor VIII (the Factor VIII portion of a long-acting FVIII polypeptide or FVIII of a short-acting FVIII polypeptide) can be at least 60%, 70%, 80%, 90%, 95%, 96%, 97%, 98%, 99%, or 100% identical to a Factor VIII amino acid sequence shown in Table 11 without a signal sequence (amino acids 20 to 1457 of SEQ ID NO:2; and amino acids 20 to 2351 of SEQ ID NO:6), wherein the Factor VIII portion has Factor VIII activity. The Factor VIII (the Factor VIII portion of a chimeric polypeptide) can be identical to a Factor VIII amino acid sequence shown in Table 11 without a signal sequence (amino acids 20 to 1457 of SEQ ID NO:2; and amino acids 20 to 2351 of SEQ ID NO:6).

The Factor VIII (the Factor VIII portion of a long-acting FVIII polypeptide or FVIII of a short-acting FVIII polypeptide) can be at least 60%, 70%, 80%, 90%, 95%, 96%, 97%, 98%, 99%, or 100% identical to a Factor VIII amino acid sequence shown in Table 11 with a signal sequence (amino acids 1 to 1457 of SEQ ID NO:2 and amino acids 1 to 2351 of SEQ ID NO:6), wherein the Factor VIII portion has Factor VIII activity. The Factor VIII (the Factor VIII portion of a long-acting FVIII polypeptide or a short-acting FVIII polypeptide) can be identical to a Factor VIII amino acid sequence shown in Table 11 with a signal sequence (amino acids 1 to 1457 of SEQ ID NO:2 and amino acids 1 to 2351 of SEQ ID NO:6).

The long-acting polypeptide can comprise a sequence at least 60%, 70%, 80%, 90%, 95%, 96%, 97%, 98%, 99%, or 100% identical to the Factor VIII and Fc amino acid sequence shown in Table 11A(i) without a signal sequence (amino acids 20 to 1684 of SEQ ID NO:2) or at least 60%, 70%, 80%, 90%, 95%, 96%, 97%, 98%, 99%, or 100% identical to the Factor VIII and Fc amino acid sequence shown in Table 11A(i) with a signal sequence (amino acids 1 to 1684 of SEQ ID NO:2), wherein the sequence has Factor VIII activity. The Factor VIII activity can be measured by activated Partial Thromboplastin Time (aPTT) assay, chromogenic assay, or other known methods. The long-acting FVIII polypeptide can comprise the sequence identical to the Factor VIII and Fc amino acid sequence shown in Table 11A(i) without a signal sequence (amino acids 20 to 1684 of SEQ ID NO:2) or identical to the Factor VIII and Fc amino acid sequence shown in Table 11A(i) with a signal sequence (amino acids 1 to 1684 of SEQ ID NO:2).

As discussed above, exemplary long-acting polypeptides also include Factor VIII fused to one or more albumin polypeptides, albumin binding polypeptides, or albumin-binding small molecules. In one embodiment, the albumin is human albumin. The albumin or albumin binding protein can be fused to either the N-terminal end of FVIII or to the C-terminal end of FVIII or inserted between two amino acids in FVIII. Examples of albumin, e.g., fragments thereof that can be used in the present invention are known. e.g., U.S. Pat. No. 7,592,010; U.S. Pat. No. 6,686,179; and Schulte, *Thrombosis Res.* 124 Suppl. 2:S6-S8 (2009), each of which is incorporated herein by reference in its entirety.

The albumin binding polypeptides can compromise, without limitation, bacterial albumin-binding domains, albumin-binding peptides, or albumin-binding antibody fragments that can bind to albumin. Domain 3 from streptococcal protein G, as disclosed by Kraulis et al., *FEBS Lett.* 378: 190-194 (1996) and Linhult et al., *Protein Sci.* 11:206-213 (2002) is an example of a bacterial albumin-binding domain. Examples of albumin-binding peptides include a series of peptides having the core sequence DICLPRWGCLW (SEQ ID NO: 7). See, e.g., Dennis et al., *J. Biol. Chem.* 2002, 277: 35035-35043 (2002). Examples of albumin-binding antibody fragments are disclosed in Muller and Kontermann, *Curr. Opin. Mol. Ther.* 9:319-326 (2007); Rooverset et al., *Cancer Immunol. Immunother.* 56:303-317 (2007), and Holt et al., *Prot. Eng. Design Sci.,* 21:283-288 (2008), which are incorporated herein by reference in their entireties.

In certain aspects, a long-acting FVIII polypeptide of the invention comprises at least one attachment site for a non-polypeptide small molecule, variant, or derivative that can bind to albumin thereof. An example of such albumin binding moieties is 2-(3-maleimidopropanamido)-6-(4-(4- iodophenyl)butanamido)hexanoate ("Albu" tag) as disclosed by Trusselet et al., *Bioconjugate Chem.* 20:2286-2292 (2009).

As discussed above, exemplary long-acting polypeptides also include Factor VIII fused to at least one C-terminal peptide (CTP) of the β subunit of human chorionic gonadotropin or fragment, variant, or derivative thereof. The CTP can be fused to Factor VIII either the N-terminal end of FVIII or to the C-terminal end of FVIII or inserted between two amino acids in FVIII. One or more CTP peptides fused to or inserted into a recombinant protein is known to increase the in vivo half-life of that protein. See, e.g., U.S. Pat. No. 5,712,122, incorporated by reference herein in its entirety. Exemplary CTP peptides include DPRFQDSSSSKAPPPSLPSPSRLPGPSDTPIL (SEQ ID NO: 8) or SSSSKAPPPSLPSPSRLPGPSDTPILPQ. (SEQ ID NO: 9). See, e.g., U.S. Patent Application Publication No. US 2009/0087411 A1, incorporated by reference.

As discussed above, exemplary long-acting FVIII polypeptides also include Factor VIII fused to at least one PAS sequence or fragment, variant, or derivative thereof. The PAS sequence can be fused to either the N-terminal end of FVIII or to the C-terminal end of FVIII or inserted between two amino acids in FVIII. A PAS peptide or PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. An amino acid polymer also can form random coil conformation when residues other than alanine, serine, and proline are added as a minor constituent in the PAS sequence. By "minor constituent" is meant that that amino acids other than alanine, serine, and proline can be added in the PAS sequence to a certain degree, e.g., up to about 12%, i.e., about 12 of 100 amino acids of the PAS sequence, up to about 10%, up to about 9%, up to about 8%, about 6%, about 5%, about 4%, about 3%, i.e. about 2%, or about 1%, of the amino acids. The amino acids different from alanine, serine and proline can be selected from the group consisting of Arg, Asn, Asp, Cys, Gln, Glu, Gly, His, Ile, Leu, Lys, Met, Phe, Thr, Trp, Tyr, and Val. Under physiological conditions, a PAS peptide forms a random coil conformation and thereby can mediate an increased in vivo and/or in vitro stability to a recombinant protein of the invention, and has procoagulant activity.

Non-limiting examples of the PAS peptides include ASPAAPAPASPAAPAPSAPA (SEQ ID NO: 10), AAPASPAPAAPSAPAPAAPS (SEQ ID NO: 11), APSSPSPSAPSSPSPASPSS (SEQ ID NO: 12), APSSPSPSAPSSPSPASPS (SEQ ID NO: 13), SSPSAPSPSSPASPSPSSPA (SEQ ID NO: 14), AASPAAPSAPPAAASPAAPSAPPA (SEQ ID NO: 15), ASAAAPAAASAAASAPSAAA (SEQ ID NO: 16) or any variants, derivatives, fragments, or combinations thereof. Additional examples of PAS sequences are known from, e.g., US Pat. Publ. No. 2010/0292130 A1 and PCT Appl. Publ. No. WO 2008/155134 A1. European issued patent EP2173890.

As discussed above, exemplary long-acting FVIII polypeptides also include Factor VIII fused to at least one transferrin peptide or fragment, variant, or derivative thereof. At least one transferrin peptide can be fused to either the N-terminal end of FVIII or to the C-terminal end of FVIII or inserted between two amino acids in FVIII. Any transferrin can be fused to or inserted into a recombinant FVIII protein of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov), all of which are herein incorporated by reference in their entirety.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., *Trends Pharmacol. Sci.* 23:206-209 (2002)). Transferrin fusion proteins have been studied for half-life extension, targeted deliver for cancer therapies, oral delivery and sustained activation of proinsulin (Brandsma et al., *Biotechnol. Adv.*, 29: 230-238 (2011); Bai et al., *Proc. Natl. Acad Sci. USA* 102:7292-7296 (2005); Kim et al., *J. Pharmacol. Exp. Ther.*, 334:682-692 (2010); Wang et al., *J. Controlled Release* 155:386-392 (2011)).

As discussed above, exemplary long-acting FVIII polypeptides also include Factor VIII fused to at least one polyethylene glycol (PEG) moieties.

PEGylated FVIII can refer to a conjugate formed between FVIII and at least one polyethylene glycol (PEG) molecule. PEG is commercially available in a large variety of molecular weights and average molecular weight ranges. Typical examples of PEG average molecular weight ranges include, but are not limited to, about 200, about 300, about 400, about 600, about 1000, about 1300-1600, about 1450, about 2000, about 3000, about 3000-3750, about 3350, about 3000-7000, about 3500-4500, about 5000-7000, about 7000-9000, about 8000, about 8000, about 10000, about 8500-11500, about 16000-24000, about 35000, about 40000, about 60000, and about 80000 daltons. These average molecular weights are provided merely as examples and are not meant to be limiting in any way.

A long-acting FVIII polypeptide useful for the invention can be PEGylated to include mono- or poly- (e.g., 2-4) PEG moieties. PEGylation can be carried out by any of the PEGylation reactions known in the art. Methods for preparing a PEGylated protein product will generally include (i) reacting a polypeptide with polyethylene glycol (such as a reactive ester or aldehyde derivative of PEG) under conditions whereby the peptide of the invention becomes attached to one or more PEG groups; and (ii) obtaining the reaction product(s). In general, the optimal reaction conditions for the reactions will be determined case by case based on known parameters and the desired result.

There are a number of PEG attachment methods available to those skilled in the art, for example Malik F et al., *Exp. Hematol.* 20:1028-35 (1992); Francis, *Focus on Growth Factors* 3(2):4-10 (1992); European Pat. Pub. Nos. EP0401384, EP0154316, and EP0401384; and International Pat. Appl. Pub. Nos. WO92/16221 and WO95/34326. As a non-limiting example, FVIII variants can contain cysteine substitutions in one or more insertion sites in FVIII, and the cysteines can be further conjugated to PEG polymer. See Mei et al., *Blood* 116:270-279 (2010) and U.S. Pat. No. 7,632,921, which are incorporated herein by reference in their entireties.

As discussed above, exemplary long-acting FVIII polypeptides also include Factor VIII fused to at least one hydroxyethyl starch (HES) polymer. HES is a derivative of naturally occurring amylopectin and is degraded by alpha-amylase in the body. HES exhibits advantageous biological properties and is used as a blood volume replacement agent and in hemodilution therapy in the clinics. See, e.g., Sommermeyer et al., *Krankenhauspharmazie* 8:271-278 (1987); and Weidler et al., *Arzneim.-Forschung/Drug Res.* 41: 494-498 (1991).

HES is mainly characterized by the molecular weight distribution and the degree of substitution. HES has a mean molecular weight (weight mean) of from 1 to 300 kD, from 2 to 200 kD, from 3 to 100 kD, or from 4 to 70 kD. Hydroxyethyl starch can further exhibit a molar degree of substitution of from 0.1 to 3, from 0.1 to 2, from 0.1 to 0.9, or from 0.1 to 0.8, and a ratio between C2:C6 substitution in the range of from 2 to 20 with respect to the hydroxyethyl groups. HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. There are a number of HES attachment methods available to those skilled in the art, e.g., the same PEG attachment methods described above.

In some embodiments, a long-acting FVIII polypeptide comprising a FVIII portion has an increased half-life ($t_{1/2}$) over a polypeptide consisting of the same FVIII portion without the non-FVIII portion. A long-acting FVIII polypeptide with an increased $t_{1/2}$ can be referred to herein as a long-lasting FVIII. Long-acting chimeric Factor VIII polypeptides include, e.g., Factor VIII fused to Fc (including, e.g., chimeric Factor VIII polypeptides in the form of a hybrid such as a FVIIIFc monomer dimer hybrid; see Example, Table 11A; and U.S. Pat. Nos. 7,404,956 and 7,348,004), and Factor VIII fused to albumin.

The Factor VIII polypeptide as used herein is functional factor VIII polypeptide in its normal role in coagulation, unless otherwise specified. Thus, the term Factor VIII includes variant polypeptides that are functional. Factor VIII proteins can be the human, porcine, canine, and murine factor VIII proteins. The full length polypeptide and polynucleotide sequences are known, as are many functional fragments, mutants and modified versions. Examples of human factor VIII sequences are shown as subsequences in SEQ ID NOs: 2 or 6 (Table 11). Factor VIII polypeptides include, e.g., full-length factor VIII, full-length factor VIII minus Met at the N-terminus, mature factor VIII (minus the signal sequence), mature factor VIII with an additional Met at the N-terminus, and/or factor VIII with a full or partial deletion of the B domain. Factor VIII variants include B domain deletions, whether partial or full deletions.

A great many functional factor VIII variants are known, as is discussed above and below. In addition, hundreds of nonfunctional mutations in factor VIII have been identified in hemophilia patients, and it has been determined that the effect of these mutations on factor VIII function is due more to where they lie within the 3-dimensional structure of factor VIII than on the nature of the substitution (Cutler et al., *Hum. Mutat.* 19:274-8 (2002)), incorporated herein by reference in its entirety. In addition, comparisons between factor VIII from humans and other species have identified conserved residues that are likely to be required for function (Cameron et al., *Thromb. Haemost.* 79:317-22 (1998); U.S. Pat. No. 6,251,632), incorporated herein by reference in its entirety.

The human factor VIII gene was isolated and expressed in mammalian cells (Toole, J. J., et al., *Nature* 312:342-347 (1984); Gitschier, J., et al., *Nature* 312:326-330 (1984); Wood, W. I., et al., *Nature* 312:330-337 (1984); Vehar, G. A., et al., *Nature* 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, discloses a recombinant DNA method for producing factor VIII in mammalian host cells and purification of human factor VIII. Human factor VIII expression in CHO (Chinese hamster ovary) cells and BHK (baby hamster kidney cells) has been reported. Human factor VIII has been modified to delete part or all of the B domain (U.S. Pat. Nos. 4,994,371 and 4,868,112, each of which is incorporated herein by reference in its entirety), and replacement of the human factor VIII B domain with the human factor V B domain has been performed (U.S. Pat. No. 5,004,803, incorporated herein by reference in its entirety). The cDNA sequence encoding human factor VIII and predicted amino acid sequence are shown in SEQ ID NOs:1 and 2, respectively, of US Application Publ. No. 2005/0100990, incorporated herein by reference in its entirety.

U.S. Pat. No. 5,859,204, Lollar, J. S., incorporated herein by reference in its entirety, reports functional mutants of factor VIII having reduced antigenicity and reduced immunoreactivity. U.S. Pat. No. 6,376,463, Lollar, J. S., incorporated herein by reference in its entirety, also reports mutants of factor VIII having reduced immunoreactivity. US Application Publ. No. 2005/0100990, Saenko et al., incorporated herein by reference in its entirety, reports functional mutations in the A2 domain of factor VIII.

A number of functional factor VIII molecules, including B-domain deletions, are disclosed in the following patents U.S. Pat. No. 6,316,226 and U.S. Pat. No. 6,346,513, both assigned to Baxter; U.S. Pat. No. 7,041,635 assigned to In2Gen; U.S. Pat. No. 5,789,203, U.S. Pat. No. 6,060,447, U.S. Pat. No. 5,595,886, and U.S. Pat. No. 6,228,620 assigned to Chiron; U.S. Pat. No. 5,972,885 and U.S. Pat. No. 6,048,720 assigned to Biovitrum, U.S. Pat. No. 5,543, 502 and U.S. Pat. No. 5,610,278 assigned to Novo Nordisk; U.S. Pat. No. 5,171,844 assigned to Immuno Ag; U.S. Pat. No. 5,112,950 assigned to Transgene S.A.; U.S. Pat. No. 4,868,112 assigned to Genetics Institute, each of which is incorporated herein by reference in its entirety.

The porcine factor VIII sequence is published, (Toole, J. J., et al., *Proc. Natl. Acad. Sci. USA* 83:5939-5942 (1986)), incorporated herein by reference in its entirety, and the complete porcine cDNA sequence obtained from PCR amplification of factor VIII sequences from a pig spleen cDNA library has been reported (Healey, J. F. et al., *Blood* 88:4209-4214 (1996), incorporated herein by reference in its entirety). Hybrid human/porcine factor VIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat.

No. 6,458,563, incorporated herein by reference in its entirety assigned to Emory discloses a B-domain deleted porcine Factor VIII.

A "B domain" of Factor VIII, as used herein, is the same as the B domain known in the art that is defined by internal amino acid sequence identity and sites of proteolytic cleavage by thrombin, e.g., residues Ser741-Arg1648 of full length mature human factor VIII. The other human factor VIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. The locations of the boundaries for all of the domains, including the B domains, for porcine, mouse and canine factor VIII are also known in the art. In one embodiment, the B domain of Factor VIII is deleted ("B domain deleted factor VIII" or "BDD FVIII"). An example of a BDD FVIII is REFACTO® (recombinant BDD FVIII), which has the sequence as the Factor VIII portion of the sequence in Table 11A(i) (amino acids 1 to 1457 or 20 to 1457 of SEQ ID NO:2). In another embodiment, the B domain deleted Factor VIII contains an intact intracellular processing site, which corresponds to Arginine at residue 754 of B domain deleted Factor VIII, which corresponds to Arginine residue 773 of SEQ ID NO: 2, or residue 1648 of full-length Factor VIII, which corresponds to Arginine residue 1667 of SEQ ID NO: 6. The sequence residue numbers used herein without referring to any SEQ ID Numbers correspond to the Factor VIII sequence without the signal peptide sequence (19 amino acids) unless otherwise indicated. For example, S743/Q1638 of full-length Factor VIII corresponds to S762/Q1657 of SEQ ID NO: 6 due to the 19 amino acid signal peptide sequence. In other embodiments, the B domain deleted FVIII comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In some embodiments, the amino acid substituted at the amino acid position corresponding to Arginine 1645 is a different amino acid from the amino acid substituted at the amino acid position corresponding to Arginine 1648. In certain embodiments, the substitution or mutation is an amino acid other than arginine, e.g., alanine.

A "B domain deleted factor VIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted factor VIII of the present invention has a deletion disclosed at col. 2, lines 26-51 and examples 5-8 of U.S. Pat. No. 5,789,203 (also U.S. Pat. No. 6,060,447, U.S. Pat. No. 5,595,886, and U.S. Pat. No. 6,228,620). In some embodiments, a B domain deleted factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and Table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted factor VIII has a deletion of most of the B domain, but still contains amino-terminal sequences of the B domain that are essential for in vivo proteolytic processing of the primary translation product into two polypeptide chain (i.e., intracellular processing site), as disclosed in WO 91/09122, which is incorporated herein by reference in its entirety. In some embodiments, a B domain deleted factor VIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A B domain deleted factor VIII can also contain a deletion of amino acids 771-1666 or amino acids 868-1562 of factor VIII. Meulien P., et al. *Protein Eng.* 2(4): 301-6 (1988), incorporated herein by reference in its entirety. Additional B domain deletions that are part of the invention include, e.g., deletion of amino acids 982 through 1562 or 760 through 1639 (Toole et al., *Proc. Natl. Acad. Sci. U.S.A.* 83:5939-5942 (1986)), 797 through 1562 (Eaton et al., *Biochemistry* 25:8343-8347 (1986)), 741 through 1646 (Kaufman (PCT published application No. WO 87/04187)), 747-1560 (Sarver et al., *DNA* 6:553-564 (1987)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. In some embodiments, B domain deleted FVIII comprises a partial deletion in B domain, i.e., having 21 amino acids from B domain (i.e., SFSQNSRHPSQNPPVLKRHQR, which is SEQ ID NO: 17) disclosed in US Publication No. 20100286067 and US Publication No. US 20120093840, both of which are incorporated herein by reference in their entireties. Each of the foregoing deletions can be made in any Factor VIII sequence.

In one embodiment, the B domain deleted Factor VIII portion in a FVIII polypeptide is processed into two chains connected (or associated) by a metal bond, the first chain comprising a heavy chain (A1-A2-partial B) and a second chain comprising a light chain (A3-C1-C2). In another embodiment, the B domain deleted Factor VIII portion is a single chain Factor VIII. The single chain Factor VIII can comprise an intracellular processing site, which corresponds to Arginine at residue 754 of B domain deleted Factor VIII (residue 773 of SEQ ID NO: 2) or at residue 1648 of full-length Factor VIII (residue 1657 of SEQ ID NO: 6).

The metal bond between the heavy chain and the light chain can be any metal known in the art. For example, the metals useful for the invention can be a divalent metal ion. The metals that can be used to associate the heavy chain and light chain include, but not limited to, $Ca^{2+}$, $Mn^{2+}$, or $Cu^{2+}$. Fatouros et al., *Intern. J. Pharm.* 155(1): 121-131 (1997); Wakabayashi et al., *JBC.* 279(13): 12677-12684 (2004).

A FVIII polypeptide used herein can comprise processed Factor VIII or single chain Factor VIII or a combination thereof. "Processed Factor VIII," as used herein means Factor VIII that has been cleaved at Arginine 1648 (for full-length Factor VIII) or Arginine 754 (for B-domain deleted Factor VIII), i.e., intracellular processing site. Due to the cleavage at the intracellular processing site, processed Factor VIII comprises two polypeptide chains, the first chain being a heavy chain and the second chain being a light chain. For example, the processed Factor VIII-Fc fusion protein (i.e., Heavy chain and Light chain fused to Fc) run at approximately 90 kDa and 130 kDa on a non-reducing SDS-PAGE, respectively, and 90 kDa and 105 kDa on a reducing SDS-PAGE, respectively. Therefore, in one embodiment, at least about 50%, about 60%, about 70%, about 75%, about 80%, about 85%, about 90%, about 95%, about 96%, about 97%, about 98%, about 99%, or about 100% of the Factor VIII portion in the long-acting polypeptide or in the short-acting FVIII polypeptide is processed Factor VIII. In another embodiment, about 50%, about 60%, about 70%, about 75%, about 80%, about 85%, about 90%, about 95%, about 96%, about 97%, about 98%, about 99%, or about 100% of the Factor VIII portion in the long-acting polypeptide or in the short-acting FVIII polypeptide is processed Factor VIII. In a particular embodiment, the FVIII polypeptide comprising processed Factor VIII is purified (or isolated) from the polypeptide comprising single chain Factor VIII, and at least about 75%, about 80%, about 85%, about 90%, about 95%, about 96%, about 97%, about 98%, about 99%, or about 100% of the Factor VIII portion in the long-acting polypeptide or in the short-acting FVIII polypeptide is processed Factor VIII. In some embodiments, the FVIII polypeptide comprises about 15% to 25% of single chain FVIII polypeptide and about 75% to about 85% of processed FVIII polypeptide.

"Single chain Factor VIII," "SC Factor VIII," or "SCFVIII" as used herein means Factor VIII that has not been cleaved at the Arginine site (residue 1648 for full-length Factor VIII (i.e., residue 1667 of SEQ ID NO: 6) or residue 754 for B-domain deleted Factor VIII (i.e., residue 773 of SEQ ID NO: 2). Therefore, single chain Factor VIII in the FVIII polypeptide used herein comprises a single chain. In one embodiment, the single chain Factor VIII contains an intact intracellular processing site. In another embodiment, the single chain Factor VIII of the invention comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In other embodiments, the amino acid substituted at the amino acid position corresponding to Arginine 1645 is a different amino acid from the amino acid substituted at the amino acid position corresponding to Arginine 1648. In certain embodiments, the substitution or mutation is an amino acid other than arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine. The single chain Factor VIII-Fc fusion protein can run at approximately 220 kDa on a non reducing SDS-PAGE and at approximately 195 kDa on a reducing SDS-PAGE.

The Factor VIII portion in the FVIII polypeptide used herein has Factor VIII activity. Factor VIII activity can be measured by any known methods in the art. For example, one of those methods can be a chromogenic assay. The chromogenic assay mechanism is based on the principles of the blood coagulation cascade, where activated Factor VIII accelerates the conversion of Factor X into Factor Xa in the presence of activated Factor IX, phospholipids and calcium ions. The Factor Xa activity is assessed by hydrolysis of a p-nitroanilide (pNA) substrate specific to Factor Xa. The initial rate of release of p-nitroaniline measured at 405 nM is directly proportional to the Factor Xa activity and thus to the Factor VIII activity in the sample. The chromogenic assay is recommended by the Factor VIII and Factor IX Subcommittee of the Scientific and Standardization Committee (SSC) of the International Society on Thrombosis and Hemostasis (ISTH). Since 1994, the chromogenic assay has also been the reference method of the European Pharmacopoeia for the assignment of FVIII concentrate potency. Thus, in one embodiment, the FVIII polypeptide comprising single chain Factor VIII has Factor VIII activity comparable to a FVIII polypeptide comprising processed Factor VIII, when the Factor VIII activity is measured in vitro by a chromogenic assay.

In certain embodiment, a long-acting FVIII polypeptide is a FVIII monomer-dimer hybrid. To obtain a FVIII monomer-dimer hybrid, the coding sequence of human recombinant B-domain deleted FVIII was obtained by reverse transcription-polymerase chain reaction (RT-PCR) from human liver poly A RNA (Clontech) using FVIII-specific primers. The FVIII sequence includes the native signal sequence for FVIII. The B-domain deletion was from serine 743 (S743; 2287 bp) to glutamine 1638 (Q1638; 4969 bp) for a total deletion of 2682 bp. Then, the coding sequence for human recombinant Fc was obtained by RT-PCR from a human leukocyte cDNA library (Clontech) using Fc specific primers. Primers were designed such that the B-domain deleted FVIII sequence was fused directly to the N-terminus of the Fc sequence with no intervening linker. The FVIIIFc DNA sequence was cloned into the mammalian dual expression vector pBUDCE4.1 (Invitrogen) under control of the CMV promoter. A second identical Fc sequence including the mouse Igκ signal sequence was obtained by RT-PCR and cloned downstream of the second promoter, EF1α, in the expression vector pBUDCE4.1.

In one embodiment, an FcRn binding partner can be an Fc region. An FcRn binding partner is any molecule that can be specifically bound by the FcRn receptor with consequent active transport by the FcRn receptor of the FcRn binding partner. Thus, the term Fc includes any variants of IgG Fc that are functional. The region of the Fc portion of IgG that binds to the FcRn receptor has been described based on X-ray crystallography (Burmeister et al., *Nature* 372:379 (1994), incorporated herein by reference in its entirety). The major contact area of the Fc with the FcRn is near the junction of the CH2 and CH3 domains. Fc-FcRn contacts are all within a single Ig heavy chain. The FcRn binding partners include, e.g., whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al., *J. Exp. Med.* 180: 2377 (1994), incorporated herein by reference in its entirety.) An Fc can comprise the CH2 and CH3 domains of an immunoglobulin with or without the hinge region of the immunoglobulin. Exemplary Fc variants are provided in WO 2004/101740 and WO 2006/074199, incorporated herein by reference in its entirety.

Fc (or Fc portion of a chimeric polypeptide) can contain one or more mutations, and combinations of mutations.

Fc (or Fc portion of a chimeric polypeptide) can contain mutations conferring increased half-life such as M252Y, S254T, T256E, and combinations thereof, as disclosed in Oganesyan et al., *Mol. Immunol.* 46:1750 (2009), which is incorporated herein by reference in its entirety; H433K, N434F, and combinations thereof, as disclosed in Vaccaro et al., *Nat. Biotechnol.* 23:1283 (2005), which is incorporated herein by reference in its entirety; the mutants disclosed at pages 1-2, paragraph [0012], and Examples 9 and 10 of US 2009/0264627 A1, which is incorporated herein by reference in its entirety; and the mutants disclosed at page 2, paragraphs [0014] to [0021] of US 20090163699 A1, which is incorporated herein by reference in its entirety.

Fc (or Fc portion of a chimeric polypeptide) can also include, e.g., the following mutations: The Fc region of IgG can be modified according to well recognized procedures such as site directed mutagenesis and the like to yield modified IgG or Fc fragments or portions thereof that will be bound by FcRn. Such modifications include, e.g., modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn. P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine other amino acids can be substituted for the wildtype amino acids at the positions specified above. Mutations can be introduced singly into Fc giving rise to more than one hundred FcRn binding partners distinct from native Fc. Additionally, combinations of two, three, or more of these individual mutations can be introduced together, giving rise to hundreds more FcRn binding partners. Certain of these mutations can confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety). Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII which mediate various effector functions will not bind to IgG1 when such mutations have been introduced (Ward and Ghetie, *Therapeutic Immunology* 2:77 (1995), which is incorporated herein by reference in its entirety; and Armour et al., *Eur. J. Immunol.* 29:2613 (1999), which is incorporated herein by reference in its entirety). As a further example of new functionality arising from mutations described above affinity for FcRn can be increased beyond that of wild type in some instances. This increased affinity can reflect an increased "on" rate, a decreased "off" rate or both an increased "on" rate and a decreased "off" rate. Mutations believed to impart an increased affinity for FcRn include, e.g., T256A, T307A, E380A, and N434A (Shields et al., *J. Biol. Chem.* 276:6591 (2001), which is incorporated herein by reference in its entirety).

The Fc (or Fc portion of a chimeric polypeptide) can be at least 60%, 70%, 80%, 90%, 95%, 96%, 97%, 98%, 99%, or 100% identical to the Fc amino acid sequence shown in Table 11 (amino acids 1458 to 1684 of SEQ ID NO:2 or amino acids 2352 to 2578 of SEQ ID NO:6). The Fc (or Fc portion of a chimeric polypeptide) can be identical to the Fc amino acid sequence shown in Table 11 (amino acids 1458 to 1684 of SEQ ID NO:2 and amino acids 2352 to 2578 of SEQ ID NO:6).

As a practical matter, whether any particular nucleic acid molecule or polypeptide is at least 85%, 90%, 95%, 96%, 97%, 98% or 99% identical to a nucleotide sequence or polypeptide of the present invention can be determined conventionally using known computer programs. In one embodiment, a method for determining the best overall match between a query sequence (reference or original sequence) and a subject sequence, also referred to as a global sequence alignment, can be determined using the FASTDB computer program based on the algorithm of Brutlag et al., *Comp. App. Biosci.* 6:237-245 (1990), which is herein incorporated by reference in its entirety In a sequence alignment the query and subject sequences are both DNA sequences. An RNA sequence can be compared by converting U's to T's. The result of said global sequence alignment is in percent identity. In another embodiment, parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 85%, 90%, 95%, 96%, 97%, 98% or 99% identical to, for instance, the amino acid sequences of SEQ ID NO:2 (the factor VIII portion, the Fc portion, individually or together) or 4, or a known factor VIII or Fc polypeptide sequence, can be determined conventionally using known computer programs. In one embodiment, a method for determining the best overall match between a query sequence (reference or original sequence) and a subject sequence, also referred to as a global sequence alignment, can be determined using the FASTDB computer program based on the algorithm of Brutlag et al., *Comp. App. Biosci.* 6:237-245(1990), incorporated herein by reference in its entirety. In a sequence alignment the query and subject sequences are either both nucleotide sequences or both amino acid sequences. The result of said global sequence alignment is in percent identity. In another embodiment, parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The polynucleotide variants can contain alterations in the coding regions, non-coding regions, or both. In one embodiment, the polynucleotide variants contain alterations which produce silent substitutions, additions, or deletions, but do not alter the properties or activities of the encoded polypeptide. In another embodiment, nucleotide variants are produced by silent substitutions due to the degeneracy of the genetic code. In other embodiments, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present invention. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, Factor VIII is modified, e.g., pegylated, at any convenient location. In some embodiments, Factor VIII is pegylated at a surface exposed amino acid of Factor VIII, e.g., a surface exposed cysteine, which can be an engineered cysteine. Id. In some embodiments, modified Factor VIII, e.g., pegylated Factor VIII, is a long-acting Factor VIII.

III. Method of Administering

Treatment of hemophilia A is a replacement therapy targeting restoration of FVIII activity to 1 to 5% of normal levels to prevent spontaneous bleeding (Mannucci, P. M. et al., *N. Engl. J. Med.* 344:1773-9 (2001), herein incorporated by reference in its entirety).

The present invention also includes methods of administering the pharmaceutical composition of the invention. The present invention provides a method of administering a pharmaceutical composition to a human subject in need thereof (e.g., human patient), comprising administering to the subject a therapeutic dose of a pharmaceutical composition comprising a Factor VIII polypeptide, e.g., a long-acting FVIII polypeptide or a short-acting FVIII polypeptide, e.g., a Factor VIII-Fc polypeptide, or a hybrid of such a polypeptide at a dosing interval.

In some embodiments, the pharmaceutical composition of the invention is used to reduce or decrease one or more bleeding episodes or frequency (e.g., a bleeding condition) in a subject in need thereof. In other embodiments, the pharmaceutical composition of the invention is used to treat or prevent a bleeding condition in a subject in need thereof.

The bleeding condition can be caused by a blood coagulation disorder. A blood coagulation disorder can also be referred to as a coagulopathy. In one example, the blood coagulation disorder, which can be treated with a pharmaceutical composition of the current disclosure, is hemophilia. In another example, the blood coagulation disorder, which can be treated with a pharmaceutical composition of the present disclosure is hemophilia A.

In some embodiments, the type of bleeding associated with the bleeding condition is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

In other embodiments, the subject suffering from bleeding condition is in need of treatment for surgery, including, e.g., surgical prophylaxis or peri-operative management. In one example, the surgery is selected from minor surgery and major surgery. Exemplary surgical procedures include tooth extraction, tonsillectomy, inguinal herniotomy, synovectomy, craniotomy, osteosynthesis, trauma surgery, intracranial surgery, intra-abdominal surgery, intrathoracic surgery, joint replacement surgery (e.g., total knee replacement, hip replacement, and the like), heart surgery, and caesarean section.

The present invention also provides a method of reducing or decreasing an annualized bleeding rate (ABR) of a subject having hemophilia comprising administering to the subject an effective dose of a FVIII polypeptide. In one embodiment, a long-acting FVIII polypeptide is administered at a dosing interval of every three days or longer. In another embodiment, the effective dose is between about 20 IU/kg and about 90 IU/kg. In other embodiments, the effective dose is 20-30 IU/kg, 30-40 IU/kg, 40-50 IU/kg, 50-60 IU/kg, 60-70 IU/kg, 70-80 IU/kg, or 80-90 IU/kg. In yet other embodiments, the effective dose is 20 IU/kg, 25 IU/kg, 30 IU/kg, 35 IU/kg, 40 IU/kg, 45 IU/kg, 50 IU/kg, 55 IU/kg, 60 IU/kg, 65 IU/kg, 70 IU/kg, 75 IU/kg, 80 IU/kg, 85 IU/kg, or 90 IU/kg.

In certain embodiments, administration of a FVIII polypeptide is for individualized (tailored) prophylaxis and results in an ABR of less than about 5.5, less than about 5.4, less than about 5.3, less than about 5.2, less than about 5.1, less than about 5.0, less than about 4.9, less than about 4.8, less than about 4.7, less than about 4.6, or less than about 4.5. In other embodiments, the administration results in an ABR of about 4.7 to 0. In some embodiments, the median of the ABR is about 1.6. In yet other embodiments, the mean of the ABR is about 2.9. In one aspect of the individualized prophylaxis regimen, the effective dose is about 25 IU/kg to about 65 IU/kg given every three to five days. For example, the effective dose is about 25 IU/kg to about 65 IU/kg given every three days. In another aspect, the effective dose is about 50 IU/kg to about 65 IU/kg every four days or every five days. In other aspects, the effective dose is up to 65 IU/kg every three days. In still other embodiments, the effective dose of a FVIII polypeptide is modified based on the patient's pharmacokinetic profile. In one example, the patent is administered with two doses initially, a first dose of 25 IU/kg on day 1 and a second dose of 50 IU/kg on day 4. If the pharmacokinetic data show less than 1% trough level of normal FVIII activity after the initial two doses, the patient is then administered with about 25 IU/kg to about 65 IU/kg every three days. In another example, if the pharmacokinetic data show higher than 1% trough level of normal FVIII activity for five days from the dosing, the patient is then administered with about 50 IU/kg to about 65 IU/kg every five days. If the patient experiences more than two spontaneous bleeds over eight weeks period after administration of about 50 IU/kg to about 65 IU/kg every five days, the patient is administered one of the followings: (1) up to about 65 IU/kg every three days (for the target trough level of up to 5% of normal), (2) about 50 IU/kg to about 65 IU/kg every four days (for the target trough level up to 5% of normal), or (3) about 25 IU/kg to about 65 IU/kg every three days (for the target trough level of 1% to 3% of normal). If the patient receiving about 50 IU/kg to about 65 IU/kg every four days still experiences more than two spontaneous bleeds, the maximum dose can go up to about 65 IU/kg every three days. In some examples, the Interquartile Range (IQR) of the ABR for the individualized prophylaxis regimen is 0 to 4.7.

In some embodiments, administration of a FVIII polypeptide is for weekly prophylaxis and results in an ABR of less than about 9.0, less than about 8.9, less than about 8.8, less than about 8.7, less than about 8.6, less than about 8.5, or less than about 8.4. In one example, the administration results in an ABR between about 8.4 and 0. In another example, the median of the ABR for weekly prophylaxis is about 3.6. In other examples, the mean of the ABR for weekly prophylaxis is about 8.8. In other embodiments, an effective dose for weekly prophylaxis is about 65 IU/kg once every week, e.g., every live days, every six days, every seven days, every eight days, or every nine days. In some examples, the IQR of the ABR for the weekly prophylaxis regimen is 1.9 to 8.4.

In other embodiments, administration of a FVIII polypeptide is for episodic or on-demand treatment and results in an ABR of less than about 55, less than about 54, less than about 53, less than about 52, less than about 51, less than about 50, less than about 49, less than about 48, or less than about 47. In one example, the administration results in an ABR between about 49 and 0, e.g., between 48.7 and 0. In another example, the median of the ABR for episodic (on-demand) treatment is about 33.5. In other examples, the mean of the ABR for episodic (on-demand) treatment is about 37.23. In other embodiments, an effective dose for on-demand treatment is about 10 IU/kg to 75 IU/kg every 12 to 24 hours. In some examples, the IQR of the ABR for the on-demand treatment is 21.1 to 48.7.

In some embodiments, the effective dose for individualized prophylaxis, weekly prophylaxis, or episodic treatment is a fixed dose or a stratified dose. In one aspect, the fixed dose is about 2,000 IU per dose, about 2,500 IU per dose, about 3,000 IU per dose, about 3,500 IU per dose, or about 4,000 IU per dose.

The dosing interval for a long-acting FVIII polypeptide can be at least about one and one-half to six times longer, one and one-half to five times longer, one and one-half to four times longer, one and one-half to three times longer, or one and one-half to two times longer, than the dosing interval required for an equivalent dose of the Factor VIII without the non-Factor VIII portion (a polypeptide consisting of the Factor VIII portion), e.g., without the Fc portion. The dosing interval can be at least about one and one-half, two, two and one-half, three, three and one-half, four, four and one-half, five, five and one-half or six times longer than the dosing interval required for an equivalent dose of the Factor VIII without the non-Factor VIII portion (a polypeptide consisting of the Factor VIII portion), e.g., without the Fc portion. The dosing interval can be about every three, four, five, six, seven, eight, nine, ten, eleven, twelve, thirteen, or fourteen days or longer.

The methods of the invention can be practiced on a subject in need of prophylactic treatment or on-demand treatment.

For on-demand treatment, the dosing interval of a pharmaceutical composition comprising a FVIII polypeptide is about once every 24-36, 24-48, 24-72, 24-96, 24-120, 24-144, 24-168, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours or longer.

In one embodiment, the subject is in need of on-demand (episodic) treatment. In another embodiment, on-demand (episodic) treatment resolves greater than 80% (greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, greater than 99%, or 100%) or 80-100%, 80-90%, 85-90%, 90-100%, 90-95%, or 95-100% of bleeds (e.g., spontaneous bleeds) in a single dose. In another embodiment, greater than 80% (greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or 100%) or 80-100%, 80-90%, 85-90%, 90-100%, 90-95%, or 95-100% of bleeding episodes are rated excellent or good by physicians after on-demand (episodic) treatment. In other embodiments, greater than 5%, (greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%), or 5-20%, 5-15%, 5-10%, 10-20%, or 10-15% of bleeding episodes are rated as fair by physicians after on-demand treatment.

In other embodiments, the pharmaceutical composition comprising a FVIII polypeptide is used for prophylaxis. Prophylaxis can be demonstrated by better Cmax, better Tmax, and/or greater mean residence time versus short-acting FVIII. In some embodiments, prophylaxis results in no spontaneous bleeding episodes within about 24, 36, 48, 72, or 96 hours (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, 90, 91, 92, 93, 94, 95, or 96 hours), after injection (e.g., the last injection). In certain embodiments, prophylaxis results in greater than 30% (e.g., greater than 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, or 90%, for example, greater than 50%), mean reduction in annualized bleeding episodes with once weekly dosing (e.g., at 65 IU/kg).

In another example, the subject is concomitantly treated with FIX. Because the compounds of the invention are capable of activating FIXa, they could be used to pre-activate the FIXa polypeptide before administration of the FIXa to the subject.

IV. Method of Making

A FVIII polypeptide can be manufactured in a host cell comprising a vector encoding the FVIII polypeptide. In one embodiment, the host cell is transformed with one or more vectors comprising a first nucleotide sequence encoding a FVIII polypeptide and a first FcRn polypeptide, a second nucleotide sequence encoding a second FcRn polypeptide, and optionally a third nucleotide sequence encoding a protein convertase, e.g., PC5. As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence can, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

Examples of vectors include, but are not limited to viral vectors or plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

The expression vector or vectors are then transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J* 1:841), and liposome-based reagents. A variety of host-expression vector systems can be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., Mol. Biotechnol. 34(2): 165-78 (2006).

The method can further comprise purification steps. Various known purifications steps are well known in the art.

EXAMPLES

Example 1

Product Description rFVIIIFc is a long-acting, fully recombinant fusion protein consisting of human coagulation Factor VIII (FVIII) covalently linked to the Fc domain of human immunoglobulin G1 (IgG1). The Factor VIII portion of rFVIIIFc has a primary amino acid sequence and post-translational modifications that are comparable to the 90+80 kDa form of Factor VIII (i.e., B-domain deleted). The Fc domain of rFVIIIFc contains the hinge, CH2 and CH3 regions of IgG1. rFVIIIFc contains 1882 amino acids with an apparent molecular weight of approximately 220 kilodaltons.

rFVIIIFc is produced by recombinant DNA technology in a human embryonic kidney (HEK) cell line, which has been extensively characterized. The cell line expresses rFVIIIFc into a defined cell culture medium that does not contain any proteins derived from animal or human sources. rFVIIIFc is purified by a series of chromatography steps that does not require use of a monoclonal antibody. The process includes a detergent viral inactivation step and multiple viral clearance steps including an affinity chromatography step and a 15 nm virus-retaining nano-filtration step. No human or animal additives are used in the cell culture, purification, and formulation processes.

rFVIIIFc is in the pharmacotherapeutic group: antihemorrhagics, blood coagulation factor VIII. It is provided as a sterile, preservative-free, non-pyrogenic, lyophilized, white to off-white powder to cake, for intravenous (IV) administration in a single-use vial, accompanied by a liquid diluent in a pre-filed syringe. In addition to rFVIIIFc, the pharmaceutical composition comprises in the lyophilizate sucrose, sodium chloride, L-Histidine, calcium chloride, and Polysorbate 20 or polysorbate 80, and comprising in sterilized water for injections. Each single-use vial contains nominally 250, 500, 750, 1000, 1500, 2000, 3000, 4000, 5000, or 6000 International Units (IU) of rFVIIIFc. When reconstituted with provided diluent, the product contains the following excipients: sucrose, sodium chloride, L-histidine, calcium chloride, and polysorbate 20 or polysorbate 80, at the concentrations shown in Table 1 or Table 2 below. The pharmaceutical composition is formulated for intravenous administration only after reconstitution.

Each pack contains a powder vial (type 1 glass) with a stopper (butyl) and a flip-off seal (aluminum), 3 ml solvent in a pre-filled syringe (type 1 glass) with a plunger stopper (butyl), a tip-cap (butyl), and a sterile vial adapter reconstitution device.

TABLE 1 rFVIIIFc Formulations Following Reconstitution with Liquid Diluent

| rFVIIIFc IU/ml* | Sucrose % (w/v) | NaCl (mM) | L-histidine (mM) | Calcium chloride (mM) | Polysorbate-20 % (w/v) |
|---|---|---|---|---|---|
| 83 IU/ml | 1.33 | 205 | 6.64 | 5.4 | 0.013 |
| 167 IU/ml | 1.33 | 205 | 6.64 | 5.4 | 0.013 |
| 250 IU/ml | 1.33 | 205 | 6.64 | 5.4 | 0.013 |
| 333 IU/ml | 1.33 | 205 | 6.64 | 5.4 | 0.013 |
| 500 IU/ml | 1.33 | 205 | 6.64 | 5.4 | 0.013 |
| 667 IU/ml | 1.33 | 205 | 6.64 | 5.4 | 0.013 |
| 1000 IU/ml | 1.33 | 205 | 6.64 | 5.4 | 0.013 |
| 1333 IU/ml | 1.33 | 205 | 6.64 | 5.4 | 0.013 |
| 1667 IU/ml | 1.33 | 205 | 6.64 | 5.4 | 0.013 |
| 2000 IU/ml | 1.33 | 205 | 6.64 | 5.4 | 0.013 |

TABLE 2 rFVIIIFc Formulation Following Reconstitution with Liquid Diluent

| Component | Concentration | | | | |
|---|---|---|---|---|---|
| | 250 IU/vial | 500 IU/vial | 750 IU/vial | 1000 IU/vial | 1500 IU/vial |
| rFVIIIFc* | 83 IU/mL | 167 IU/mL | 250 IU/mL | 333 IU/mL | 500 IU/mL |
| Sucrose | 13.3 mg/mL | 13.3 mg/mL | 13.3 mg/mL | 13.3 mg/mL | 13.3 mg/mL |
| Sodium Chloride | 12.0 mg/mL | 12.0 mg/mL | 12.0 mg/mL | 12.0 mg/mL | |
| L-Histidine | 1.03 mg/mL | 1.03 mg/mL | 1.03 mg/mL | 1.03 mg/mL | 1.03 mg/mL |
| Calcium Chloride Dihydrate | 0.80 mg/mL | 0.80 mg/mL | 0.80 mg/mL | 0.80 mg/mL | 0.80 mg/mL |
| Polysorbate 20 | 0.13 mg/mL | 0.13 mg/mL | 0.13 mg/mL | 0.13 mg/mL | 0.13 mg/mL |

| Component | Concentration | | | | |
|---|---|---|---|---|---|
| | 2000 IU/vial | 3000 IU/vial | 4000 IU/vial | 5000 IU/vial | 6000 IU/vial |
| rFVIIIFc* | 667 IU/mL | 1000 IU/mL | 1333 IU/mL | 1667 IU/mL | 2000 IU/mL |
| Sucrose | 13.3 mg/mL | 13.3 mg/mL | 13.3 mg/mL | 13.3 mg/mL | 13.3 mg/mL |
| Sodium Chloride | 12.0 mg/mL | 12.0 mg/mL | 12.0 mg/mL | 12.0 mg/mL | 12.0 mg/mL |
| L-Histidine | 1.03 mg/mL | 1.03 mg/mL | 1.03 mg/mL | 1.03 mg/mL | 1.03 mg/mL |
| Calcium Chloride Dihydrate | 0.80 mg/mL | 0.80 mg/mL | 0.80 mg/mL | 0.80 mg/mL | 0.80 mg/mL |
| Polysorbate 20 | 0.13 mg/mL | 0.13 mg/mL | 0.13 mg/mL | 0.13 mg/mL | 0.13 mg/mL |

*The potency (IU) is determined using the European Pharmacopoeia chromogenic assay against an in-house standard that is referenced to the WHO standard. The specific activity of rFrVIIIFc is 4000-10000 IU/mg protein.

Example 2

Method of Formulation

The rFVIIIFc drug product is a sterile lyophilized powder for injection intended for intravenous administration. It is supplied in aseptically filled single use vials which contain nominally 250, 500, 750, 1000, 1500, 2000, 3000, 4000, 5000, and 6000 IU per vial. The vials are 10 mL USP/Ph. Eur. Type 1 glass vials sealed with a 20 mm Teflon-coated butyl rubber lyophilization stopper and aluminum flip-off crimp seal. Prior to lyophilization, the nominal fill volume target for 250 through 6000 IU vials is 3 mL. The composition of the formulation excipients prior to lyophilization is the same for all dosage strengths. The powder for injection is reconstituted with 3 mL of diluent comprising sterilized water for injections supplied in a sterile prefilled syringe. The compositions of the drug product solutions prior to lyophilization are presented in Table 3. The compositions of the drug products following reconstitution are presented in Table 1 or in Table 2. (Example 1).

IFc, the expected in vivo peak increase in Factor VIII level expressed as IU/dL (or % of normal) or the required dose can be estimated using the following formulas:

$$\text{IU/dL (or \% of normal)} = [\text{Total Dose (IU)}/\text{body weight (kg)}] \times 2 \text{ (IU/dL per IU/kg)}$$

OR

Pre-lyophilization Concentration of rFVIIIFc Formulation Components

| | Concentration | | | | |
|---|---|---|---|---|---|
| Component | 250 IU/vial | 500 IU/vial | 750 IU/vial | 1000 IU/vial | 1500 IU/vial |
| rFVIIIFc | 150 IU/ml* | 287.5 IU/ml** | 431.25 IU/ml** | 575 IU/ml** | 862.5 IU/ml** |
| Sucrose | 20.0 mg/ml | 20.0 mg/ml | 20.0 mg/ml | 20.0 mg/ml | 20.0 mg/ml |
| Sodium Chloride | 18.0 mg/ml | 18.0 mg/ml | 18.0 mg/ml | 18.0 mg/ml | 18.0 mg/ml |
| L-Histidine | 1.55 mg/ml | 1.55 mg/ml | 1.55 mg/ml | 1.55 mg/ml | 1.55 mg/ml |
| Calcium Chloride Dihydrate | 1.18 mg/ml | 1.18 mg/ml | 1.18 mg/ml | 1.18 mg/ml | 1.18 mg/ml |
| Polysorbate 20 | 0.2 mg/ml | 0.2 mg/ml | 0.2 mg/ml | 0.2 mg/ml | 0.2 mg/ml |
| Water for Injection | | | To make 1 ml*** | | |
| Fill Volume | 2.0 ml | 2.0 ml | 2.0 ml | 2.0 ml | 2.0 ml |

| | Concentration | | | | |
|---|---|---|---|---|---|
| Component | 2000 IU/vial | 3000 IU/vial | 4000 IU/vial | 5000 IU/vial | 6000 IU/vial |
| rFVIIIFc | 1150 IU/ml** | 1725 IU/ml** | 2300 IU/ml** | 2875 IU/ml** | 3450 IU/ml** |
| Sucrose | 20.0 mg/ml | 20.0 mg/ml | 20.0 mg/ml | 20.0 mg/ml | 20.0 mg/ml |
| Sodium Chloride | 18.0 mg/ml | 18.0 mg/ml | 18.0 mg/ml | 18.0 mg/ml | 18.0 mg/ml |
| L-Histidine | 1.55 mg/ml | 1.55 mg/ml | 1.55 mg/ml | 1.55 mg/ml | 1.55 mg/ml |
| Calcium Chloride Dihydrate | 1.18 mg/ml | 1.18 mg/ml | 1.18 mg/ml | 1.18 mg/ml | 1.18 mg/ml |
| Polysorbate 20 | 0.2 mg/ml | 0.2 mg/ml | 0.2 mg/ml | 0.2 mg/ml | 0.2 mg/ml |
| Water for Injection | | | To make 1 ml*** | | |
| Fill Volume | 2.0 ml | 2.0 ml | 2.0 ml | 2.0 ml | 2.0 ml |

*A 20% overage is included for the 250 IU/vial strength to ensure that, after process and testing variations, at least the nominal concentration is present in the vial.
**A 15% overage is included for the 500-6000 IU/vial strengths to ensure that, after process and testing variations, at least the nominal concentration is present in the vial.
***Removed during lyophilization.

Example 3

Dosage and Method of Administration/Method of Calculating Initial Estimated Dose rFVIIIFc is long-acting anti-hemophilic factor (recombinant) indicated in adults and children (≥12 years) with hemophilia A (congenital Factor FVIII deficiency) for, e.g., control and prevention of bleeding episodes, routine prophylaxis to prevent or reduce the frequency of bleeding episodes, and perioperative management (surgical prophylaxis).

Dosing of rFVIIIFc can be estimated as described in this example, but can also be determined by standard tests such as FVIII activity assays described elsewhere herein.

1 IU of rFVIIIFc per kg body weight is expected to increase the circulating level of Factor VIII by 2 [IU/dL]. rFVIIIFc has been shown to have a prolonged circulating half-life.

Since patients can vary in their pharmacokinetic (e.g., half-life, in vivo recovery) and clinical responses to rFVII- $$\text{Dose (IU)} = \text{body weight (kg)} \times \text{Desired Factor VIII Rise (IU/dL or \% of normal)} \times 0.5 \text{ (IU/kg per IU/dL)}$$

The following table (Table 4) can be used to guide dosing in bleeding episodes:

TABLE 4

Guide to rFVIIIFc Dosing for Treatment of Bleeding

| Severity of Bleed | Desired Factor VIII Level (IU/dL or % of normal) | Dose (IU/kg)/Frequency of Doses (hrs) |
|---|---|---|
| Minor and Moderate For example: joint, superficial muscle/no neurovascular compromise (except iliopsoas), deep laceration and renal, superficial soft tissue, mucous membranes | 40-60 | 20-30 IU/kg Repeat every 24-48 hours until bleeding is resolved |

TABLE 4-continued

Guide to rFVIIIFc Dosing for Treatment of Bleeding

| Severity of Bleed | Desired Factor VIII Level (IU/dL or % of normal) | Dose (IU/kg)/Frequency of Doses (hrs) |
|---|---|---|
| Major<br>For example: iliopsoas and deep muscle with neurovascular injury, or substantial blood loss, retroperitoneum, CNS, throat and neck, gastrointestinal. | 80-100 | 40-50 IU/kg<br>Repeat every 12-24 hours until bleeding is resolved |

Adapted from WFH 2012

Subsequent dosage and duration of treatment depends on the individual clinical response, the severity of the Factor VIII deficiency, and the location and extent of bleeding.

The following table (Table 5) can be used to guide dosing for perioperative management (surgical prophylaxis):

TABLE 5

Guide to rFVIIIFc Dosing for Perioperative Management (Surgical Prophylaxis)

| Type of Surgery | Target Factor VIII Level (IU/dL or % of normal) | Dose (IU/kg)/Frequency of Doses (hrs) |
|---|---|---|
| Minor<br>Minor operations including uncomplicated dental extraction | 50 to 80 | 25-40 IU/kg<br>A single infusion can be sufficient. Repeat every 24 hours as needed to control bleeding. |
| Major<br>Major operations including intra-abdominal, joint replacement surgery | 80 to 120 | An initial preoperative dose of 40-60 IU/kg followed by a repeat dose of 40-50 IU/kg after 8-24 hours and then every 24 hours to maintain FVIII activity within the target range. rFVIIIFc has a longer half-life than plasma and recombinant FVIII products (see Example 5) |

For routine prophylaxis, the recommended regimen is 50 IU/kg every 3-5 days. The dose can be adjusted based on patient response in the range of 25-65 IU/kg.

For weekly prophylaxis, the recommended dose is 65 IU/kg.

rFVIIIFc is contraindicated in patients who have manifested severe hypersensitivity reactions, including anaphylaxis, to the product or its components. Severe hypersensitivity reactions were not observed in clinical trials; however, these have been known to occur with use of other factor VIII replacement factors.

The clinical response to rFVIIIFc can vary. If bleeding is not controlled with the recommended dose, the plasma level of Factor VIII can be determined, and a sufficient dose of rFVIIIFc can be administered to achieve a satisfactory clinical response. If the patient's plasma Factor VIII level fails to increase as expected or if bleeding is not controlled after rFVIIIFc administration, the presence of an inhibitor (neutralizing antibodies) should be suspected, and appropriate testing performed. Patients using rFVIIIFc can be monitored for the development of Factor VIII inhibitors by appropriate clinical observations and laboratory tests known to those of ordinary skill in the art.

Patient's plasma can be monitored for Factor VIII activity levels, e.g., the one-stage clotting assay to confirm adequate Factor VIII levels have been achieved and maintained, when clinically indicated. Patient's plasma can further be monitored for the development of Factor VIII inhibitors.

Example 4

Phase 3 Clinical Trial of Extended Half-Life Recombinant Fc Fusion Factor VIII ("A-LONG" Study)

Summary of A-LONG Study

In the A-LONG study, 165 male patients aged 12 years of age and older were enrolled. The A-LONG study had three treatment arms: individualized prophylaxis, weekly prophylaxis and episodic (on-demand) treatment (Arms 1, 2 and 3, respectively). In a subgroup of patients across treatment arms, rFVIIIFc was evaluated in the perioperative management of patients who required a major surgical procedure during the study.

Overall, 92.7 percent of patients completed the study. Recombinant FVIIIFc was generally well-tolerated. No inhibitors to rFVIIIFc were detected and no cases of anaphylaxis were reported in any patients, all of whom switched from commercially-available Factor VIII products. No serious adverse events were assessed to be related to drug by the investigator.

The most common adverse events (incidence of ≥5 percent) occurring outside of the perioperative management period were nasopharyngitis, arthralgia, headache, and upper respiratory tract infection.

The median (mean) annualized bleeding rates (ABR), including spontaneous and traumatic bleeds, were 1.6 (2.9) in the individualized prophylaxis arm, 3.6 (8.8) in the weekly prophylaxis arm and 33.6 (37.2) in the episodic treatment arm. In the individualized prophylaxis arm, the median dosing interval was 3.5 days. During the last 3 months on study, 30 percent of patients in the individualized prophylaxis arm achieved a mean dosing interval of at least 5 days.

Control of bleeding was assessed in all patients who experienced a bleeding episode during the study. Overall, 98 percent of bleeding episodes were controlled by one or two injections of rFVIIIFc.

In addition, rFVIIIFc was assessed in the perioperative management of 9 patients undergoing 9 major surgical procedures. The treating physicians rated the hemostatic efficacy of rFVIIIFc as excellent or good in 100 percent of these surgeries.

A-LONG included pharmacokinetic (PK) analysis of rFVIIIFc in all patients in the study. In a protocol-defined subset of patients with extensive PK sampling, the approximate terminal half-life of rFVIIIFc was 19.0 hours compared to 12.4 hours for ADVATE® [Antihemophilic Factor (Recombinant), Plasma/Albumin-Free Method], consistent with the results obtained in the Phase 1/2 study of rFVIIIFc.

About the A-LONG Study and the rFVIIIFc Program

A-LONG was a global, open-label, multi-center Phase 3 study that evaluated the efficacy, safety and pharmacokinetics of intravenously-injected rFVIIIFc. The study was designed to evaluate rFVIIIFc in the control and prevention of bleeding, routine prophylaxis and perioperative management in patients with hemophilia A. A-LONG involved 60 hemophilia treatment centers in 19 countries on 6 continents.

The A-LONG study had three treatment arms. In Arm 1 (individualized prophylaxis; n=117), patients were treated with 25-65 IU/kg of rFVIIIFc, at an interval of every three to five days, which was individualized to maintain factor trough levels sufficient to prevent bleeding. In Arm 2 (weekly prophylaxis; n=24), patients were treated with a weekly dose of 65 IU/kg. In Arm 3 (episodic treatment; n=23), patients received rFVIIIFc episodic treatment as needed for bleeding. In a subgroup of patients across treatment arms, rFVIIIFc was evaluated in the surgical setting.

The primary efficacy measures were the per-patient annualized bleeding rate in Arm 1 vs. Arm 3, and pharmacokinetics of rFVIIIFc vs. rFVIII (one-stage clotting [activated partial thromboplastin time] assay and the chromogenic assays calibrated to normal human references plasma with potency traceable to Word Health Organization standards). The safety endpoints included the incidence of adverse events and inhibitor development (Nijmegen-modified Bethesda assay) in patients studied for up to 54 weeks. Secondary efficacy endpoints included ABR in Arm 2 vs. Arm 3, annualized number of spontaneous and joint bleeding episodes per patient, number of injections and dose per injections to resolve a bleed, and investigators' assessments of patients' response to surgery with rFVIIIFc using a bleeding response scale (surgery subgroup only), response to treatment of bleeding episodes and the pharmacokinetics of rFVIIIFc versus ADVATE®. Non-neutralizing antibodies (NNAs) were assessed with an electrochemiluminescence-based anti-rFVIIIFc binding-antibody assay.

Ongoing clinical studies of rFVIIIFc include the Kids A-LONG and ASPIRE studies. Kids A-LONG is a Phase 3, open-label study in previously-treated children with hemophilia A under age 12, which is actively recruiting patients. ASPIRE is a long-term open-label study for patients who completed the A-LONG study or who complete the Kids A-LONG study.

A-LONG Study Design

Design: Global, open-label, multicenter, Phase 3 study. The study protocol was approved by local Institutional Review Boards for each participating institution, and the study was conducted in accordance with the International Conference on Harmonisation guidelines for Good Clinical Practice.

Objectives: To evaluate the efficacy and safety of intravenously-injected recombinant factor VIII Fc fusion protein (rFVIIIFc) in the control and prevention of bleeding episodes, routine prophylaxis, and perioperative management in individuals with severe hemophilia A.

Key Inclusion Criteria:
a. Male
b. ≥12 years of age and at least 40 kg
c. Diagnosis of severe hemophilia A defined as <1% (<1 IU/dL) endogenous factor VIII (FVIII) activity
d. Previously Treated Patients (PTPs): history of ≥150 prior documented exposure days (EDs) with any currently marketed FVIII product, been on prophylaxis ≥2 times per week with a FVIII product (for Arm 1 only), or experienced ≥12 bleeds in the past 12 months on an episodic regimen.
e. No current/prior FVIII inhibitors of measurable activity.
f. No history of inhibitors, or history of hypersensitivity or anaphylaxis associated with any FVIII or intravenous immunoglobulin administration
g. All subjects (or their guardians in the case of minors) gave informed written consent prior to study participation.

Treatment Arms:

Details of A-LONG study design is described below.

Arm 1 (individualized prophylaxis) was administered 25-65 IU/kg every 3-5 days (maximum 5-day dosing interval). Subjects were treated with an initial dose of 25 IU/kg on Day 1 and 50 IU/kg on Day 4, which was subsequently adjusted to maintain trough factor levels sufficient to prevent bleeding. Further dose adjustments to target trough levels of 3 to 5 IU/dL permitted after week 7 if subject experienced ≥2 moderate/severe bleeds over a rolling 8-week period; 10 to 20 IU/kg rFVIIIFc (target 20-40 IU/dL FVIII) for minor bleeding episodes; 15 to 30 IU/kg rFVIIIFc (target 30-60 IU/dL FVIII) for moderate to major bleeding episodes; 40 to 50 IU/kg rFVIIIFc (target 80-100 IU/dL FVIII) for major to life-threatening bleeding episodes.

Arm 2 (weekly prophylaxis) was administered 65 IU/kg dose. Subjects were treated with 65 IU/kg once weekly with no dose or interval adjustment.

Arm 3 (episodic [on-demand] treatment) was administered 10-50 IU/kg. Subjects received rFVIIIFc episodic treatment as needed for bleeding.

A Perioperative Management Subgroup was established. In this subgroup, rFVIIIFc was administered prior to and following surgery in the subset of patients requiring a major surgical procedure during the study. Subjects in any treatment arm could be enrolled in the surgery subgroup. Eligibility: required major surgery; ≥12 exposure days to rFVIIIFc with negative inhibitor titre following this period and within 4 weeks prior to surgery; and, completed, at minimum, abbreviated PK sampling.

All subjects (excluding sequential PK subgroup) underwent PK sampling from pre-injection with rFVIIIFc up to 96-hours post-injection, according to schedule: pre-injection, 30 (±3) minutes, 3 hours (±15 minutes), 72 (±2) hours (Day 3), and 96 (±2) hours (Day 4) from start of injection.

Pharmacokinetic (PK) Assessment was performed. All subjects in all arms had an initial PK assessment after their first dose of rFVIIIFc. A subset of subjects from Arm 1 were assigned to a protocol-specified sequential PK subgroup to compare the stability of PK properties of rFVIIIFc over time with that of recombinant factor VIII (rFVIII, ADVATE® [anti-hemophilic factor (recombinant) plasma/albumin-free method], octocog alfa) as follows:

Prior to treatment in Arm 1, PK was assessed after a single dose of ADVATE® 50 IU/kg. PK was then assessed in these same subjects after a single dose of rFVIIIFc 50 IU/kg. PK of rFVIIIFc was repeated at 12 to 24 weeks.

Details on the design of the sequential PK subgroup (Arm 1) dosing and PK sampling is described in FIG. 1

Key efficacy outcome measures (included in initial readout):
a. Annualized bleeding rate (ABR) in Arm 1 versus Arm 3
b. Individualized prophylaxis arm compared with episodic treatment arm.
c. Number of injections required to resolve a bleeding episode
d. Number of injections required to resolve bleeding episodes
e. Median dose required to resolve bleeding episodes
f. Treating physicians' assessments of subjects' response to surgery with rFVIIIFc using a 4-point scale PK outcome measures included:
a. The primary PK assessment were based on FVIII activity levels determined at a central laboratory by one-stage clotting assay and by the chromogenic assay against commercially available plasma standards.

b. PK of rFVIIIFc and ADVATE®
c. PK properties of rFVIIIFc were compared with rFVIII (ADVATE®; sequential PK subgroup). Overall study duration was ≤75 weeks for all subjects. The primary efficacy endpoint was annualized bleeding rate (ABR; Arms 1 and 2 vs. Arm 3). Prophylaxis dose and interval, number of injections required for treatment of bleeding episodes, and perioperative haemostasis were evaluated.

Key safety outcome measures included:
a. Incidence of inhibitor development. The study was powered to detect the occurrence of inhibitors with a 2-sided 95% confidence interval using the Clopper-Pearson exact method if 2 cases of inhibitor formation was observed.
b. Incidence of adverse events (AEs) occurring outside of the perioperative management period Adherence with treatment (adherence measures) was assessed using patient electronic diaries.

A-LONG Results

Subjects

A total of 165 subjects were enrolled in the study. Median age was 30 years (range, 12-65) and 8% were <18 years. The number of patients in each arm of the study were: Arm 1 (individualized prophylaxis), n=118; Arm 2 (weekly prophylaxis), n=24; Arm 3 (episodic treatment), n=23; and perioperative management subgroup, n=9, 9 surgeries (8 subjects from Arm 1 and 1 from Arm 2). Subjects from each treatment arm were eligible to enter the surgery subgroup if they required major surgery, had ≥12 EDs to rFVIIIFc and a negative inhibitor titre following this period and within 4 weeks prior to surgery. Patients on prior episodic treatment had a higher median number of bleeding episodes in the 12 months prior to the study, and a higher proportion of patients in Arms 2 and 3 had target joints. For patients on prior prophylaxis, 87% reported injecting at least three times weekly.

92.7% of subjects completed the study. In total, 153 (approximately 93%) subjects completed the study; 112/118 (95%) in Arm 1, 19/24 (795) in Arm 2, and 22/23 (96%) in Arm 3. Reasons for premature discontinuation were: Arm 1—subject withdrawal (n=2), physician decision (n=2), other (n=1), death (n=1); Arm 2—subject withdrawal (n=2; adverse events (AEs) related to study drug can have contributed), AEs (n=2), other (n=1); Arm 3—other (n=1).

Age, race, and geography of subjects were representative of the global haemophilia A population who have access to treatment, as summarized in TABLE 6.

TABLE 6

A-LONG subjects demographics

| Demographic | Arm 1 (N = 118) | Arm 2 (N = 24) | Arm 3 (N = 23) | Total N = 165 |
|---|---|---|---|---|
| Age (years), median (min-max) | 29.0 (12-65) | 31.5 (18-59) | 34.0 (13-62) | 30.0 (12-65) |
| Weight (kg), median (min-max) | 71.65 (42.0-127.4) | 75.85 (50.0-105.0) | 70.00 (48.0-110.4) | 71.60 (42.0-127.4) |
| BMI (kg/m$^2$) median (min-max) | 23.90 (15.3-37.1) | 24.60 (18.8-37.4) | 22.80 (17.2-35.6) | 23.90 (15.3-37.4) |
| Race, n (%) | | | | |
| White | 79 (66.9) | 12 (50.0) | 16 (69.6) | 107 (64.8) |
| Black | 7 (5.9) | 1 (4.2) | 2 (8.7) | 10 (6.1) |
| Asian | 27 (22.9) | 11 (45.8) | 5 (21.7) | 43 (26.1) |
| Other | 5 (4.2) | 0 | 0 | 5 (3.0) |
| Geographic location—n (%) | | | | |
| Europe | 34 (28.8) | 3 (12.5) | 4 (17.4) | 41 (24.8) |
| North America | 44 (37.3) | 5 (20.8) | 7 (30.4) | 56 (33.9) |
| Other* | 40 (33.9) | 16 (66.7) | 12 (52.2) | 68 (41.2) |
| Genotype—n (%) | | | | |
| Intron 22 inversion | 41 (35.0) | 7 (33.3) | 9 (39.1) | 57 (35.4) |
| Frameshift | 24 (20.5) | 4 (19.0) | 6 (26.1) | 34 (21.1) |
| Missense mutation | 22 (18.8) | 4 (19.0) | 1 (4.3) | 27 (16.8) |
| Nonsense mutation | 19 (16.2) | 6 (28.6) | 1 (4.3) | 26 (16.1) |
| Splice site change | 7 (6.0) | 0 | 4 (17.4) | 11 (6.8) |
| Intron 1 inversion | 3 (2.6) | 0 | 1 (4.3) | 4 (2.5) |
| Duplication | 1 (0.9) | 0 | 0 | 1 (0.6) |
| NA | 0 | 0 | 1 (4.3) | 1 (0.6) |
| von Willebrand factor antigen—median IU/dl (IQR) | 118.0 (85, 151) | 129.0 (86, 166) | 131.0 (83, 155) | 118.0 (85, 153) |
| Pre-study FVIII regimen—n (%) | | | | |
| Prophylaxis | 87 (73.7) | 0 | 0 | 87 (52.7) |
| Episodic | 31 (26.3) | 24 (100) | 23 (100) | 78 (47.3) |
| Estimated no. of bleeds prior 12 mo—median (IQR)† | | | | |
| Prior prophylaxis | 6.0 (2, 15) | — | — | 6 (2, 15) |
| Prior episodic | 27.0 (17, 41) | 29.5 (19, 44) | 24.0 (15, 36) | 27 (18, 40) |
| ≥1 Target joint—n (%) | | | | |
| Prior prophylaxis | 47 (39.8) | — | — | 47 (28.5) |
| Prior episodic | 26 (22.0) | 22 (91.7) | 18 (78.3) | 66 (40.0) |
| Family history of inhibitor | 4 (3.4) | 1 (4.2) | 2 (8.7) | 7 (4.2) |
| HIV positive | 25 (21.2) | 4 (16.7) | 7 (30.4) | 36 (21.8) |
| HCV positive | 55 (46.6) | 14 (58.3) | 13 (56.5) | 82 (49.7) |

BMI, body mass index; HIV, human immunodeficiency virus; HCV, hepatitis C virus
IU/dl denotes international units per deciliter, BMI body mass index, HIV human immunodeficiency virus, HCV hepatitis C virus, NA not applicable.
*Other included Australia, New Zealand, Brazil, Hong Kong, India, Japan, Russia, and South Africa.
†Calculation was based on available data.

Subjects received rFVIIIFc for a median (min-max) of 30.5 (<1-54) weeks with a median (minimum to maximum) in arms 1, 2, and 3 of 32.1 (9, 54), 28.0 (<1, 38), and 28.9 (15, 32) weeks, respectively. In total, 111 subjects (67.7%) had >50 EDs to study drug. A total of 9356 injections were administered during the study, corresponding to 9170 EDs (100.2 patient-years of exposure). Overall, 93.6% of patients were compliant with both the prescribed dose and interval in the prophylaxis arms.

Overall, 93.6% of subjects were adherent with both the prescribed dose and the prescribed dosing interval in the prophylaxis treatment arms.

Efficacy

In total, 163 subjects were included in efficacy analyses. One subject was excluded due to only receiving ADVATE® (Arm 1); another subject withdrew before efficacy assessment (Arm 2). Median ABR with the 25th and 75th percentiles (interquartile range [IQR]) were as follows: Arm 1—individualized prophylaxis arm: 1.6 (0.0, 4.7); Arm 2—weekly prophylaxis arm: 3.6 (1.9, 8.4); and Arm 3—episodic treatment arm: 33.6 (21.1, 48.7). Most bleeding episodes were spontaneous. In Arms 1, 2, and 3, respectively, 45.3%, 17.4%, and 0% had no bleeding episodes and 13.7%, 34.8%, and 0% had 1 bleeding episode.

Median Dosing Interval:
a. In the individualized prophylaxis arm, the median dosing interval was 3.5 days, during the last 3 months on study.
b. 30 percent of patients in the individualized prophylaxis arm achieved a mean dosing interval of at least 5 days.
c. Overall, the median (IQR) dosing interval with individualised prophylaxis aimed to achieve a FVIII trough of at least 1 to 3 IU/dL (with the maximum 5-day dosing interval permitted in the protocol) was 3.5 (3.2-4.4) days (Table 7) based on the median (IQR) weekly dose of 78 (72-91) IU/kg.
d. Approximately 30% of subjects achieved a mean dosing interval of 5 days over the last 3 months on study. 100% of subjects had mean dosing intervals ≥2 days throughout the study.

The median dose per injection for Arm 3 episodic regimen was 26.5 IU/kg (n=23) and the median total dose per bleeding episode was 27.4 IU/kg (n=23).

TABLE 7

Comparative pharmacokinetics for rFVIIIFc vs. rFVIII (n = 28)[1]

| PK parameter | Geometric mean for rFVIIIFc PK (95% CI) | Geometric mean for rFVIII PK (95% CI) | Geometric mean of intra-subject ratio (95% CI) p-value |
|---|---|---|---|
| Elimination $t_{1/2}$ (h) | 18.97 (17.03, 21.12) | 12.43 (11.14, 13.86) | 1.53 (1.36, 1.71) <0.001 |
| CL (mL/h/kg) | 1.95 (1.71, 2.22) | 3.041 (2.71, 3.41) | 0.64 (0.60, 0.69) <0.001 |
| Time to 1 IU/dL (days) (50 IU/kg dose) | 4.92 (4.43, 5.46) | 3.30 (2.99, 3.65) | 1.49 (1.41, 1.57) <0.001 |

[1]Arm 1 sequential PK group, compartmental model, one-stage assay. Estimates and 95% CIs for geometric means and geometric mean ratios; statistical significance assessed at the 2-sided 0.05 level; PK pharmacokinetics; CI, confidence interval; Cmax, maximal concentration; AUC, area-under-the-curve; t½, half-life; CL, clearance; MRT, mean residence time; Vss, volume of distribution at steady state.

Control of bleeding: approximately 98% (97.7%) of bleeding episodes were controlled by one or two injections of rFVIIIFc. 87.3% of bleeds were controlled with one injection. 1.7% required three injections.

Perioperative management: Overall, 9 major surgeries were performed in 9 subjects (8 subjects from Arm 1; 1 subject from Arm 2), including knee arthroplasty (n=5), laparoscopic inguinal hernia repair (n=2), appendectomy (n=1), and arthroscopy (n=1). Treating physicians rated the hemostatic efficacy of rFVIIIFc as excellent (8/9) or good (1/9) in 100% of surgeries. Median (min, max) estimated blood loss available for 7/9 surgeries was 15.0 (0, 600) mL during surgery and 0.0 (0, 1100) mL post-operatively; postsurgical drainage).

PK

Comparative PK data for rFVIIIFc and ADVATE® available from 28 subjects in the Arm 1 sequential PK subgroup are summarised in Table 7.
a. rFVIIIFc demonstrated an approximate 50% longer elimination half-life (FIG. 2) and mean residence time compared with ADVATE® (P<0.001) due to a 35% reduction in rFVIIIFc clearance with respect to ADVATE®.
b. Geometric mean time to 1 IU/dL FVIII activity following a 50-IU/kg dose was approximately 5 days for rFVIIIFc versus approximately 3 days for ADVATE® (P<0.001; Table 7, FIG. 2).
c. Incremental recovery for rFVIIIFc was clinically comparable with ADVATE®.
d. There was no shift in the PK properties of rFVIIIFc as evidenced by comparable PK properties between the baseline and repeat rFVIIIFc PK profiles.
e. Analogous PK results were obtained when the analysis was based on the chromogenic FVIII assay.
f. The one-stage and chromogenic clotting assays accurately and precisely measured both rFVIIIFc and ADVATE® utilising commercially available plasma FVIII standards.

The geometric mean (95% confidence interval) terminal half-life of rFVIIIFc was approximately 19.0 hours (17.0, 21.1) hours, which is 1.53-fold longer than that of ADVATE® (approximately 12.4 (11.1, 13.9) hours).

Geometric mean time (IQR) to 1% FVIII activity following 50 IU/kg of rFVIIIFc was approximately 5 days (4.92 (4.43, 5.46) days). Comparable PK profiles of rFVIIIFc were observed at Week 14. The median dosing interval with individualized prophylaxis was 3.5 days and the median dose per week was 78 IU/kg; approximately 30% of subjects achieved a mean dosing interval of ≥5 days over the last 3 months on study (subjects with ≥6 months on study) as shown in Table 8. 98% of bleeding episodes were controlled with 1-2 injections.

TABLE 8

Prophylactic dosing summary

| | n | Arm 1 Individualised prophylaxis | n | Arm 2 Weekly prophylaxis |
|---|---|---|---|---|
| Median dose, IU/kg/week (IQR) | | | | |
| Overall | 117 | 77.9 (72.3, 91.2) | 23 | 65.6 (64.2, 68.2) |
| Last 3 months[1] | 112 | 77.7 (71.9, 106.2) | 16 | 65.5[2] (64.3, 67.3) |
| Median dosing interval days (IQR) | | | | |
| Overall | 117 | 3.5 (3.2, 4.4) | | |
| Last 3 months[1] | 112 | 3.5[3] (30, 5.0) | | |

[1]Based on last 3 months on study for subjects on study ≥6 months
[2]Fixed dose of 65 IU/kg/wk.
[3]30% of subjects achieved every 5-day pharmacokinetic-driven dosing to maintain troughs 1% to 3% above baseline.
IQR, interquartile range.

Safety

No inhibitors were detected to rFVIIIFc, and no cases of anaphylaxis, allergy, or serious thrombic events were reported.

rFVIIIFc was generally well tolerated, and no serious adverse events were assessed to be related to rFVIIIFc.

The most common AEs, regardless of causality, (incidence ≥5%) occurring outside of the perioperative management period were nasopharyngitis, arthralgia (joint pain), headache, and upper respiratory tract infection, as summarized in Table 9.

12 subjects (7.3%) experienced at least one serious AE (SAE) outside of the perioperative management period.

No SAEs were assessed to be related to drug by the investigator.

Insignificant incidence of non-neutralizing antibody (NNA) has been observed under NNA assay, which is approximately 20 times more sensitive than Bethesda assay. Five subjects were found positive for NNAs at baseline, but all had at least one negative evaluation during the study. Six subjects, four in Arm 1 study and two in Arm 2 study, became positive during the study. In almost all cases, however, antibodies were transient and of low titer, and in all cases antibodies were directed against FVIII.

Overall, 14 (8.5%) subjects reported SAEs. No SAEs were determined by the investigator as related to study drug, and SAEs reported were not experienced in more than 1 subject. There was 1 death during the study, attributed to polysubstance overdose, and assessed as unrelated to rFVIIIFc by the investigator.

TABLE 9

Summary of adverse events (AEs)

| | Total N = 164 n (%) |
|---|---|
| Any AE | 108 (65.9) |
| Most common AEs (≥5% of subjects) | |
| Nasopharyngitis | 20 (12.2) |
| Arthralgia | 13 (7.9) |
| Headache | 9 (5.5) |
| Upper respiratory infection | 9 (5.5) |

Summary

Individualized and weekly prophylactic regimens resulted in low single-digit median annualized bleeding rates In the individualized prophylaxis arm, the median dosing interval was 3.5 days. During the last 3 months on study, 30 percent of patients in the individualized prophylaxis arm achieved a mean dosing interval of at least 5 days.

98% of bleeding episodes were controlled by one or two injections of rFVIIIFc. In total, 757 bleeding episodes (Arm 1=209; Arm 2=92; Arm 3=456) were treated in 106 of the 164 subjects. 87.3% required a single injection of rFVIIIFc for resolution, and 97.8% required ≤2 injections. A total of 85.6%, 80.4% and 89.5% of bleeding episodes were resolved with 1 injection of rFVIIIFc in Arms 1, 2 and 3, respectively.

Hemostatic efficacy of rFVIIIFc during surgery was rated by treating physicians as excellent or good in 100% of surgeries.

The half-life of rFVIIIFc was approximately 19.0 hours compared to 12.4 hours for ADVATE®.

No subject developed an inhibitor or experienced an anaphylactic reaction to rFVIIIFc.

Recombinant FVIIIFc was generally well tolerated.

A-LONG was the largest registrational global pivotal phase 3 study of long-lasting rFVIII in severe haemophilia A conducted to date. The study showed that rFVIIIFc offers the potential for a markedly reduced injection frequency, decreased treatment burden, an improvement in clinical outcomes for prevention of bleeds in patients with severe haemophilia A.

Goal of the study design: The study was designed to evaluate the efficacy and safety of rFVIIIFc in the control and prevention of bleeding episodes, routine prophylaxis, and perioperative management in subjects with severe hemophilia A. In addition, the study was designed to assess the effective dose and interval of rFVIIIFc for prophylaxis, as well as the feasibility of weekly treatment at a dose of 65 IU/Kg.

Episodic treatment is the administration of replacement factor only as needed to treat bleeding episodes after they have started. Prophylactic treatment is the regular administration of replacement factor to prevent bleeding episodes.

The starting regimen was 25 IU/kg on Day 1 and 50 IU/kg on Day 4. The dose and frequency of treatment could be adjusted based on the subject's PK profile and the goal was to maintain trough factor levels sufficient to prevent bleeding episodes using doses between 25 IU/kg and 65 IU/kg and treatment intervals of 3 to 5 days.

More than half of severe hemophilia A patients in the US still do not follow a prophylaxis regimen, due in part to the treatment burden. We therefore included the weekly dosing regimen in the A-LONG study to evaluate whether this regimen would result in a lower ABR compared to an episodic regimen. The median ABR in the weekly regimen was 3.59 (IQR 1.9, 8.4) compared with 33.6 (IQR 21.1, 48.7) for episodic treatment.

All subjects had an initial PK evaluation to characterize the PK of rFVIIIFc in a representative population of patients with Hemophilia A.

More extensive PK sampling was conducted in a subset of subjects in the individualized prophylaxis arm (Arm 1) at baseline after a single dose of ADVATE® (50 IU/kg), and after a 4 day washout, followed by a single dose of rFVIIIFc (50 IU/kg), Blood samples were taken for ADVATE® over a period of 72 hours. Blood samples were then taken for rFVIIIFc over a period of 120 hours. PK assessment of rFVIIIFc in this subset was repeated at 12 to 24 weeks with the same PK sampling schedule.

In peri-operative management, a single injection of rFVIIIFc was sufficient to maintain haemostasis to the end date/time of all major surgeries at a median dose of 51.4 IU/kg. Median rFVIIIFc consumption (summarized over all injections during each referenced time period) was 80.6 IU/kg on the day of major surgery, 161.3 IU/kg for Days 1-3 days following surgery, and 387.1 IU/kg for Days 4-14 following surgery. Perioperative haemostasis with rFVIIIFc was rated as excellent or good for all 9 major surgeries. No subjects reported a bleeding episode during the postoperative or rehabilitation periods. Overall, 7 adverse events (AEs) were reported in 4 (44.4%) subjects in the surgery subgroup, of which 6 AEs were of mild or moderate severity, and 1 AE was considered severe. Two serious AEs (inguinal hernia and appendicitis) were reported in 2 subjects. All AEs during the perioperative period were assessed by the investigators as unrelated to rFVIIIFc treatment.

Treating physicians rated the hemostatic efficacy of rFVIIIFc as excellent or good in 100% of surgeries on a 4 point scale including excellent, good, fair, and poor/none.

rFVIIIFc resulted in low median ABRs of 3.59 in the weekly prophylaxis arm and 1.60 in the individualized interval prophylaxis arm. In contrast, the episodic treatment arm had a median ABR of 33.57.

In the individualized prophylaxis arm, the median dosing interval was 3.5 days at a median dose of 77.7 IU/kg during the last 3 months on study.

The terminal half-life was approximately 18.97 hours for rFVIIIFc and approximately 12.3 hours for ADVATE®.

97.8% of bleeding episodes were controlled by one or two injections.

Hemostatic efficacy of rFVIIIFc for perioperative management was rated by treating physicians as excellent or good in 100% of surgeries.

Arm 2 was a weekly dosing regimen. It was designed to investigate benefit for patients on prophylaxis therapy, and to compare those results with subjects using an episodic treatment regimen. The median ABR in Arm 2 was 3.59 compared with 33.57 for the episodic treatment regimen (Arm 3).

The median dose per injection required for resolution of bleeding was 27.4 IU/kg, and the median total dose required was 28.2 IU/kg.

The median number of injections required for resolution of a bleeding episode was consistently 1.0 when treatment was administered within 8 hours of bleed onset, regardless of type or location of bleed. Overall, 78.8% of rFVIIIFc injections in Arm 1, 64.8% in Arm 2, and 79.7% of injections in Arm 3, were rated by subjects as producing excellent or good response. The median dosing interval of 3.5 days from Arm 1 represents the dosing interval that can be achieved by the majority of patients: 30% of patients were able to achieve a dosing interval of at least 5 days. Some patients were able to achieve a weekly prophylaxis regimen (Arm 2) with a median ABR of 3.59 bleeding episodes.

Subjects in the individualized prophylaxis arm received an initial dose of 25 IU/kg on Day 1 and 50 IU/kg on Day 4. The study design allowed for adjustment of the dosing interval and dose to maintain targeted trough factor levels and to prevent bleeding. We believe the median dosing interval and dose based on the last 6 months on study is most representative of the individualized prophylaxis regimen.

87.3% of bleeding episodes were resolved with one injection of rFVIIIFc and 97.8% were resolved with one or two injections. For the 96 (12.7%) bleeding episodes that required more than 1 injection for resolution, the median interval between the first and second injection was 30.9 hours.

The investigators' global assessment of subject response to their assigned rFVIIIFc regimen was rated as excellent or effective for 99.4%, 100%, and 98.1% of the subject visits in Arms 1, 2, and 3, respectively.

In A-LONG, the clotting factor activity was measured using a one-stage (aPTT) clotting assay and a chromogenic assay. The reported half-lives are based on the results of the one-stage clotting assay. While the half-lives of rFVIIIFc and ADVATE® were both slightly longer with the chromogenic assay, the ratios between products were consistent between the two assays.

EMBODIMENTS

E1. A pharmaceutical composition comprising:
(a) a FVIII polypeptide;
(b) one or more stabilizing agents selected from the group consisting of sucrose, trehalose, raffinose, arginine, and mixture thereof;
(c) sodium chloride (NaCl);
(d) L-histidine;
(e) calcium chloride; and
(f) polysorbate 20 or polysorbate 80.

E2. The pharmaceutical composition of embodiment E1, wherein mannitol, glycine, alanine, or hydroxyethyl starch is not included.

E3. The pharmaceutical composition of embodiment E1 or E2, wherein NaCl is the only bulking agent.

E4. The pharmaceutical composition of any one of embodiments E1 to E3, comprising sucrose.

E5. The pharmaceutical composition of embodiment E4, comprising about 1% (w/v) to about 2.5% (w/v) sucrose.

E6. The pharmaceutical composition of embodiment E5, comprising about 1.3% (w/v) sucrose to about 2.0% (w/v) sucrose.

E7. The pharmaceutical composition of embodiment E6, comprising about 1.33% (w/v) sucrose or about 2.0% (w/v) sucrose.

E8. The pharmaceutical composition of embodiment E4, comprising about 10 mg/ml to about 25 mg/ml sucrose.

E9. The pharmaceutical composition of embodiment E8, comprising about 13 mg/ml to about 20 mg/ml sucrose.

E10. The pharmaceutical composition of embodiment E9, comprising about 13.3 mg/ml sucrose or about 20.0 mg/ml sucrose.

E11. The pharmaceutical composition of any one of embodiments E1 to E10, comprising about 150 mM to about 250 mM NaCl.

E12. The pharmaceutical composition of embodiment E11, comprising about 175 mM to about 225 mM NaCl.

E13. The pharmaceutical composition of embodiment E12, comprising about 200 mM to about 210 mM NaCl.

E14. The pharmaceutical composition of embodiment E13, comprising about 205 mM NaCl.

E15. The pharmaceutical composition of any one of embodiments E1 to E10, comprising about 8.8 mg/ml to about 14.6 mg/ml NaCl.

E16. The pharmaceutical composition of embodiment E15, comprising about 10 mg/ml to about 13 mg/ml NaCl.

E17. The pharmaceutical composition of embodiment E16, comprising about 12.0 mg/ml NaCl.

E18. The pharmaceutical composition of any one of embodiments E1 to E10, comprising about 250 mM to about 350 mM NaCl.

E19. The pharmaceutical composition of embodiment E18, comprising about 275 mM to about 325 mM NaCl.

E20. The pharmaceutical composition of embodiment E19, comprising about 308 mM NaCl.

E21. The pharmaceutical composition of any one of embodiments F1 to E10, comprising s about 14.6 mg/ml to about 20.5 mg/ml NaCl.

E22. The pharmaceutical composition of embodiment E21, comprising about 16 mg/ml to about 19 mg/ml NaCl.

E23. The pharmaceutical composition of embodiment E22, comprising about 18.0 mg/ml NaCl.

E24. The pharmaceutical composition of any one of embodiments E1 to E23, comprising about 5 mM to about 15 mM L-histidine.

E25. The pharmaceutical composition of embodiment E24, comprising about 6.64 mM L-histidine or about 9.8 mM L-histidine.

E26. The pharmaceutical composition of any one of embodiments E1 to E23, comprising about 0.75 mg/ml to about 2.25 mg/ml L-histidine.

E27. The pharmaceutical composition of embodiment E26, the pharmaceutical composition comprises about 1.03 mg/ml L-histidine or about 1.55 mg/ml L-histidine.

E28. The pharmaceutical composition of any one of embodiments E1 to E27, comprising about 5 mM to about 10 mM calcium chloride.

E29. The pharmaceutical composition of embodiment E28, comprising about 5.4 mM calcium chloride or about 8 mM calcium chloride.

E30. The pharmaceutical composition of any one of embodiments E1 to E27, comprising about 0.75 mg/ml to about 1.5 mg/ml calcium chloride dihydrate.

E31. The pharmaceutical composition of embodiment E30, comprising about 0.8 mg/ml calcium chloride dihydrate or about 1.18 mg/ml calcium chloride dihydrate.

E32. The pharmaceutical composition of any one of embodiments E1 to E31, comprising about 0.008% (w/v) to about 0.025% (w/v) polysorbate 20 or polysorbate 80.

E33. The pharmaceutical composition of embodiment E32, comprising about 0.013% (w/v) polysorbate 20 or polysorbate 80 or about 0.02% (w/v) polysorbate 20 or polysorbate 80.

E34. The pharmaceutical composition of any one of embodiments E1 to E31, comprising about 0.08 mg/ml to about 0.25 mg/ml polysorbate 20 or polysorbate 80.

E35. The pharmaceutical composition of embodiment E34, comprising about 0.13% mg/ml polysorbate 20 or polysorbate 80 or about 0.20 mg/ml polysorbate 20 or polysorbate 80.

E36. The pharmaceutical composition of any one of embodiments E1 to E35, wherein the rFVIIIFc polypeptide comprises a first subunit comprising an amino acid sequence at least 90% or 95% identical to amino acids 20 to 1684 of SEQ ID NO:2 or 20 to 2578 of SEQ ID NO:6, and a second subunit comprising an amino acid sequence at least 90% to 95% identical to amino acids 21 to 247 of SEQ ID NO:4.

E37. The pharmaceutical composition of embodiment E36, wherein the rFVIIIFc polypeptide comprises a first subunit comprising amino acids 20 to 1684 of SEQ ID NO:2 or 20 to 2578 of SEQ ID NO:6, and a second subunit comprising amino acids 21 to 247 of SEQ ID NO:4.

E38. The pharmaceutical composition of any one of embodiments E1 to E37, wherein the FVIII polypeptide is present at a concentration of about 50 IU/ml to about 1500 IU/ml.

E39. The pharmaceutical composition of embodiment E38, comprising 83 IU/ml, 167 IU/ml, 250 IU/ml, 333 IU/ml, 500 IU/ml, 667 IU/ml, or 1000 IU/ml of the FVIII polypeptide.

E40. The pharmaceutical composition of any one of embodiments E1 to E37, wherein the FVIII polypeptide is present at a concentration of about 100 IU/ml to about 2500 IU/ml.

E41. The pharmaceutical composition of embodiment E40, comprising 150 IU/ml, 287.5 IU/ml, 431.25 IU/ml, 575 IU/ml, 862.5 IU/ml, 1150 IU/ml, or 1725 IU/ml of the FVIII polypeptide.

E42. The pharmaceutical composition of any one of embodiments E1 to E4, comprising:
(a) about 50 IU/ml to about 1500 IU/ml of the FVIII polypeptide;
(b) about 1% (w/v) to about 2.5% (w/v) of sucrose;
(c) about 150 mM to about 250 mM NaCl;
(d) about 5 mM to about 15 mM L-histidine;
(e) about 5 mM to about 10 mM calcium chloride; and
(f) about 0.008% (w/v) to about 0.025% of polysorbate 20 or polysorbate 80.

E43. The pharmaceutical composition of embodiment E42, comprising about 175 mM to about 225 mM NaCl.

E44. The pharmaceutical composition of embodiment E43, comprising about 200 mM to about 210 mM NaCl.

E45. The pharmaceutical composition of embodiment E44, comprising:
(a) about 83 IU/ml, about 167 IU/ml, about 250 IU/ml, about 333 IU/ml, about 500 IU/ml, about 667 IU/ml, or about 1000 IU/ml of the FVIII polypeptide;
(b) about 1.33% (w/v) of sucrose;
(c) about 205 mM NaCl;
(d) about 6.64 mM L-histidine;
(e) about 5.4 mM calcium chloride; and
(f) about 0.013% (w/v) of polysorbate 20 or polysorbate 80.

E46. The pharmaceutical composition of any one of embodiments E1 to E4, comprising:
(a) about 100 IU/ml to about 2500 IU/ml of the FVIII polypeptide;
(b) about 1% (w/v) to about 2.5% (w/v) of sucrose;
(c) about 250 mM to about 350 mM NaCl;
(d) about 5 mM to about 15 mM L-histidine;
(e) about 5 mM to about 10 mM calcium chloride; and
(f) about 0.008% (w/v) to about 0.025% of polysorbate 20 or polysorbate 80.

E47. The pharmaceutical composition of embodiment E46, comprising about 275 mM to about 325 mM NaCl.

E48. The pharmaceutical composition of embodiment E47, comprising:
(a) about 150 IU/ml, about 287.5 IU/ml, about 431.25 IU/ml, about 575 IU/ml, about 862.5 IU/ml, about 1150 IU/ml, or about 1725 IU/ml of the g FVIII polypeptide;
(b) about 2.0% (w/v) of sucrose;
(c) about 308 mM NaCl;
(d) about 9.8 mM L-histidine;
(e) about 8 mM calcium chloride; and
(f) about 0.020% (w/v) of polysorbate 20 or polysorbate 80.

E49. The pharmaceutical composition of any one of embodiments E1 to E4, comprising:
(a) about 50 IU/ml to about 1500 IU/ml of the FVIII polypeptide;
(b) about 10 mg/ml to about 25 mg/ml of sucrose;
(c) about 8.8 mg/ml to about 14.6 mg/ml NaCl;
(d) about 0.75 mg/ml to about 2.25 mg/ml L-histidine;
(e) about 0.75 mg/ml to about 1.5 mg/ml calcium chloride dihydrate; and
(f) about 0.08 mg/ml to about 0.25 mg/ml of polysorbate 20 or polysorbate 80.

E50. The pharmaceutical composition of embodiment E49, comprising about 10 mg/ml to 13 mg/ml NaCl.

E51. The pharmaceutical composition of embodiment E50, comprising:
(a) about 83 IU/ml, about 167 IU/ml, about 250 IU/ml, about 333 IU/ml, about 500 IU/ml, about 667 IU/ml, or about 1000 IU/ml of the FVIII polypeptide;
(b) about 13.3 mg/ml of sucrose;
(c) about 12.0 mg/ml NaCl;
(d) about 1.03 mg/ml L-histidine;
(e) about 0.8 mg/ml calcium chloride dihydrate; and
(f) about 0.13 mg/ml of polysorbate 20 or polysorbate 80.

E52. The pharmaceutical composition of any one of embodiments E1 to E4, comprising:
(a) about 100 IU/ml to about 2500 IU/ml of the FVIII polypeptide;
(b) about 10 mg/ml to about 25 mg/ml of sucrose;
(c) about 14.6 mg/ml to about 20.5 mg/ml NaCl;
(d) about 0.75 mg/ml to about 2.25 mg/ml L-histidine;
(e) about 0.75 mg/ml to about 1.5 mg/ml calcium chloride dihydrate; and
(f) about 0.08 mg/ml to about 0.25 mg/ml of polysorbate 20 or polysorbate 80.

E53. The pharmaceutical composition of embodiment E52, comprising about 16 mg/ml to about 19 mg/ml NaCl.

E54. The pharmaceutical composition of embodiment E53, comprising:
(a) about 150 IU/ml, about 287.5 IU/ml, about 431.25 IU/ml, about 575 IU/ml, about 862.5 IU/ml, about 1150 IU/ml, or about 1725 IU/ml of the FVIII polypeptide;
(b) about 20.0 mg/ml of sucrose;
(c) about 18.0 mg/ml NaCl;
(d) about 1.55 mg/ml L-histidine;

(e) about 1.18 mg/ml calcium chloride dihydrate; and
(f) about 0.20 mg/ml of polysorbate 20 or polysorbate 80.

E55. A pharmaceutical kit comprising:
(a) a first container comprising a lyophilized powder, where the powder comprises
  (i) the FVIII polypeptide,
  (ii) one or more stabilizing agents selected from the group consisting of sucrose, trehalose, raffinose, arginine, and mixture thereof;
  (iii) sodium chloride (NaCl);
  (iv) L-histidine;
  (v) calcium chloride; and
  (vi) polysorbate 20 or polysorbate 80; and
(b) a second container comprising sterilized water for injections to be combined with the lyophilized powder of the first container.

E56. The pharmaceutical kit of embodiment E55, wherein mannitol, glycine, alanine, or hydroxyethyl starch is not included.

E57. The pharmaceutical kit of embodiment E55 or E56, wherein NaCl is the only bulking agent.

E58. The pharmaceutical kit of any one of embodiments E55 to E57, comprising:
(a) a first container comprising a lyophilized powder, where the powder comprises
  (i) about 250 IU, about 500 IU, about 750 IU, about 1000 IU, about 1500 IU, about 2000 IU, or about 3000 IU of the FVIII polypeptide,
  (ii) about 40 mg of sucrose;
  (iii) about 36 mg of sodium chloride;
  (iv) about 3.1 mg of L-histidine;
  (v) about 2.40 mg of calcium chloride dihydrate; and
  (v) about 0.40 mg of polysorbate 20 or polysorbate 80; and
(b) a second container comprising sterilized water for injections at a volume sufficient to produce, when combined with the lyophilized powder of the first container, a solution comprising:
  (i) about 83 IU/ml, about 167 IU/ml, about 250 IU/ml, about 333 IU/ml, about 500 IU/ml, about 667 IU/ml, or about 1000 IU/ml of the FVIII polypeptide, respectively;
  (ii) about 1.33% (w/v) of sucrose;
  (iii) about 205 mM NaCl;
  (iv) about 6.64 mM L-histidine;
  (v) about 5.4 mM of calcium chloride; and
  (vi) about 0.013% (w/v) of polysorbate 20 or polysorbate 80.

E59. The pharmaceutical kit of any one of embodiments E55 to E57, comprising:
(a) a first container comprising a lyophilized powder, where the powder comprises
  (i) about 250 IU, about: 500 IU, about 750 IU, about 1000 IU, about 1500 IU, about 2000 IU, or about 3000 IU of the FVIII polypeptide,
  (ii) about 40 mg of sucrose;
  (iii) about 36 mg of sodium chloride;
  (iv) about 3.1 mg of L-histidine;
  (v) about 2.40 mg of calcium chloride dihydrate; and
  (v) about 0.40 mg of polysorbate 20 or polysorbate 80; and
(b) a second container comprising sterilized water for injections at a volume sufficient to produce, when combined with the lyophilized powder of the first container, a solution comprising:
  (i) about 83 IU/ml, about 167 IU/ml, about 250 IU/ml, about 333 IU/ml, about 500 IU/ml, about 667 IU/ml, or about 1000 IU/ml of the FVIII polypeptide, respectively;
  (ii) about 13.3 mg/ml of sucrose;
  (iii) about 12.0 mg/ml of NaCl;
  (iv) about 1.03 mg/ml of L-histidine;
  (v) about 0.80 mg/ml of calcium chloride; and
  (vi) about 0.13 mg/ml of polysorbate 20 or polysorbate 80.

E60. The pharmaceutical kit of any one of embodiments E55 to E59, wherein the first container is a glass vial comprising a rubber stopper.

E61. The pharmaceutical kit of any one of embodiments E55 to E112, wherein the second container is a syringe body, and wherein the syringe body is associated with a plunger.

E62. The pharmaceutical kit of embodiment E61, further comprising an adaptor to connect the glass vial to the syringe body.

E63. The pharmaceutical kit of embodiment E61 or E62, further comprising infusion tubing associated with a needle to be connected to the syringe, suitable for intravenous infusion.

E64. A method of reducing the annualized bleeding rate in a subject having hemophilia comprising administering to the subject the pharmaceutical composition of any one of embodiments E1 to E54 at a dosing interval of about three days or longer.

E65. The method of embodiment E64, wherein the administration is prophylactic and individualized for the subject resulting in an annualized bleeding rate less than about 5.0, less than about 4.9, less than about 4.8, less than about 4.7, less than about 4.6, or less than about 4.5.

E66. The method of embodiment E65, wherein the median annualized bleeding rate is about 1.6.

E67. The method of embodiment E64, wherein the administration is prophylactic and weekly resulting in an annualized bleeding rate less than about 9.0, less than about 8.9, less than about 8.8, less than about 8.7, less than about 8.6, less than about 8.5, or less than about 8.4.

E68. The method of embodiment E67, wherein the median annualized bleeding rate is about 3.6.

E69. The method of embodiment E64, wherein the administration is on-demand or episodic resulting in an annualized bleeding rate less than about 55, less than about 54, less than about 53, less than about 52, less than about 51, less than about 50, less than about 49, less than about 48, or less than about 47.

E70. The method of embodiment E69, wherein the median annualized bleeding rate is about 33.6.

E71. The method of any one of embodiments E64 to E70, wherein the effective dose is between about 20/IU/kg to about 90 IU/kg.

E72. The method of any one of embodiments E64 to E71, wherein the effective dose is 20-30 IU/kg, 30-40 IU/kg, 40-50 IU/kg, 50-60 IU/kg, 60-70 IU/kg, 70-80 IU/kg, or 80-90 IU/kg.

E73. The method of any one of embodiments E64 to E72, wherein the effective dose is 20 IU/kg, 25 IU/kg, 30 IU/kg, 35 IU/kg, 40 IU/kg, 45 IU/kg, 50 IU/kg, 55 IU/kg, 60 IU/kg, 65 IU/kg, 70 IU/kg, 75 IU/kg, 80 IU/kg, 85 IU/kg, or 90 IU/kg.

E74. The method of any of embodiments E71 to E73, wherein the administration is prophylactic and individualized at an effective dose of about 25 IU/kg to about 65 IU/kg twice weekly or every three days or about 50 IU/kg to about 65 IU/kg every 4 or 5 days.

E75. The method of embodiment E74, wherein a first dose of the FVIII polypeptide is administered is about 25 IU/kg and a second dose of the FVIII polypeptide is about 50 IU/kg.

E76. The method of any of embodiments E71 to E73, wherein the administration is prophylactic and weekly at an effective dose of 65 IU/kg weekly.

E77. The method of any of embodiments E71 to E73, wherein the administration is on-demand or episodic at an effective dose of 10 IU/kg to 75 IU/kg every 12 to 24 hours.

E78. The method of any one of embodiments E64 to E70, wherein the effective dose is a fixed dose, which is standard across all body weights.

E79. The method of embodiment E78, wherein the fixed dose is about 2,000 IU, about 2,500 IU, about 3,000 IU, about 3,500 IU, or about 4,000 IU per dose.

E80. The method of any one of embodiments E64 to E70, wherein the effective dose is a stratified dose.

E81. The method of any one of embodiments E64 to E70, wherein a trough level of the FVIII polypeptide is above 1%, above 2%, or above 3% of normal.

E82. The method of any one of embodiments E64 to E81, wherein the FVIII polypeptide has a $T_{1/2beta}$ (activity) of about 7 hours to about 48 hours, about 6 hours to about 49 hours, about 5 hours to about 50 hours.

E83. The method of any one of embodiment E82, wherein the FVIII has a $T_{1/2beta}$ (activity) mean of at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 25 hours.

E84. The method of embodiment E83, wherein the $T_{1/2beta}$ (activity) mean is about 19 hours.

E85. The method of embodiment E82 or E83, wherein the $T_{1/2beta}$ (activity) mean is at least about 1.5 fold higher than a polypeptide consisting of amino acids 20 to 1457 of SEQ ID NO:2, 20 to 2351 of SEQ ID NO: 6, or ADVATE®.

E86. The method of any one of embodiments E64 to E85, wherein the plasma trough level of the FVIII polypeptide is maintained between about 1% and about 5%, between about 1% and about 6%, between about 1% and about 7%, between about 1% and about 8%, between about 1% and about 9%, between about 1% and about 10%, between about 1% and about 11%, between about 1% and about 12%, between about 1% and about 13%, between about 1% and about 14%, between about 1% and about 15% above the baseline in the subject.

E87. The method of any one of embodiments E64 to E86, wherein the FVIII polypeptide is a long-acting FVIII polypeptide comprising a FVIII polypeptide and a heterologous moiety.

E88. The method of embodiment E87, wherein the heterologous moiety is an FcRn binding partner.

E89. The method of embodiment E88, wherein the FcRn binding partner comprises an Fc region.

E90. The method of embodiment E88 or E89, wherein the long-acting FVIII polypeptide further comprises a second FcRn binding partner.

E91. The method of embodiment E90, wherein the second FcRn binding partner comprises a second Fc region.

E92. The method of embodiment E90 or E91, wherein the FcRn binding partner and the second FcRn binding partner are associated.

E93. The method of embodiment E92, wherein the association is a covalent bond.

E94. The method of embodiment E93, wherein the covalent bond is a disulfide bond.

E95. The method of any one of embodiments E90 to E94, wherein the second FcRn binding partner is not linked to an amino acid sequence by a peptide bond.

E96. The method of any one of embodiments E64 to E95, wherein the long-acting FVIII polypeptide is FVIII monomer dimer hybrid.

E97. The method of any one of embodiments E87 to E96, wherein the FVIII polypeptide in the long-acting polypeptide is a human FVIII.

E98. The method of any one of embodiments E87 to E97, wherein the FVIII polypeptide in the long-acting polypeptide is a full-length FVIII or a B-domain deleted FVIII.

E99. The method of any one of embodiments E87 to E97, wherein the FVIII polypeptide is single chain.

E100. The method of any one of embodiments E87 to E97, wherein the FVIII polypeptide is unprocessed.

E101. The method of any one of embodiments E87 to E97, wherein the FVIII polypeptide is in two chains, a first chain comprising a heavy chain of the FVIII polypeptide and a second chain comprising a light chain of the FVIII polypeptide.

E102. The method of any one of embodiments E88 to E101, wherein the FcRn binding partner in the chimeric polypeptide is a human Fc.

E103. The method of any one of embodiments E87 to E102, wherein the FVIII polypeptide is at least 60%, 70%, 80%, 90%, 95%, 95%, 97%, 98%, 99%, or 100% identical to a FVIII amino acid sequence shown in Table 11A or 11B without a signal sequence (amino acids 20 to 1457 of SEQ ID NO: 2 or amino acids 20 to 2351 of SEQ ID NO: 6).

E104. The method of any one of embodiments E88 to E103, wherein the FcRn binding partner is at least 60%, 70%, 80%, 90%, 95%, 96%, 97%, 98%, 99%, or 100% identical to a Fc amino acid sequence shown in Table 11B without a signal sequence (amino acids 21 to 247 SEQ ID NO:4).

E105. The method of any one of embodiments E90 to E104, wherein the second FcRn binding partner in the chimeric polypeptide is a human Fc.

E106. The method of embodiment E105, wherein the second FcRn binding partner is at least 60%, 70%, 80%, 90%, 95%, 96%, 97%, 98%, 99%, or 100% identical to a Fc amino acid sequence shown in Table 11B without a signal sequence (amino acids 21 to 247 SEQ ID NO:4)

E107. The method of any one of embodiments E64 to E106, wherein the fixed dose of the clotting factor is for perioperative management of a bleeding episode.

E108. The method of any one of embodiments E64 to E107, wherein the subject is in need of controlling or preventing bleeding or bleeding episodes.

E109. The method of embodiment E108, wherein the subject is in need of controlling or preventing bleeding in minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitoneum, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain.

E110. The method of embodiment E109, wherein the subject is in need of management of bleeding associated with surgery or dental extraction.

E111. The method of embodiment E110, wherein the subject will undergo, is undergoing, or has undergone major surgery.

E112. The method of embodiment E111, wherein the major surgery is orthopedic surgery, extensive oral surgery, urologic surgery, or hernia surgery.

E113. The method of embodiment E112, wherein the orthopedic surgery is replacement of knee, hip, or other major joint.

E114. The method of any one of embodiments E64 to E113, wherein the subject is in need of long-term treatment.

E115. The method of any one of embodiments E64 to E114, wherein the FVIII polypeptide is administered intravenously or subcutaneously.

E116. The pharmaceutical composition of any one of embodiments E18-E23, E40, E41, E46-E48, and E52-E54, wherein the pharmaceutical composition is a pre-lyophilization composition.

E117. The pharmaceutical composition of any one of embodiments E1 to E37, wherein the FVIII polypeptide is present at a concentration of about 50 IU/ml to about 2500 IU/ml.

E118. The pharmaceutical composition of embodiment E117, comprising 1333 IU/ml, 1667 IU/ml, or 2000 IU/ml of the FVIII polypeptide.

E119. The pharmaceutical composition of any one of embodiments E1 to E37, wherein the FVIII polypeptide is present at a concentration of about 100 IU/ml to about 4500 IU/ml.

E120. The pharmaceutical composition of embodiment E119, comprising 2300 IU/ml, about 2875 IU/ml, or about 3450 IU/ml of the FVIII polypeptide.

E121. The pharmaceutical composition of any one of embodiments E1 to E4, comprising:
(a) about 50 IU/ml to about 2500 IU/ml of the FVIII polypeptide;
(b) about 1% (w/v) to about 2.5% (w/v) of sucrose;
(c) about 150 mM to about 250 mM NaCl;
(d) about 5 mM to about 15 mM L-histidine;
(e) about 5 mM to about 10 mM calcium chloride; and
(f) about 0.008% (w/v) to about 0.025% of polysorbate 20 or polysorbate 80.

E122. The pharmaceutical composition of embodiment E121, comprising about 175 mM to about 225 mM NaCl.

E123. The pharmaceutical composition of embodiment E122, comprising about 200 mM to about 210 mM NaCl.

E124. The pharmaceutical composition of embodiment E123, comprising:
(a) about 1333 IU/ml, about 1667 IU/ml, or about 2000 IU/ml of the FVIII polypeptide;
(b) about 1.33% (w/v) of sucrose;
(c) about 205 mM NaCl;
(d) about 6.64 mM L-histidine;
(e) about 5.4 mM calcium chloride; and
(f) about 0.013% (w/v) of polysorbate 20 or polysorbate 80.

E125. The pharmaceutical composition of any one of embodiments E1 to E4, comprising:
(a) about 100 IU/ml to about 4000 IU/ml of the FVIII polypeptide;
(b) about 1% (w/v) to about 2.5% (w/v) of sucrose;
(c) about 250 mM to about 350 mM NaCl;
(d) about 5 mM to about 15 mM L-histidine;
(e) about 5 mM to about 10 mM calcium chloride; and
(f) about 0.008% (w/v) to about 0.025% of polysorbate 20 or polysorbate 80.

E126. The pharmaceutical composition of embodiment E125, comprising about 275 mM to about 325 mM NaCl.

E127. The pharmaceutical composition of embodiment E126, comprising:
(a) about 2300 IU/ml, about 2875 IU/ml, or about 3450 IU/ml of the g FVIII polypeptide;
(b) about 2.0% (w/v) of sucrose;
(c) about 308 mM NaCl;
(d) about 9.8 mM L-histidine;
(e) about 8 mM calcium chloride; and
(f) about 0.020% (w/v) of polysorbate 20 or polysorbate 80.

E128. The pharmaceutical composition of any one of embodiments E1 to E4, comprising:
(a) about 50 IU/ml to about 2500 IU/ml of the FVIII polypeptide;
(b) about 10 mg/ml to about 25 mg/ml of sucrose;
(c) about 8.8 mg/ml to about 14.6 mg/ml NaCl;
(d) about 0.75 mg/ml to about 2.25 mg/ml L-histidine;
(e) about 0.75 mg/ml to about 1.5 mg/ml calcium chloride dihydrate; and
(f) about 0.08 mg/ml to about 0.25 mg/ml of polysorbate 20 or polysorbate 80.

E129. The pharmaceutical composition of embodiment E128, comprising about 10 mg/ml to 13 mg/ml NaCl.

E130. The pharmaceutical composition of embodiment E129, comprising:
(a) about 1333 IU/ml, about 1667 IU/ml, or about 2000 IU/ml of the FVIII polypeptide;
(b) about 13.3 mg/ml of sucrose;
(c) about 12.0 mg/ml NaCl;
(d) about 1.03 mg/ml L-histidine;
(e) about 0.8 mg/ml calcium chloride dihydrate; and
(f) about 0.13 mg/ml of polysorbate 20 or polysorbate 80.

E131. The pharmaceutical composition of any one of embodiments E1 to E4, comprising:
(a) about 100 IU/ml to about 4000 IU/ml of the FVIII polypeptide;
(b) about 10 mg/ml to about 25 m g/ml of sucrose;
(c) about 14.6 mg/ml to about 20.5 mg/ml NaCl;
(d) about 0.75 mg/ml to about 2.25 mg/ml L-histidine;
(e) about 0.75 mg/ml to about 1.5 mg/ml calcium chloride dihydrate; and
(f) about 0.08 mg/ml to about 0.25 mg/ml of polysorbate 20 or polysorbate 80.

E132. The pharmaceutical composition of embodiment E131, comprising about 16 mg/ml to about 19 mg/ml NaCl.

E133. The pharmaceutical composition of embodiment E1132, comprising:
(a) about 2300 IU/ml, about 2875 IU/ml, or about 3450 IU/ml of the FVIII polypeptide;
(b) about 20.0 mg/ml of sucrose;
(c) about 18.0 mg/ml NaCl;
(d) about 1.55 mg/ml L-histidine;
(e) about 1.18 mg/ml calcium chloride dihydrate; and
(f) about 0.20 mg/ml of polysorbate 20 or polysorbate 80.

E134. The pharmaceutical kit of any one of embodiments E55 to E57, comprising:
(a) a first container comprising a lyophilized powder, where the powder comprises
(i) about 4000 IU, about 5000 IU, or about 6000 IU of the FVIII polypeptide,
(ii) about 40 mg of sucrose;
(iii) about 36 mg of sodium chloride;

(iv) about 3.1 mg of L-histidine;
(v) about 2.40 mg of calcium chloride dihydrate; and
(v) about 0.40 mg of polysorbate 20 or polysorbate 80; and
(b) a second container comprising sterilized water for injections at a volume sufficient to produce, when combined with the lyophilized powder of the first container, a solution comprising:
(i) about 1333 IU/ml, about 1667 IU/ml, or about 2000 IU/ml of the FVIII polypeptide, respectively;
(ii) about 1.33% (w/v) of sucrose;
(iii) about 205 mM NaCl;
(iv) about 6.64 mM L-histidine;
(v) about 5.4 mM of calcium chloride; and
(vi) about 0.013% (w/v) of polysorbate 20 or polysorbate 80.

E135. The pharmaceutical kit of any one of embodiments E55 to E57, comprising:
(a) a first container comprising a lyophilized powder, where the powder comprises
(i) about 4000 IU, about 5000 IU, or about 6000 IU of the FVIII polypeptide,
(ii) about 40 mg of sucrose;
(iii) about 36 mg of sodium chloride;
(iv) about 3.1 mg of L-histidine;
(v) about 2.40 mg of calcium chloride dihydrate; and
(v) about 0.40 mg of polysorbate 20 or polysorbate 80; and
(b) a second container comprising sterilized water for injections at a volume sufficient to produce, when combined with the lyophilized powder of the first container, a solution comprising:
(i) about 1333 IU/ml, about 1667 IU/ml, or about 2000 IU/ml of the FVIII polypeptide, respectively;
(ii) about 13.3 mg/ml of sucrose;
(iii) about 12.0 mg/ml of NaCl;
(iv) about 1.03 mg/ml of L-histidine;
(v) about 0.80 mg/ml of calcium chloride; and
(vi) about 0.13 mg/ml of polysorbate 20 or polysorbate 80.

E136. The pharmaceutical kit of any one of embodiments E134 to E135, wherein the first container is a glass vial comprising a rubber stopper.

E137. The pharmaceutical kit of any one of embodiments E134 to E136, wherein the second container is a syringe body, and wherein the syringe body is associated with a plunger.

E138. The pharmaceutical kit of embodiment E137, further comprising an adaptor to connect the glass vial to the syringe body.

E139. The pharmaceutical kit of embodiment E137 or E138, further comprising infusion tubing associated with a needle to be connected to the syringe, suitable for intravenous infusion.

E140. A method of treating a bleeding disorder in a subject having hemophilia comprising administering to the subject the pharmaceutical composition of any one of embodiments E117 to E133 at a dosing interval of about three days or longer.

E141. The method of embodiment E140, wherein the pharmaceutical composition is administered for individual prophylaxis of hemophilia.

E142. The method of embodiment E140, wherein the pharmaceutical composition is administered for weekly prophylaxis of hemophilia.

E143. The method of embodiment E140, wherein the pharmaceutical composition is administered for episodic (on-demand) treatment of hemophilia.

E144. The method of embodiment E140, wherein the pharmaceutical composition is administered for perioperative management of hemophilia.

TABLE 10

Polynucleotide Sequences

A. B-Domain Deleted FVIIIFc
(i) B-Domain Deleted FVIIIFc Chain DNA Sequence (FVIII signal peptide underlined. Fc region in bold) (SEQ ID NO: 1, which encodes SEQ ID NO: 2)

```
 661                                    A TGCAAATAGA GCTCTCCACC TGCTTCTTTC

721 TGTGCCTTTT GCGATTCTGC TTTAGTGCCA CCAGAAGATA CTACCTGGGT GCAGTGGAAC

781 TGTCATGGGA CTATATGCAA AGTGATCTCG GTGAGCTGCC TGTGGACGCA AGATTTCCTC

841 CTAGAGTGCC AAAATCTTTT CCATTCAACA CCTCAGTCGT GTACAAAAAG ACTCTGTTTG

901 TAGAATTCAC GGATCACCTT TTCAACATCG CTAAGCCAAG GCCACCCTGG ATGGGTCTGC

961 TAGGTCCTAC CATCCAGGCT GAGGTTTATG ATACAGTGGT CATTACACTT AAGAACATGG

1021 CTTCCCATCC TGTCAGTCTT CATGCTGTTG GTGTATCCTA CTGGAAAGCT TCTGAGGGAG

1081 CTGAATATGA TGATCAGACC AGTCJAAGGG AGAAAGAAGA TGATAAAGTC TTCCCTGGTG

1141 GAAGCCATAC ATATGTCTGG CAGGTCCTGA AAGAGAATGG TCCAATGGCC TCTGACCCAC

1201 TGTGCCTTAC CTACTCATAT CTTTCTCATG TGGACCTGGT AAAAGACTTG AATTCAGGCC

1261 TCATTGGAGC CCTACTAGTA TGTAGAGAAG GGAGTCTGGC CAAGGAAAAG ACACAGACCT

1321 TGCACAAATT TATACTACTT TTTGCTGTAT TTGATGAAGG GAAAAGTTGG CACTCAGAAA

1381 CAAAGAACTC CTTGATGCAG GATAGGGATG CTGCATCTGC TCGGGCCTGG CCTAAAATGC

1441 ACACAGTCAA TGGTTATGTA AACAGGTCTC TGCCAGGTCT GATTGGATGC CACAGGAAAT
```

TABLE 10-continued

Polynucleotide Sequences

```
1501 CAGTCTATTG GCATGTGATT GGAATGGGCA CCACTCCTGA AGTGCACTCA ATATTCCTCG
1561 AAGGTCACAC ATTTCTTGTG AGGAACCATC GCCAGGCGTC CTTGGAAATC TCGCCAATAA
1621 CTTTCCTTAC TGCTCAAACA CTCTTGATGG ACCTTGGACA GTTTCTACTG TTTTGTCATA
1681 TCTCTTCCCA CCAACATGAT GGCATGGAAG CTTATGTCAA AGTAGACAGC TGTCCAGAGG
1741 AACCCCAACT ACGAATGAAA AATAATGAAG AAGCGGAAGA CTATGATGAT GATCTTACTG
1801 ATTCTGAAAT GGATGTGGTC AGGTTTGATG ATGACAACTC TCCTTCCTTT ATCCAAATTC
1861 GCTCAGTTGC CAAGAAGCAT CCTAAAACTT GGGTACATTA CATTGCTGCT GAAGAGGAGG
1921 ACTGGGACTA TGCTCCCTTA GTCCTCGCCC CCGATGACAG AAGTTATAAA AGTCAATATT
1981 TGAACAATGG CCCTCAGCGG ATTGGTAGGA AGTACAAAAA AGTCCGATTT ATGGCATACA
2041 CAGATGAAAC CTTTAAGACT CGTGAAGCTA TTCAGCATGA ATCAGGAATC TTGGGACCTT
2101 TACTTTATGG GGAAGTTGGA GACACACTGT TGATTATATT TAAGAATCAA GCAAGCAGAC
2161 CATATAACAT CTACCCTCAC GGAATCACTG ATGTCCGTCC TTTGTATTCA AGGAGATTAC
2221 CAAAAGGTGT AAAACATTTG AAGGATTTTC CAATTCTGCC AGGAGAAATA TTCAAATATA
2281 AATGGACAGT GACTGTAGAA GATGGGCCAA CTAAATCAGA TCCTCGGTGC CTGACCCGCT
2341 ATTACTCTAG TTTCGTTAAT ATGGAGAGAG ATCTAGCTTC AGGACTCATT GGCCCTCTCC
2401 TCATCTGCTA CAAAGAATCT GTAGATCAAA GAGGAAACCA GATAATGTCA GACAAGAGGA
2461 ATGTCATCCT GTTTTCTGTA TTTGATGAGA ACCGAAGCTG GTACCTCACA GAGAATATAC
2521 AACGCTTTCT CCCCAATCCA GCTGGAGTGC AGCTTGAGGA TCCAGAGTTC CAAGCCTCCA
2581 ACATCATGCA CAGCATCAAT GGCTATGTTT TTGATAGTTT GCAGTTGTCA GTTTGTTTGC
2641 ATGAGGTGGC ATACTGGTAC ATTCTAAGCA TTGGAGCACA GACTGACTTC CTTTCTGTCT
2701 TCTTCTCTGG ATATACCTTC AAACACAAAA TGGTCTATGA AGACACACTC ACCCTATTCC
2761 CATTCTCAGG AGAAACTGTC TTCATGTCGA TGGAAAACCC AGGTCTATGG ATTCTGGGGT
2821 GCCACAACTC AGACTTTCGG AACAGAGGCA TGACCGCCTT ACTGAAGGTT TCTAGTTGTG
2881 ACAAGAACAC TGGTGATTAT TACGAGGACA GTTATGAAGA TATTTCAGCA TACTTGCTGA
2941 GTAAAAACAA TGCCATTGAA CCAAGAAGCT CTCTCAAAA CCCACCAGTC TTGAAACGCC
3001 ATCAACGGGA ATAACTCGT ACTACTCTTC AGTCAGATCA AGAGGAAATT GACTATGATG
3061 ATACCATATC AGTTGAAATG AAGAAGGAAG ATTTTGACAT TTATGATGAG GATGAAAATC
3121 AGAGCCCCCG CAGCTTTCAA AAGAAAACAC GACACTATTT TATTGCTGCA GTGGAGAGGC
3181 TCTGGGATTA TGGGATGAGT AGCTCCCCAC ATGTTCTAAG AAACAGGGCT CAGAGTGGCA
3241 GTGTCCCTCA GTTCAAGAAA GTTGTTTTCC AGGAATTTAC TGATGGCTCC TTTACTCAGC
3301 CCTTATACCG TGGAGAACTA AATGAACATT TGGGACTCCT GGGGCCATAT ATAAGAGCAG
3361 AAGTTGAAGA TAATATCATG GTAACTTTCA GAAATCAGGC CTCTCGTCCC TATTCCTTCT
3421 ATTCTAGCCT TATTTCTTAT GAGGAAGATC AGAGGCAAGG AGCAGAACCT AGAAAAAACT
3481 TTGTCAAGCC TAATGAAACC AAAACTTACT TTTGGAAAGT GCAACATCAT ATGGCACCCA
3541 CTAAAGATGA GTTTGACTGC AAAGCCTGGG CTTATTTCTC TGATGTTGAC CTGGAAAAAG
3601 ATGTGCACTC AGGCCTGATT GGACCCCTTC TGGTCTGCCA CACTAACACA CTGAACCCTG
3661 CTCATGGGAG ACAAGTGACA GTACAGGAA1 TTGCTCTGTT TTTCACCATC TTTGATGAGA
3721 CCAAAAGCTG GTACTTCACT GAAAATATGG AAAGAAACTG CAGGGCTCCC TGCAATATCC
3781 AGATGGAAGA TCCCACTTTT AAAGAGAATT ATCGCTTCCA TGCAATCAAT GGCTACATAA
```

TABLE 10-continued

Polynucleotide Sequences

3841 TGGATACACT ACCTGGCTTA GTAATGGCTC AGGATCAAAG GATTCGATGG TATCTGCTCA

3901 GCATGGGCAG CAATGAAAAC ATCCATTCTA TTCATTTCAG TGGACATGTG TTCACTGTAC

3961 GAAAAAAGA GGAGTATAAA ATGGCACTGT ACAATCTCTA TCCAGGTGTT TTTGAGACAG

4021 TGGAAATGTT ACCATCCAAA GCTGGAATTT GGCGGGTGGA ATGCCTTATT GGCGAGCATC

4081 TACATGCTGG GATGAGCACA CTTTTTCTGG TGTACAGCAA TAAGTGTCAG ACTCCCCTGG

4141 GRATGGCTTC TGGACACATT AGAGATTTTC AGATTACAGC TTCAGGACAA TATGGACAGT

4201 GGGCCCCAAA GCTGGCCAGA CTTCATTATT CCGGATCAAT CAATGCCTGG AGCACCAAGG

4261 AGCCCTTTTC TTGGATCAAG GTGGATCTGT TGGCACCAAT GATTATTCAC GGCATCAAGA

4321 CCCAGGGTGC CGTCAGAAG TTCTCCAGCC TCTACATCTC TCAGTTTATC ATCATGTATA

4381 GTCTTGATGG AAGAAGTGG CAGACTTATC GAGGAAATTC CACTGGARCC TTAATGGTCT

4441 TCTTTGGCAA TGTGGATTCA TCTGGGATAA ACACAATAT TTTTAACCCT CCAATTATTG

4501 CTCGATACAT CCGTTTGCAC CCAACTCATT ATAGCATTCG CAGCACTCTT CGCATGGAGT

4561 TGATGGGCTG TGATTTAAAT AGTTGCAGCA TGCATTGGG AATGGAGAGT AAAGCAATAT

4621 CAGATGCACA GATTACTGCT TCATCCTACT TTACCAATAT GTTTGCCACC TGGTCTCCTT

4681 CAAAAGCTCG ACTTCACCTC CAAGGGAGGA GTAATGCCTG GAGACCTCAG GTGAATAATC

4741 CAAAAGAGTG GCTGCAAGTG GACTTCCAGA AGACAATGAA AGTCACAGGA GTAACTACTC

4801 AGGGAGTAAA ATCTCTGCTT ACCAGCATGT ATGTGAAGGA GTTCCTCATC TCCAGCAGTC

4861 AAGATGGCCA TCAGTGGACT CTCTTTTTTC AGAATGGCAA AGTAAAGGTT TTTCAGGGAA

4921 ATCAAGACTC CTTCACACCT GTGGTGAACT CTCTAGACCC ACCGTTACTG ACTCGCTACC

4981 TTCGAATTCA CCCCCAGAGT TGGGTGCACC AGATTGCCCT GAGGATGGAG GTTCTGGGCT

5041 GCGAGGCACA GGACCTCTAC GACAAAACTC ACACATGCCC ACCGTGCCCA GCTCCAGAAC

5101 TCCTGGGCGG ACCGTCAGTC TTCCTCTTCC CCCCAAAACC CAAGGACACC CTCATGATCT

5161 CCCGGACCCC TGAGGTCACA TGCGTGGTGG TGGACGTGAG CCACGAAGAC CCTGAGGTCA

5221 AGTTCAACTG GTACGTGGAC GGCGTGGAGG TGCATAATGC CAAGACAAAG CCGCGGGAGG

5281 AGCAGTACAA CAGCACGTAC CGTGTGGTCA GCGTCCTCAC CGTCCTGCAC CAGGACTGGC

5341 TGAATGGCAA GGAGTACAAG TGCAAGGTCT CCAACAAAGC CCTCCCAGCC CCCATCGAGA

5401 AAACCATCTC CAAAGCCAAA GGGCAGCCCC GAGAACCACA CGTGTACACC CTGCCCCCAT

5461 CCCGGGATGA GCTGACCAAG AACCAGGTCA GCCTGACCTG CCTGGTCAAA GGCTTCTATC

5521 CCAGCGACAT CGCCGTGGAG TGGGAGAGGA ATCGGCAGCC GGAGAACAAC TACAAGACCA

5581 CGCCTCCQGT GTTGGACTCC GAGGGCTCCT TCTTCCTCTA CAGCAAGCTC ACCPTGGACA

5641 AGAGCAGGTG GCAGCAGGGG AACGTCTTCT CATGCTCCGT GATGCATGAG GCTCTGCACA

5701 ACCACTACAC GCAGAAGAGC CTCTCCCTGT CTCCGGGTAA A

(ii) Fc DNA sequence (mouse Igκ signal peptide underlined)
(SEQ ID NO: 3, which encodes SEQ ID NO: 4)

7981                                             <u>ATGGA GACAGACACA</u>

8041 <u>CTCCTGCTAT GGGTACTGCT GCTCTGGGTT CCAGGTTCCA CTGGTGACAA</u> AACTCACACA

8101 TGCCCACCGT GCCCAGCACC TGAACTCCTG GGAGGACCGT CAGTCTTCCT CTTCCCCCCA

8161 AAACCCAAGG ACACCCTCAT GATCTCCCGG ACCCCTGAGG TCACATGCGT GGTGGTGGAC

8221 GTGAGCCACG AAGACCCTGA GGTCAAGTTC AACTGGTACG TGGACGGCGT GGAGGTGCAT

8281 AATGCCAAGA CAAAGCCGCG GGAGGAGCAG TACAACAGCA CGTACCGTGT GGTCAGCGTC

TABLE 10-continued

Polynucleotide Sequences

8341 CTCACCGTCC TGCACCAGGA CTGGCTGAAT GGCAAGGAGT ACAAGTGCAA GGTCTCCAAC

8401 AAAGCCCTCC CAGCCCCCAT CGAGAAAACC ATCTCCAAAG CCAAAGGGCA GCCCCGAGAA

8461 CCACAGGTGT ACACCCTGCC CCCATCCCGC GATGAGCTGA CCAAGAACCA GGTCAGCCTG

8521 ACCTGCCTGG TCAAAGGCTT CTATCCCAGC GACATCGCCG TGGAGTGGGA GAGCAATGGG

8581 CAGCCGGAGA ACAACTACAA GACCACGCCT CCCGTGTTGG ACTCCGACGG CTCCTTCTTC

8641 CTCTACAGCA AGCTCACCGT GGACAAGAGC AGGTGGCAGC AGGGGAACGT CTTCTCATGC

8701 TCCGTGATGC ATGAGGCTCT GCACAACCAC TACACGCAGA AGAGCCTCTC CCTGTCTCCG

8761 GGTAAA

B. Full Length FVIIIFc
(i) Full Length FVIIIFc DNA Sequence (FVIII signal peptide underlined. Fc region in bold) (SEQ ID NO: 5, which encodes SEQ ID NO: 6)

661                                                    ATG CAAATAGAGC TCTCCACCTG

721 CTTCTTTCTG TGCCTTTTGC GATTCTGCTT TAGTGCCACC AGAAGATACT ACCTGGGTGC

781 AGTGGAACTG TCATGGGACT ATATGCAAAG TGATCTCGGT GAGCTGCCTG TGGACGCAAG

841 ATTTCCTCCT AGAGTGCCAA AATCTTTTCC ATTCAACACC TCAGTCGTGT ACAAAAAGAC

901 TCTGTTTGTA GAATTCACGG ATCACCTTTT CAACATCGCT AAGCCAAGGC CACCCTGGAT

961 GGGTCTGCTA GGTCCTACCA TCCAGGCTGA GGTTTATGAT ACAGTGGTCA TTACACTTAA

1021 GAACATGGCT TCCCATCCTG TCAGTCTTCA TGCTGTTGGT GTATCCTACT GGAAAGCTTC

1081 TGAGGGAGCT GAATATGATG ATCAGACCAG TCAAAGGGAG AAAGAAGATG ATAAAGTCTT

1141 CCCTGGTGGA AGCCATACAT ATGTCTGGCA GGTCCTGAAA GAGAATGGTC CAATGGCCTC

1201 TGACCCACTG TGCCTTACCT ACTCATATCT TTCTCATGTG GACCTGGTAA AAGACTTGAA

1261 TTCAGGCCTC ATTGGAGCCC TACTAGTATG TAGAGAAGGG AGTCTGGCCA GGAAAAAGAC

1321 ACAGACCTTG CACAAATTTA TACTACTTTT TGCTGTATTT GATGAAGGGA AAAGTTGGCA

1381 CTCAGAAACA AAGAACTCCT TGATGCAGGA TAGGGATGCT GCATCTGCTC GGGCCTGGCC

1441 TAAAATGCAC ACAGTCAATG GTTATGTAAA CAGGTCTCTG CCAGGTCTGA TTGGATGCCA

1501 CAGGAAATCA GTCTATTGGC ATGTGATTGG AATGGGCACC ACTCCTGAAG TGCACTCAAT

1561 ATTCCTCGAA GGTCACACAT TTCTTGTGAG GAACCATCGC CAGGCGTCCT TGGAAATCTC

1621 GCCAATAACT TTCCTTACTG CTCAAACACT CTTGATGGAC CTTGGACAGT TTCTACTGTT

1681 TTGTCATATC TCTTCCCACC AACATGATGG CATGGAAGCT TATGTCAAAG TAGACAGCTG

1741 TCCAGAGGAA CCCCAACTAC GAATGAAAAA TAATGAAGAA GCGGAAGACT ATGATGATGA

1801 TCTTACTGAT TCTGAAATGG ATGTGGTCAG GTTTGATGAT GACAACTCTC CTTCCTTTAT

1861 CCAAATTCGC TCAGTTGCCA AGAAGCATCC TAAAACTTGG GTACATTACA TTGCTGCTGA

1921 AGAGGAGGAC TGGGACTATG CTCCCTTAGT CCTCGCCCCC GATGACAGAA GTTATAAAAG

1981 TCAATATTTG AACAATGGCC CTCAGCGGAT TGGTAGGAAG TACAAAAAAG TCCGATTTAT

2041 GGCATACACA GATGAAACCT TTAAGACTCG TGAAGCTATT CAGCATGAAT CAGGAATCTT

2101 GGGACCTTTA CTTTATGGGG AAGTTGGAGA CACACTGTTG ATTATATTTA AGAATCAAGC

2161 AAGCAGACCA TATAACAiCT ACCCTCACGG AATCACTGAT GTCCGTCCTT TGTATTCAAG

2221 GAGATTACCA AAAGGTGTAA ACATTTGAA GGATTTTCCA ATTCTGCCAG AGAAATATT

2281 CAAATATAAA TGGACAGTGA CTGTAGAAGA TGGGCCAACT AAATCAGATC CTCGGTGCCT

2341 GACCCGCTAT TACTCTAGTT TCGTTAATAT GGAGAGAGAT CTAGCTTCAG GACTCATTGG

TABLE 10-continued

Polynucleotide Sequences

```
2401 CCCTCTCCTC ATCTGCTACA AAGAATCTGT AGATCAAAGA GGAAACCAGA TAATGTCAGA
2461 CAAGAGGAAT GTCATCCTGT TTTCTGTATT TGATGAGAAC CGAAGCTGGT ACCTCACAGA
2521 GAATATACAA CGCTTTCTCC CCAATCCAGC TGGAGTGCAG CTTGAGGATC CAGAGTTCCA
2581 AGCCTCCAAC ATCATGCACA GCATCAATGG CTATGTTTTT GATAGTTTGC AGTTGTCAGT
2641 TTGTTTGCAT GAGGTGGCAT ACTGGTACAT TCTAAGCATT GGAGCACAGA CTGACTTCCT
2701 TTCTGTCTTC TTCTCTGGAT ATACCTTCAA ACACAAAATG GTCTATGAAG ACACACTCAC
2761 CCTATTCCCA TTCTCAGGAG AAACTGTCTT CATGTCGATG GAAAACCCAG GTCTATGGAT
2821 TCTGGGGTGC CACAACTCAG ACTTTCGGAA CAGAGGCATG ACCGCCTTAC TGAAGGTTTC
2881 TAGTTGTGAC AAGAACACTG GTGATTATTA CGAGGACAGT TATGAAGATA TTTCAGCATA
2941 CTTGCTGAGT AAAAACAATG CCATTGAACC AAGAAGCTTC TCCCAGAATT CAAGACACCC
3001 TAGCACTAGG CAAAAGCAAT TTAATGCCAC CACAATTCCA GAAATGACA TAGAGAAGAC
3061 TGACCCTTGG TTTGCACACA GAACACCTAT GCCTAAAATA CAAATGTCT CCTCTAGTGA
3121 TTTGTTGATG CTCTTGCGAC AGAGTCCTAC TCCACATGGG CTATCCTTAT CTGATCTCCA
3181 AGAAGCCAAA TATGAGACTT TTTCTGATGA TCCATCACCT GGAGCAATAG ACAGTAATAA
3241 CAGCCTGTCT GAAATGACAC ACTTCAGGCC ACAGCTCCAT CACAGTGGGG ACATGGTATT
3301 TACCCCTGAG TCAGGCCTCC AATTAAGATT AAATGAGAAA CTGGGGACAA CTGCAGCAAC
3361 AGAGTTGAAG AAACTTGATT TCAAAGTTTC TAGTACATCA AATAATCTGA TTTCAACAAT
3421 TCCATCAGAC AATTTGGCAG CAGGTACTGA TAATACAAGT TCCTTAGGAC CCCCAAGTAT
3481 GCCAGTTCAT TATGATAGTC AATTAGATAC CACTCTATTT GGCAAAAAGT CATCTCCCCT
3541 TACTGAGTCT GGTGGACCTC TGAGCTTGAG TGAAGAAAAT AATGATTCAA AGTTGTTAGA
3601 ATCAGGTTTA ATGAATAGCC AAGAAAGTTC ATGGGGAAAA AATGTATCGT CAACAGAGAG
3661 TGGTAGGTTA TTTAAAGGGA AAAGAGCTCA TGGACCTGCT TTGTTGACTA AAGATAATGC
3721 CTTATTCAAA GTTAGCATCT CTTTGTTAAA GACAAACAAA ACTTCCAATA ATTCAGCAAC
3781 TAATAGAAAG ACTCACATTG ATGGCCCATC ATTATTAATT GAGAATAGTC CATCAGTCTG
3841 GCAAAATATA TTAGAAAGTG ACACTGAGTT TAAAAAAGTG ACACCTTTGA TTCATGACAG
3901 AATGCTTATG GACAAAAATG CTACAGCTTT GAGGCTAAAT CATATGTCAA ATAAAACTAC
3961 TTCATCAAAA AACATGGAAA TGGTCCAACA GAAAAAAGAG GGCCCCATTC CACCAGATGC
4021 ACAAATCCA GATATGTCGT TCTTTAAGAT GCTATTCTTG CCAGAATCAG CAAGGTGGAT
4081 ACAAAGGACT CATGGAAAGA ACTCTCTGAA CTCTGGGCAA GGCCCAGTC CAAAGCAATT
4141 AGTATCCTTA GGACCAGAAA AATCTGTGGA AGGTCAGAAT TCTTGTCTG AGAAAAACAA
4201 AGTGGTAGTA GGAAAGGGTG AATTTACAAA GGACGTAGGA CTCAAAGAGA TGGTTTTTCC
4261 AAGCAGCAGA AACCTATTTC TTACTAACTT GGATAATTTA CATGAAAATA ATACACACAA
4321 TCAAGAAAAA AAAATTCAGG AAGAAATAGA AAGAAGGAA ACATTAATCC AAGAGAATGT
4381 AGTTTTGCCT CAaATACATA CACTGACTGG CACTAAGAAT TTCATGAAGA ACCTTTTCTT
4441 ACTGAGCACT AGGCAAAATG TAGAAGGTTC ATATGACGGG GCATATGCTC CAGTACTTCA
4501 AGATTTTAGG TCATTAAATG ATTCAACAAA TAGAACAAAG AAACACACAG CTCATTTCTC
4561 AAAAAAAGGG GAGGAAGAAA ACTTGGAAGG CTTGGGAAAT CAAACCAAGC AAATTGTAGA
4621 GAAATATGCA TGCACCACAA GGATATCTCC TAATACAAGC CAGCAGAATT TTGTCACGCA
4681 ACGTAGTAAG AGAGCTTTGA AACAATTCAG ACTCCCACTA GAAGAAACAC AACTTGAAAA
```

TABLE 10-continued

| Polynucleotide Sequences |
|---|
| 4741 AAGGATAATT GTGGATGACA CCTCAACCCA GTGGTCCAAA GACATGAAAC ATTTGACCCC |
| 4801 GAGCACCCTC ACACAGATAG ACTACAATGA GAAGGAGAAA GGGGCCATTA CTCAGTCTCC |
| 4861 CTTATCAGAT TGCCTTACGA GGAGTCATAG CATCCCTCAA GCAAATAGAT CTCCATTACC |
| 4921 CATTGCAAAG GTATCATCAT TTCCATCTAT TAGACCTATA TATCTGACCA GGGTCCTATT |
| 4981 CCAAGACAAC TCTTCTCATC TTCCAGCAGC ATCTTATAGA AAGAAAGATT CTGOGGTCCA |
| 5041 AGAAAGCAGT CATTTCTTAC AAGGAGCCAA AAAAATAAC CTTTCTTTAG CCATTCTAAC |
| 5101 CTTGGAGATG ACTGGTGATC AAAGAGAGGT TGGCTCCCTG GCACAAGTG CCACAAATTC |
| 5161 AGTCACATAC AAGAAAGTTG AGAACACTGT TCTCCCGAAA CCAGACTTGC CCAAAACATC |
| 5221 TGGCAAAGTT GAATTGCTTC CAAAAGTTCA CATTTATCAG AAGGACCTAT TCCCTACGGA |
| 5281 AACTAGCAAT GGGTCTCCTG GCCATCTGGA TCTCGTGGAA GGGAGCCTTC TTCAGGGAAC |
| 5341 AGAGGGAGCG ATTAAGTGGA ATGAAGCAAA CAGACCTGaA AAAGTTCCCT TTCTGAGAGT |
| 5401 AGCAACAGAA ACCTCTOCAA AGACTCCCTC CAAGCTATTG GATCCTCTTG CTTGGGATAA |
| 5461 CCACTATGGT ACTCAGATAC CAAAAGAAGA GTGGARATCC CAAGAGAAGT CACCAGAAAA |
| 5521 AACAGCTTTT AAGAAAAAGG ATACCATTTT GTCCCTGAAC GCTTGTGAAA GCAATCATGC |
| 5581 AATAGCAGCA ATAAATGAGG GACAAAATAA GCCCGAAATA GAAGTCACCT GGGCAAAGCA |
| 5641 AGGTAGGACT GAAAGGCTGT GCTCTCAAAA CCCACCAGTC TTGAAACGCC ATCAACGGGA |
| 5701 AATAACTCGT ACTACTCTTC AGTCAGATCA AGAGGAAATT GACTATGATG ATACCATATC |
| 5761 AGTTGAAATG AAGAAGGAAG ATTTTGACAT TTATGATGAG GATGAAAATC AGAGCCCCCG |
| 5821 CAGCTTTCAA AAGAAAACAC GACACTATTT TATTGCTGCA GTGGAGAGGC TCTGGGATTA |
| 5881 TGGGATGAGT AGCTCCCCAC ATGTTCTAAG AAACAGGGCT CAGAGTGGCA GTGTCCCTCA |
| 5941 GTTCAAGAAA GTTGTTTTCC AGGAATTTAC TGATGGCTCC TTTACTCAGC CCTTATACCG |
| 6001 TGGAGAACTA AATGAACATT TGGGACTCCT GGGGCCATAT ATAAGAGCAG AAGTTGAAGA |
| 6061 TAATATCATG GTAACTTTCA GAAATCAGGC CTCTCGTCCC TATTCCTTCT ATTCTAGCCT |
| 6121 TATTTCTTAT GAGGAAGATC AGAGGCAAGG AGCAGAACCT AGAAAAAACT TTGTCAAGCC |
| 6181 TAATGAAACC AAAACTTACT TTTGGAAAGT GCAACATCAT ATGGCACCCA CTAAAGATGA |
| 6241 GTTTGACTGC AAAGCCTGGG CTTATTTCTC TGATGTTGAC CTGGAAAAAG ATGTGCACTC |
| 6301 AGGCCTGATT GGACCCCTTC TGGTCTGCCA CACTAACACA CTGAACCCTG CTCATGGGAG |
| 6361 ACAAGTGACA GTACAGGAAT TGCTCTGTT TTTCACCATC TTTGATGAGA CCAAAAGCTG |
| 6421 GTACTTCACT GAAAATATGG AAAGAAACTG CAGGGCTCCC TGCAATATCC AGATGGAAGA |
| 6481 TCCCACTTTT AAAGAGAATT ATCGCTTCCA TGCAATCAAT GGCTACATAA TGGATACACT |
| 6541 ACCTGGCTTA GTAATGGCTC AGGATCAAAG GATTCGATGG TATCTGCTCA GCATGGGCAG |
| 6601 CAATGAAAAC ATCCATTCTA TTCATTTCAG TGGACATGTG TTCACTGTAC GAAAAAAAGA |
| 6661 GGAGTATAAA ATGGCACTGT ACAATCTCTA TCCAGGTGTT TTTGAGACAG TGGAAATGTT |
| 6721 ACCATCCAAA GCTGGAATTT GGCGGGTGGA ATGCCTTATT GGCGAGCATC TACATGCTGG |
| 6781 GATGAGCACA CTTTTTCTGG TGTACAGCAA TAAGTGTCAG ACTCCCCTGG GAATGGCTTC |
| 6841 TGGACACATT AGAGATTTTC AGATTACAGC TTCAGGACAA TATGGACAGT GGGCCCCAAA |
| 6901 GCTGGCCAGA CTTCATTATT CCGGATCAAT CAATGCCTGG AGCACCAAGG AGCCCTTTTC |
| 6961 TTGGATCPAG GTGGATCTGT TGGCACCAAT GATTATTCAC GGCATCAAGA CCCAGGGTGC |
| 7021 CCGTCAGAAG TTCTCCAGCC TCTACATCTC TCAGTTTATC ATCATGTATA GTCTTGATGG |

TABLE 10-continued

Polynucleotide Sequences

```
7081 GAAGAAGTGG CAGACTTATC GAGGAAATTC CACTGGAACC TTAATGGTCT TCTTTGGCAA

7141 TGTGGATTCA TCTGGGATAA AACACAATAT TTTTAACCCT CCAATTATTG CTCGATACAT

7201 CCGTTTGCAC CCAACTCATT ATAGCATTCG CAGCACTCTT CGCATGGAGT TGATGGGCTG

7261 TGATTTAAAT AGTTGCAGCA TGCCATTGGG AATGGAGAGT AAAGCAATAT CAGATGCACA

7321 GATTACTGCT TCATCCTACT TTACCAATAT GTTTGCCACC TGGTCTCCTT CAAAAGCTCG

7381 ACTTCACCTC CAAGGGAGGA GTAATGCCTG GAGACCTCAG GTGAATAATC AAAAGAGTG

7441 GCTGCAAGTG GACTTCCAGA AGACAATGAA AGTCACAGGA GTAACTACTC AGGGAGTAAA

7501 ATCTCTGCTT ACCAGCATGT ATGTGAAGGA GTTCCTCATC TCCAGCAGrC AAGATGGCCA

7561 TCAGTGGACT CTCTTTTTTC AGAATGGCAA AGTAAAGGTT TTTCAGGGAA ATCAAGACTC

7621 CTTCACACCT GTGGTGAACT CTCTAGACCC ACCGTTACTG ACTCGCTACC TTCGAATTCA

7681 CCCCCAGAGT TGGGTGCACC AGATTGCCCT GAGGATGGAG GTTCTGGGCT GCGAGGCACA

7741 GGACCTCTAC GACAAAACTC ACACATGCCC ACCGTGCCGA GCTCCAGAAC TCCTGGGCGG

7801 ACCGTCAGTC TTCCTCTTCC CCCCAAAACC CAAGGACACC CTCATGATCT CCCGGACCCC

7861 TGAGGTCACA TGCGTGGTGG TGGACGTGAG CCACGAAGAC CCTGAGGTCA AGTTCAACTG

7921 GTACGTGGAC GGCGTGGAGG TGCATAATGC CAACACAAAG CCGCGGGAGG AGCAGTACAA

7981 CAGCACGMAC CGTGTGGTCA GCGTCCTCAC CGTTTTGCAC CAGGACTGGC TGANEGGCAA

8041 GGAGTACAAG TGCAAGGTCT CCAACAAAGC CCTCCCAGCC CCCATCGAGA AAACCATCTC

8101 CAAAGCCAAA GGGCAGCCCC GAGAACCACA GGTGTACACC CTGCCCCCAT CCCGGGATGA

8161 GCTGACCAAG AACCAGGTCA GCCTGACCTG CCTGGTCAAA GGCTTCTATC CAGCGACAT

8221 CGCCGTGGAG TGGGAGAGGA ATGGGCAGCC GGAGAACAAC TACAAGACCA CGCCTCCCGT

8281 GTTGGACTCC GACGGCTCCT TCTTCCTCTA CAGCAAGCTC ACCGTGGACA AGAGCAGGTG

8341 GCAGCAGGGG AACGTCTTCT CATGCTCCGT GATGGATGAG GCTCTGCACA ACCACTACAC

8401 GCAGAAGAGC CTCTCCCTGT CTCCGGGTAA A
(ii) Fc (same sequence as A (ii) (SEQ ID NO: 3)]
```

TABLE 11

Polypeptide Sequences

A. B-DoMain Deleted FVIII-FC Monomer Hybrid (BDD FVIIIFc monomer dimer): created by coexpressing BDD FVIIIFc and Fc chains. Construct = HC-LC-Fc fusion. An Fc expression cassette is cotransfected with BDDFVIII-Fc to generate the BDD FVIIIFc monomer-. For the BUD FVIIIFc chain, the Fc sequence is shown in bold; Hc sequence is shown in double underline; remaining B domain sequence is shown in italics. Signal peptides are underlined.
i) B domain deleted FVIII-Fc chain (19 amino acid signal sequence underlined) (SEQ ID NO: 2)

MQIELSTCFFLCLLRFCFSATRRYYLGAVELSWDYMQSDLGELPVDARFP

PRVPKSFPFNTSVVYKKTLFVEFTDHLFNIAKPRPPWMGLLGPTIQAEVY

DTVVITLKNMASHPVSLHAVGVSYWKASEGAEYDDQTSQREKEDDDKVFP

GGSHTYVWQVLKENGPMASDPLCLTYSYLSHVDLVKDLNSGLIGALLVCR

EGSLAKEKTQTLHKFILLFAVFDEGKSWHSETKNSLMQDRDAASARAWPK

MHTVNGYVNRSLPGLIGCHRKSVYWHVIGMGTTPEVHSIFLEGHTFLVRN

HRQASLEISPITFLTAQTLLMDLGQFLLFCHISSHQHDGMEAYVKVDSCP

EEPQLRMKNNEEAEDYDDDLTDSEMDVVRFDDDNSPSFIQIRSVAKKHPK

TWVHYIAAEEEDWDYAPLVLAPDDRSYKSQYLNNGPQRIGRKYKKVRFMA

YTDETFKTREAIQHESGILGPLLYGEVGDTLLIIFKNQASRPYNIYPHGI

TDVRPLYSRRLPKGVKHLKDFPILPGEIFKYKWTVTVEDGPTKSDPRCLT

RYYSSFVNMERDLASGLIGPLLICYKESVDQRGNQUMSDKRNVILESVFD

ENRSWYLTENIQRFLPNPAGVQLEDPEFQASNIMHSINGYVFDSLQLSVC

LHEVAYWYILSIGAQTDFLSVFFSGYTFKHKMVYEDTLTLFPFSGETVFM

SMENPGLWILGCHNSDFRNRGMTALLKVSSCDKNTGDYYEDSYEDISAYL

LSKNNAIEPR*SFSQNPPVLKRHQR*EITRTTLQSDQEEIDYDDTISVEMKK

EDFDIYDEDENQSPRSFQKKTRHYFIAAVERLWDYGMSSSPHVLRNRAQS

GSVPQFKKVVFQEFTDGSFTQPLYRGELNEHLGLLGPYIRAEVEDNIMVT

TABLE 11-continued

Polypeptide Sequences

FRNQASRPYSFYSSLISYEEDQRQGAEPRKNFVKPNETKTYFWKVQHHMA

PTKDEFDCKAWAYFSDVDLEKDVHSGLIGPLLVCHTNTLNPAHGRQVTVQ

EFALFFTIFDETKSWYFTENMERNCRAPCNIQMEDPTFKENYRFHAINGY

IMDTLPGLVMAQDQRIRWYLLSMGSNENIHSIHFSGHVFTVRKKEEYKMA

LYNLYPGVFETVEMLPSKAGIWRVECLIGEHLHAGMSTLFLVYSNKCQTP

LGMASGHIRDFQITASGQYGQWAPKLARLHYSGSINAWSTKEPFSWIKVD

LLAPMIIHGIKTQGARQKFSSLYISQFIIMYSLDGKKWQTYRGNSTGTLM

VFFGNVDSSGIKHNIFNPPIIARYIRLHPTHYSIRSTLRMELMGCDLNSC

SMPLGMESKAISDAQITASSYFTNMFATWSPSKARLHLQGRSNAWRPQVN

NPKEWLQVDFQKTMKVTGVTTQGVKSLLTSMYVKEFLISSSQDGHQWTLF

FQNGKVKVFQGNQDSFTPVVNSLDPPLLTRYLRIHPQSWVHQIALRMEVL

GCEAQDLYDKTHTCPPCPAPELLGGPSVFLFPPKPKDTLMISRTPEVTCV

VVDVSHEDPEVKFNWYVDGVEVHNAKTKPREEQYNSTYRVVSVLYVLHQD

WLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTV

DKSRWQQGNVFSCSVMHEALHNHYTQKSLSLSPGK

| ii) Fc chain (20 amino acid heterologous signal peptide from mouse Igκ chain underlined) (SEQ ID NO: 4) |
|---|

<u>METDTLLLWVLLLWVPGSTGD</u>KTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLSD

SGSFFLYSKLTVDKSRWQQGNVFSCSVMHEALHNHYTQKSLSLSPGK

| B. Full length FVIIIFc monomer hybrid (Full length FVIIIFc monomer dimer): created by coexpressing FVIIIFc and Fc chains. Construct = HC-B-LC-Fc fusion. An Fc expression cassette is cotransfected with full length FVIII-Fc to generate the full length FVIIIFc monomer. For the FVIIIFc chain, the Fc sequence is shown in bold; HC sequence is shown in double underline; B domain sequence is shown in italics. Signal peptides are underlined. |
|---|
| i) Full length FVIIIFc chain (FVIII signal peptide underlined (SEQ ID NO: 6) |

<u>MQIELSTCFFLCLLRFCFS</u>

<u>ATRRYYLGAVELSWDYMQSDLGELPVDARFPPRVPKSFPFNTSVVYKKTL</u>

<u>FVEFTDHLFNIAKPRPPWMGLLGPTIQAEVYDTVVITLKNMASHPVSLHA</u>

<u>VGVSYWKASEGAEYDDQTSQREKEDDKVFPGGSHTYVWQVLKENGPMASD</u>

<u>PLCLTYSYLSHVDLVKDLNSGLIGALLVCREGSLAKEKTQTLHKFILLFA</u>

<u>VFDEGKSWHSETKNSLMQDRDAASARAWPKMHTVNGYVNRSLPGLIGCHR</u>

<u>KSVYWHVIGMGTTPEVHSIFLEGHTFLVRNHRQASLEISPITFLTAQTLL</u>

<u>MDLGQFLLFCHISSHQHDGMEAYVKVDSCPEEPQLRMKNNEEAEDYDDDL</u>

<u>TDSEMDVVRFDDDNSPSFIQIRSVAKKHPKTWVHYIAAEEEDWDYAPLVL</u>

<u>APDDRSYKSQYLNNGPQRIGRKYKKVRFMAYTDETFKTREAIQHESGILG</u>

PLLYGEVGDTLLIIFKNQASRPYNIYPHGITDVRPLYSRRLPKGVKHLKD

FPILPGEIFKYKWTVTVEDGPTKSDPRCLTRYYSSFVNMERDLASGLIGP

LLICYKESVDQRGNQIMSDKRNVILFSVFDENRSWYLTENIQRFLPNPAG

VQLEDPEFQASNIMHSINGYVFDSLQLSVCLHEVAYWYILSIGAQTDFLS

VFFSGYTFKHKMVYEDTLTLFPFSGETVFMSMENPGLWILGCHNSDFRNR

<u>GMTALLKVSSCDKNTGDYYEDSYEDISAYLLSKNNAIEPR</u>*SFSQNSRHPS*

*TRQKQFNATTIPENDIEKTDPWFAHRTPMPKIQNVSSSDLLMLLRQSPTP*

*HGLSLSDLQEAKYETFSDDPSPGAIDSNNSLSEMTHFRPQLHHSGDMVFT*

*PESGLQLRLNEKLGTTAATELKKLDFKVSSTSNNLISTIPSDNLAAGTDN*

*TSSLGPPSMPVHYDSQLDTTLFGKKSSPLTESGGPLSLSEENNDSKLLES*

*GLMNSQESSWGKNVSSTESGRLFKGKRAHGPALLTKDNALFKVSISLLKT*

*NKTSNNSATNRKTHIDGPSLLIENSPSVWQNILESDTEFKKVTPLIHDRM*

*LMDKNATALRLNHMSNKTTSSKNMEMVQQKKEGPIPPDAQNPDMSFFKML*

*FLPESARWIQRTHGKNSLNSGQGPSPKQLVSLGPEKSVEGQNFLSEKNKV*

*VVGKGEFTKDVGLKEMVFPSSRNLFLTNLDNLHENNTHNQEKKIQEEIEK*

*KETLIQENVVLPQIHTVTGTKNFMKNLFLLSTRQNVEGSYDGAYAPVLQD*

*FRSLNDSTNRTKKHTAHFSKKGEEENLEGLGNQTKQIVEKYACTTRISPN*

*TSQQNFVTQRSKRALKQFRLPLEETELEKRIIVDDTSTQWSKNMKHLTPS*

*TLTQIDYNEKEKGAITQSPLSDCLTRSHSIPQANRSPLPIAKVSSFPSIR*

*PIYLTRVLFQDNSSHLPAASYRKKDSGVQESSHFLQGAKKNNLSLAILTL*

*EMTGDQREVGSLGTSATNSVTYKKVENTVLPKPDLPKTSGKVELLPKVHI*

*YQKDLFPTETSNGSPGHLDLVEGSLLQGTEGAIKWNEANRPGKVPFLRVA*

*TESSAKTPSKLLDPLAWDNHYGTQIPKEEWKSQEKSPEKTAFKKKDTILS*

*LNACESNHAIAAINEGQNKPEIEVTWAKQGRTERLCSQNPPVLKRHQREI*

*TRTTLQSDQEEIDYDDTISVEMKKEDFDIYDEDENQPRSFQKKTRHYFI*

*AAVERLWDYGMSSSPHVLRNRAQSGSVPQFKKVVFQEFTDGSFTQPLYRG*

*ELNEHLGLLGPYIRAEVEDNIMVT*FRNQASRPYSFYSSLISYEEDQRQGA

EPRKNFVKPNETKTYFWKVQHHMAPTKDEFDCKAWAYFSDVDLEKDVHSG

LIGPLLVCHTNTLNPAHGRQVTVQEFALFFTIFDETKSWYFTENMERNCR

APCNIQMEDPTFKENYRFHAINGYIMDTLPGLVMAQDQRIRWYLLSMGSN

ENIHSIHFSGHVFTVRKKEEYKMALYNLYPGVFETVEMLPSKAGIWRVEC

LIGEHLHAGMSTLFLVYSNKCQTPLGMASGHIRDFQITASGQYGQWAPKL

ARLHYSGSINAWSTKEPFSWIKVDLLAPMIIHGIKTQGARQKFSSLYISQ

FIIMYSLDGKKWQTYRGNSTGTLMVFFGNVDSSGIKHNIFNPPIIARYIR

LHPTHYSIRSTLRMELMGCDLNSCSMPLGMESKAISDAQITASSYFTNMF

ATWSPSKARLHLQGRSNAWRPQVNNPKEWLQVDFQKTMKVTGVTTQGVKS

LLTSMYVKEFLISSSQDGHQWTLFFQNGKVKVFQGNQDSFTPVVNSLDPP

LLTRYLRIHPQSWVHQIALRMEVLGCEAQDLYDKTHTCPPCPAPELLGGP

SVFLFPPKPKDTLMISRTPEVTCVVVDVSHEDPEVKFNWYVDGVEVHNAK

TABLE 11-continued

Polypeptide Sequences

TKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQ

KSLSLSPGK ii) Fc chain (20 amino acid heterologous signal peptide from mouse Igκ chain underlined) (SEQ ID NO: 4)

METDTLLLWVLLLWVPGSTGDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are incorporated by reference herein in their entirety.

What is claimed is:

1. A pharmaceutical composition comprising:
   a) about 50 IU/ml to about 2500 IU/ml of a long-acting FVIII polypeptide;
   b) about 10 mg/ml to about 25 mg/ml of a stabilizing agents selected from the group consisting of sucrose, trehalose, raffinose, arginine, and any mixture thereof;
   c) about 8.8 mg/ml to about 14.6 mg/ml sodium chloride (NaCl);
   d) about 0.75 mg/ml to about 2.25 mg/ml L-histidine;
   e) about 0.75 mg/ml to about 1.5 mg/ml calcium chloride dihydrate; and
   f) about 0.08 mg/ml to about 0.25 mg/ml polysorbate 20 or polysorbate 80.

2. The pharmaceutical composition of claim 1, wherein mannitol, glycine, alanine, or hydroxyethyl starch is not included.

3. The pharmaceutical composition of claim 1, wherein NaCl is the only bulking agent.

4. The pharmaceutical composition of claim 1, comprising about 13 mg/ml to about 20 mg/ml sucrose.

5. The pharmaceutical composition of claim 1, comprising about 13.3 mg/ml to about 20 mg/ml sucrose.

6. The pharmaceutical composition of claim 1, comprising about 10 mg/ml to about 13 mg/ml NaCl.

7. The pharmaceutical composition of claim 1, comprising about 12.0 mg/ml NaCl.

8. The pharmaceutical composition of claim 1, comprising about 1.03 mg/ml L-histidine.

9. The pharmaceutical composition of claim 1, comprising about 1.55 mg/ml L-histidine.

10. The pharmaceutical composition of claim 1, comprising about 0.8 mg/ml calcium chloride dihydrate.

11. The pharmaceutical composition of claim 1, comprising about 1.18 mg/ml calcium chloride dihydrate.

12. The pharmaceutical composition of claim 1, comprising about 0.13 mg/ml polysorbate 20 or polysorbate 80.

13. The pharmaceutical composition of claim 1, comprising about 0.20 mg/ml polysorbate 20 or polysorbate 80.

14. The pharmaceutical composition of claim 1, wherein the FVIII polypeptide comprises a first subunit comprising an amino acid sequence at least 90% or 95% identical to amino acids 20 to 1684 of SEQ ID NO:2 or 20 to 2578 of SEQ ID NO:6, and a second subunit comprising an amino acid sequence at least 90% to 95% identical to amino acids 21 to 247 of SEQ ID NO:4.

15. The pharmaceutical composition of claim 1, wherein the FVIII polypeptide is present at a concentration of about 50 IU/ml to about 1500 IU/ml.

16. The pharmaceutical composition of claim 1, wherein the FVIII polypeptide is present at a concentration of about 100 IU/ml to about 2500 IU/ml.

17. The pharmaceutical composition of claim 1, comprising:
   (a) about 50 IU/ml to about 1500 IU/ml of the long-acting FVIII polypeptide;
   (b) about 10 mg/ml to about 25 mg/ml of sucrose;
   (c) about 8.8 mg/ml to about 14.6 mg/ml NaCl;
   (d) about 0.75 mg/ml to about 2.25 mg/ml L-histidine;
   (e) about 0.75 mg/ml to about 1.5 mg/ml calcium chloride dihydrate; and
   (f) about 0.08 mg/ml to about 0.25 mg/ml of polysorbate 20 or polysorbate 80.

18. The pharmaceutical composition of claim 1, comprising:
   (a) about 100 IU/ml to about 2500 IU/ml of the long-acting FVIII polypeptide;
   (b) about 10 mg/ml to about 25 mg/ml of sucrose;
   (c) about 14.6 mg/ml to about 20.5 mg/ml NaCl;
   (d) about 0.75 mg/ml to about 2.25 mg/ml L-histidine;
   (e) about 0.75 mg/ml to about 1.5 mg/ml calcium chloride dihydrate; and
   (f) about 0.08 mg/ml to about 0.25 mg/ml of polysorbate 20 or polysorbate 80.

19. A pharmaceutical kit comprising:
   (a) a first container comprising a lyophilized powder, where the powder comprises
      (i) about 250 IU, about 500 IU, about 750 IU, about 1000 IU, about 1500 IU, about 2000 IU, or about 3000 IU of a long-acting FVIII polypeptide,
      (ii) about 40 mg of a stabilizing agents selected from the group consisting of sucrose, trehalose, raffinose, arginine, and any mixture thereof;
      (iii) about 36 mg of sodium chloride (NaCl);
      (iv) about 3.1 mg of L-histidine;
      (v) about 2.40 mg calcium chloride dihydrate; and
      (vi) about 0.40 mg polysorbate 20 or polysorbate 80; and
   (b) a second container comprising sterilized water for injections at a volume sufficient to produce, when combined with the lyophilized powder of the first container, a solution comprising:
      (i) about 83 IU/ml, about 167 IU/ml, about 250 IU/ml, about 333 IU/ml, about 500 IU/ml, about 667 IU/ml, or about 1000 IU/ml of the FVIII polypeptide, respectively;
      (ii) about 13.3 mg/ml of the stabilizing agent;
      (iii) about 12.0 mg/ml of NaCl;
      (iv) about 1.03 mg/ml of L-histidine;
      (v) about 0.80 mg/ml of calcium chloride dihydrate; and
      (vi) about 0.13 mg/ml of polysorbate 20 or polysorbate 80.

20. The pharmaceutical kit of claim 19, wherein mannitol, glycine, alanine, or hydroxyethyl starch is not included.

21. The pharmaceutical kit of claim 19, wherein NaCl is the only bulking agent.

22. The pharmaceutical kit of claim 19, wherein the stabilizing agent comprises sucrose.

23. The pharmaceutical composition of claim 1, wherein the stabilizing agent comprises sucrose.

24. The pharmaceutical kit of claim 19, wherein the first container is a glass vial comprising a rubber stopper.

25. The pharmaceutical kit of claim 19, wherein the second container is a syringe body.

26. The pharmaceutical kit of claim 24, and wherein the syringe body is associated with a plunger.

27. The pharmaceutical composition of claim 1, comprising:
   (a) about 83 IU/ml, about 167 IU/ml, about 250 IU/ml, about 333 IU/ml, about 500 IU/ml, about 667 IU/ml, or about 1000 IU/ml of the long-acting FVIII polypeptide;
   (b) about 10 mg/ml to about 25 mg/ml of sucrose;
   (c) about 8.8 mg/ml to about 14.6 mg/ml NaCl;
   (d) about 0.75 mg/ml to about 2.25 mg/ml L-histidine;
   (e) about 0.75 mg/ml to about 1.5 mg/ml calcium chloride dihydrate; and
   (f) about 0.08 mg/ml to about 0.25 mg/ml of polysorbate 20 or polysorbate 80.

28. The pharmaceutical composition of claim 1, comprising:
   (a) about 83 IU/ml, about 167 IU/ml, about 250 IU/ml, about 333 IU/ml, about 500 IU/ml, about 667 IU/ml, or about 1000 IU/ml of the long-acting FVIII polypeptide;
   (b) about 13.3 mg/ml of sucrose;
   (c) about 12.0 mg/ml NaCl;
   (d) about 1.03 mg/ml L-histidine;
   (e) about 0.8 mg/ml calcium chloride dihydrate; and
   (f) about 0.13 mg/ml of polysorbate 20 or polysorbate 80.

29. The pharmaceutical composition of claim 1, comprising:
   (a) about 83 IU/ml of the long-acting FVIII polypeptide;
   (b) about 13.3 mg/ml of sucrose;
   (c) about 12.0 mg/ml NaCl;
   (d) about 1.03 mg/ml L-histidine;
   (e) about 0.8 mg/ml calcium chloride dihydrate; and
   (f) about 0.13 mg/ml of polysorbate 20 or polysorbate 80.

30. The pharmaceutical composition of claim 1, comprising:
   (a) about 167 IU/ml of the long-acting FVIII polypeptide;
   (b) about 13.3 mg/ml of sucrose;
   (c) about 12.0 mg/ml NaCl;
   (d) about 1.03 mg/ml L-histidine;
   (e) about 0.8 mg/ml calcium chloride dihydrate; and
   (f) about 0.13 mg/ml of polysorbate 20 or polysorbate 80.

31. The pharmaceutical composition of claim 1, comprising:
   (a) about 250 IU/ml of the long-acting FVIII polypeptide;
   (b) about 13.3 mg/ml of sucrose;
   (c) about 12.0 mg/ml NaCl;
   (d) about 1.03 mg/ml L-histidine;
   (e) about 0.8 mg/ml calcium chloride dihydrate; and
   (f) about 0.13 mg/ml of polysorbate 20 or polysorbate 80.

32. The pharmaceutical composition of claim 1, comprising:
   (a) about 333 IU/ml of the long-acting FVIII polypeptide;
   (b) about 13.3 mg/ml of sucrose;
   (c) about 12.0 mg/ml NaCl;
   (d) about 1.03 mg/ml L-histidine;
   (e) about 0.8 mg/ml calcium chloride dihydrate; and
   (f) about 0.13 mg/ml of polysorbate 20 or polysorbate 80.

33. The pharmaceutical composition of claim 1, comprising:
   (a) about 500 IU/ml of the long-acting FVIII polypeptide;
   (b) about 13.3 mg/ml of sucrose;
   (c) about 12.0 mg/ml NaCl;
   (d) about 1.03 mg/ml L-histidine;
   (e) about 0.8 mg/ml calcium chloride dihydrate; and
   (f) about 0.13 mg/ml of polysorbate 20 or polysorbate 80.

34. The pharmaceutical composition of claim 1, comprising:
   (a) about 667 IU/ml of the long-acting FVIII polypeptide;
   (b) about 13.3 mg/ml of sucrose;
   (c) about 12.0 mg/ml NaCl;
   (d) about 1.03 mg/ml L-histidine;
   (e) about 0.8 mg/ml calcium chloride dihydrate; and
   (f) about 0.13 mg/ml of polysorbate 20 or polysorbate 80.

35. The pharmaceutical composition of claim 1, comprising:
   (a) about 1000 IU/ml of the long-acting FVIII polypeptide;
   (b) about 13.3 mg/ml of sucrose;
   (c) about 12.0 mg/ml NaCl;
   (d) about 1.03 mg/ml L-histidine;
   (e) about 0.8 mg/ml calcium chloride dihydrate; and
   (f) about 0.13 mg/ml of polysorbate 20 or polysorbate 80.

* * * * *

SEQUENCE LISTING

```
<160> NUMBER OF SEQ ID NOS: 18

<210> SEQ ID NO 1
<211> LENGTH: 5052
<212> TYPE: DNA
<213> ORGANISM: Artificial Sequence
<220> FEATURE:
<223> OTHER INFORMATION: B-Domain Deleted FVIIIFc

<400> SEQUENCE: 1
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggataggggat     720 gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca aagtagacag ctgtccagag gaaccccaac tacgaatgaa aaataatgaa    1080
gaagcggaag actatgatga tgatcttact gattctgaaa tggatgtggt caggtttgat    1140
```

```
gatgacaact ctccttcctt tatccaaatt cgctcagttg ccaagaagca tcctaaaact    1200
tgggtacatt acattgctgc tgaagaggag gactgggact atgctcccct agtcctcgcc    1260
cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag agaaactgt cttcatgtcg    2100 atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaaa acccaccagt cttgaaacgc catcaacggg aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat ggacccctt     2940 ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccactt taaagagaat    3120 tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctct    3420
gtgtacagca ataagtgtca gactcccctg ggaatggctc tggacacat tagagatttt    3480 cagattacag cttcaggaca atatggacag tgggccccaa agctggccag acttcattat    3540
```

-continued

```
tccggatcaa tcaatgcctg agcaccaag gagcccttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata tttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga aagtcacagg agtaactact cagggagtaa aatctctgct taccagcatg    4140
tatgtgaagg agttcctcat ctccagcagt caagatggcc atcagtggac tctctttttt    4200
cagaatggca agtaaaggt tttcaggga atcaagact ccttcacacc tgtggtgaac    4260
tctctagacc caccgttact gactcgctac cttcgaattc accccagag ttgggtgcac    4320 cagattgccc tgaggatgga ggttctgggc tgcgaggcac aggacctcta cgacaaaact    4380
cacacatgcc caccgtgccc agctccagaa ctcctgggcg gaccgtcagt cttcctcttc    4440 ccccaaaac ccaaggacac cctcatgatc tcccggaccc ctgaggtcac atgcgtggtg    4500
gtggacgtga gccacgaaga ccctgaggtc aagttcaact ggtacgtgga cggcgtggag    4560
gtgcataatg ccaagacaaa gccgcgggag gagcagtaca acagcacgta ccgtgtggtc    4620
agcgtcctca ccgtcctgca ccaggactgg ctgaatggca aggagtacaa gtgcaaggtc    4680
tccaacaaag ccctcccagc ccccatcgag aaaaccatct ccaaagccaa agggcagccc    4740
cgagaaccac aggtgtacac cctgcccccca tcccgggatg agctgaccaa gaaccaggtc    4800
agcctgacct gcctggtcaa aggcttctat cccagcgaca tcgccgtgga gtgggagagc    4860
aatgggcagc cggagaacaa ctacaagacc acgcctcccg tgttggactc cgacggctcc    4920
ttcttcctct acagcaagct caccgtggac aagagcaggt ggcagcaggg gaacgtcttc    4980
tcatgctccg tgatgcatga ggctctgcac aaccactaca cgcagaagag cctctccctg    5040
tctccgggta aa    5052
```

<210> SEQ ID NO 2
<211> LENGTH: 1684
<212> TYPE: PRT
<213> ORGANISM: Artificial Sequence
<220> FEATURE:
<223> OTHER INFORMATION: B-Domain Deleted FVIIIFc

<400> SEQUENCE: 2

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95
```

```
Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
            210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
            290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510
```

```
Gly Val Lys His Leu Lys Asp Phe Pro Ile Leu Pro Gly Glu Ile Phe
515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925
```

```
Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
            965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320
```

Met Phe Ala Thr Trp Ser Pro Ser Lys Ala Arg Leu His Leu Gln
1325                1330                1335

Gly Arg Ser Asn Ala Trp Arg Pro Gln Val Asn Asn Pro Lys Glu
1340                1345                1350

Trp Leu Gln Val Asp Phe Gln Lys Thr Met Lys Val Thr Gly Val
1355                1360                1365

Thr Thr Gln Gly Val Lys Ser Leu Leu Thr Ser Met Tyr Val Lys
1370                1375                1380

Glu Phe Leu Ile Ser Ser Ser Gln Asp Gly His Gln Trp Thr Leu
1385                1390                1395

Phe Phe Gln Asn Gly Lys Val Lys Val Phe Gln Gly Asn Gln Asp
1400                1405                1410

Ser Phe Thr Pro Val Val Asn Ser Leu Asp Pro Pro Leu Leu Thr
1415                1420                1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr Asp
1445                1450                1455

Lys Thr His Thr Cys Pro Pro Cys Pro Ala Pro Glu Leu Leu Gly
1460                1465                1470

Gly Pro Ser Val Phe Leu Phe Pro Pro Lys Pro Lys Asp Thr Leu
1475                1480                1485

Met Ile Ser Arg Thr Pro Glu Val Thr Cys Val Val Val Asp Val
1490                1495                1500

Ser His Glu Asp Pro Glu Val Lys Phe Asn Trp Tyr Val Asp Gly
1505                1510                1515

Val Glu Val His Asn Ala Lys Thr Lys Pro Arg Glu Glu Gln Tyr
1520                1525                1530

Asn Ser Thr Tyr Arg Val Val Ser Val Leu Thr Val Leu His Gln
1535                1540                1545

Asp Trp Leu Asn Gly Lys Glu Tyr Lys Cys Lys Val Ser Asn Lys
1550                1555                1560

Ala Leu Pro Ala Pro Ile Glu Lys Thr Ile Ser Lys Ala Lys Gly
1565                1570                1575

Gln Pro Arg Glu Pro Gln Val Tyr Thr Leu Pro Pro Ser Arg Asp
1580                1585                1590

Glu Leu Thr Lys Asn Gln Val Ser Leu Thr Cys Leu Val Lys Gly
1595                1600                1605

Phe Tyr Pro Ser Asp Ile Ala Val Glu Trp Glu Ser Asn Gly Gln
1610                1615                1620

Pro Glu Asn Asn Tyr Lys Thr Thr Pro Pro Val Leu Asp Ser Asp
1625                1630                1635

Gly Ser Phe Phe Leu Tyr Ser Lys Leu Thr Val Asp Lys Ser Arg
1640                1645                1650

Trp Gln Gln Gly Asn Val Phe Ser Cys Ser Val Met His Glu Ala
1655                1660                1665

Leu His Asn His Tyr Thr Gln Lys Ser Leu Ser Leu Ser Pro Gly
1670                1675                1680

Lys

<210> SEQ ID NO 3
<211> LENGTH: 741
<212> TYPE: DNA
<213> ORGANISM: Artificial Sequence
<220> FEATURE:
<223> OTHER INFORMATION: Fc Portion

<400> SEQUENCE: 3

```
atggagacag acacactcct gctatgggta ctgctgctct gggttccagg ttccactggt    60
gacaaaactc acacatgccc accgtgccca gcacctgaac tcctgggagg accgtcagtc   120
ttcctcttcc ccccaaaacc caaggacacc ctcatgatct cccggacccc tgaggtcaca   180
tgcgtggtgg tggacgtgag ccacgaagac cctgaggtca agttcaactg gtacgtggac   240
ggcgtggagg tgcataatgc caagacaaag ccgcgggagg agcagtacaa cagcacgtac   300
cgtgtggtca gcgtcctcac cgtcctgcac caggactggc tgaatggcaa ggagtacaag   360
tgcaaggtct ccaacaaagc cctcccagcc cccatcgaga aaaccatctc caaagccaaa   420
gggcagcccc gagaaccaca ggtgtacacc ctgcccccat cccgcgatga gctgaccaag   480
aaccaggtca gcctgacctg cctggtcaaa ggcttctatc ccagcgacat cgccgtggag   540
tgggagagca atgggcagcc ggagaacaac tacaagacca cgcctcccgt gttggactcc   600
gacggctcct tcttcctcta cagcaagctc accgtggaca agagcaggtg gcagcagggg   660
aacgtcttct catgctccgt gatgcatgag gctctgcaca accactacac gcagaagagc   720
ctctccctgt ctccgggtaa a                                             741
```

<210> SEQ ID NO 4
<211> LENGTH: 247
<212> TYPE: PRT
<213> ORGANISM: Artificial Sequence
<220> FEATURE:
<223> OTHER INFORMATION: Fc Portion

<400> SEQUENCE: 4

```
Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205
```

```
Lys Leu Thr Val Asp Lys Ser Arg Trp Gln Gln Gly Asn Val Phe Ser
    210                 215                 220
Cys Ser Val Met His Glu Ala Leu His Asn His Tyr Thr Gln Lys Ser
225                 230                 235                 240
Leu Ser Leu Ser Pro Gly Lys
            245

<210> SEQ ID NO 5
<211> LENGTH: 7734
<212> TYPE: DNA
<213> ORGANISM: Artificial Sequence
<220> FEATURE:
<223> OTHER INFORMATION: Full Length FVIIIFc

<400> SEQUENCE: 5
```

| | | | | |
|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | caaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgg | tcattacact | taagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaagacttt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaaagaact | ccttgatgca | ggataggga t | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |
| accactcctg | aagtgcactc | aatattcctc | gaaggtcaca | catttcttgt | gaggaaccat | 900 |
| cgccaggcgt | ccttggaaat | ctcgccaata | actttcctta | ctgctcaaac | actcttgatg | 960 |
| gaccttggac | agtttctact | gttttgtcat | atctcttccc | accaacatga | tggcatggaa | 1020 |
| gcttatgtca | aagtagacag | ctgtccagag | gaacccaac | tacgaatgaa | aaataatgaa | 1080 |
| gaagcggaag | actatgatga | tgatcttact | gattctgaaa | tggatgtggt | caggtttgat | 1140 |
| gatgacaact | ctccttcctt | tatccaaatt | cgctcagttg | ccaagaagca | tcctaaaact | 1200 |
| tgggtacatt | acattgctgc | tgaagaggag | gactgggact | atgctccctt | agtcctcgcc | 1260 |
| cccgatgaca | gaagttataa | aagtcaatat | ttgaacaatg | gccctcagcg | gattggtagg | 1320 |
| aagtacaaaa | aagtccgatt | tatggcatac | acagatgaaa | cctttaagac | tcgtgaagct | 1380 |
| attcagcatg | aatcaggaat | cttgggacct | ttactttatg | gggaagttgg | agacacactg | 1440 |
| ttgattatat | ttaagaatca | agcaagcaga | ccatataaca | tctaccctca | cggaatcact | 1500 |
| gatgtccgtc | ctttgtattc | aaggagatta | ccaaaaggtg | taaaacattt | gaaggatttt | 1560 |
| ccaattctgc | caggagaaat | attcaaatat | aaatggacag | tgactgtaga | agatgggcca | 1620 |
| actaaatcag | atcctcggtg | cctgacccgc | tattactcta | gtttcgttaa | tatggagaga | 1680 |
| gatctagctt | caggactcat | tggccctctc | ctcatctgct | acaaagaatc | tgtagatcaa | 1740 |
| agaggaaacc | agataatgtc | agacaagagg | aatgtcatcc | tgtttctgt | atttgatgag | 1800 |

```
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag gagaaactgt cttcatgtcg    2100
atggaaaacc caggtctatg gattctgggg tgccacaact cagactttcg aacagaggc     2160 atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca ccctagcact aggcaaaagc aatttaatgc caccacaatt    2340
ccagaaaatg acatagagaa gactgaccct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga cttttctga tgatccatca     2520 cctggagcaa tagacagtaa taacagcctg tctgaaatga cacacttcag gccacagctc    2580
catcacagtg gggacatggt atttacccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag gaccccaag tatgccagtt cattatgata gtcaattaga taccactcta     2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaaattc aggaagaaat agaaagaag    3660 gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca aaggatatc tcctaataca    3960 agccagcaga attttgtcac gcaacgtagt aagagagctt tgaaacaatt cagactccca    4020
ctagaagaaa cagaacttga aaaaggata attgtggatg acacctcaac ccagtggtcc    4080
aaaaacatga acatttgac cccgagcacc ctcacacaga tagactacaa tgagaaggag    4140
aaaggggcca ttactcagtc tccccttatca gattgcctta cgaggagtca tagcatccct    4200
```

| | | | | | |
|---|---|---|---|---|---|
| caagcaaata | gatctccatt | acccattgca | aaggtatcat | catttccatc | tattagacct | 4260 |
| atatatctga | ccagggtcct | attccaagac | aactcttctc | atcttccagc | agcatcttat | 4320 |
| agaaagaaag | attctggggt | ccaagaaagc | agtcatttct | tacaaggagc | caaaaaaat | 4380 |
| aacctttctt | tagccattct | aaccttggag | atgactggtg | atcaaagaga | ggttggctcc | 4440 |
| ctggggacaa | gtgccacaaa | ttcagtcaca | tacaagaaag | ttgagaacac | tgttctcccg | 4500 |
| aaaccagact | tgcccaaaac | atctggcaaa | gttgaattgc | ttccaaaagt | tcacatttat | 4560 |
| cagaaggacc | tattccctac | ggaaactagc | aatgggtctc | ctggccatct | ggatctcgtg | 4620 |
| gaagggagcc | ttcttcaggg | aacagaggga | gcgattaagt | ggaatgaagc | aaacagacct | 4680 |
| ggaaaagttc | cctttctgag | agtagcaaca | gaaagctctg | caaagactcc | ctccaagcta | 4740 |
| ttggatcctc | ttgcttggga | taaccactat | ggtactcaga | taccaaaaga | agagtggaaa | 4800 |
| tcccaagaga | agtcaccaga | aaaaacagct | tttaagaaaa | aggataccat | tttgtccctg | 4860 |
| aacgcttgtg | aaagcaatca | tgcaatagca | gcaataaatg | agggacaaaa | taagcccgaa | 4920 |
| atagaagtca | cctgggcaaa | gcaaggtagg | actgaaaggc | tgtgctctca | aaacccacca | 4980 |
| gtcttgaaac | gccatcaacg | ggaaataact | cgtactactc | ttcagtcaga | tcaagaggaa | 5040 |
| attgactatg | atgataccat | atcagttgaa | atgaagaagg | aagattttga | catttatgat | 5100 |
| gaggatgaaa | atcagagccc | ccgcagcttt | caaaagaaaa | cacgacacta | ttttattgct | 5160 |
| gcagtggaga | ggctctggga | ttatgggatg | agtagctccc | cacatgttct | aagaaacagg | 5220 |
| gctcagagtg | gcagtgtccc | tcagttcaag | aaagttgttt | tccaggaatt | tactgatggc | 5280 |
| tcctttactc | agcccttata | ccgtggagaa | ctaaatgaac | attgggact | cctggggcca | 5340 |
| tatataagag | cagaagttga | agataatatc | atggtaactt | tcagaaatca | ggcctctcgt | 5400 |
| ccctattcct | tctattctag | ccttatttct | tatgaggaag | atcagaggca | aggagcagaa | 5460 |
| cctagaaaaa | actttgtcaa | gcctaatgaa | accaaaactt | acttttggaa | agtgcaacat | 5520 |
| catatggcac | ccactaaaga | tgagtttgac | tgcaaagcct | gggcttattt | ctctgatgtt | 5580 |
| gacctggaaa | aagatgtgca | ctcaggcctg | attggacccc | ttctggtctg | ccacactaac | 5640 |
| acactgaacc | ctgctcatgg | gagacaagtg | acagtacagg | aatttgctct | gtttttcacc | 5700 |
| atctttgatg | agaccaaaag | ctggtacttc | actgaaaata | tggaaagaaa | ctgcagggct | 5760 |
| ccctgcaata | tccagatgga | agatcccact | tttaaagaga | attatcgctt | ccatgcaatc | 5820 |
| aatggctaca | taatggatac | actacctggc | ttagtaatgg | ctcaggatca | aaggattcga | 5880 |
| tggtatctgc | tcagcatggg | cagcaatgaa | aacatccatt | ctattcattt | cagtggacat | 5940 |
| gtgttcactg | tacgaaaaaa | agaggagtat | aaaatggcac | tgtacaatct | ctatccaggt | 6000 |
| gtttttgaga | cagtggaaat | gttaccatcc | aaagctggaa | tttggcgggt | ggaatgcctt | 6060 |
| attggcgagc | atctacatgc | tgggatgagc | acactttttc | tggtgtacag | caataagtgt | 6120 |
| cagactcccc | tgggaatggc | ttctggacac | attagagatt | ttcagattac | agcttcagga | 6180 |
| caatatggac | agtgggcccc | aaagctggcc | agacttcatt | attccggatc | aatcaatgcc | 6240 |
| tggagcacca | aggagcccctt | ttcttggatc | aaggtggatc | tgttggcacc | aatgattatt | 6300 |
| cacggcatca | agaccagggg | tgcccgtcag | aagttctcca | gcctctacat | ctctcagttt | 6360 |
| atcatcatgt | atagtcttga | tgggaagaag | tggcagactt | atcgaggaaa | ttccactgga | 6420 |
| accttaatgg | tcttctttgg | caatgtggat | tcatctggga | taaaacacaa | tatttttaac | 6480 |
| cctccaatta | ttgctcgata | catccgtttg | cacccaactc | attatagcat | tcgcagcact | 6540 |
| cttcgcatgg | agttgatggg | ctgtgattta | aatagttgca | gcatgccatt | gggaatggag | 6600 |

-continued

```
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900
gtttttcagg gaaatcaaga ctccttcaca cctgtggtga actctctaga cccaccgtta    6960
ctgactcgct accttcgaat tcaccccccag agttgggtgc accagattgc cctgaggatg    7020
gaggttctgg gctgcgaggc acaggacctc tacgacaaaa ctcacacatg cccaccgtgc    7080
ccagctccag aactcctggg cggaccgtca gtcttcctct tccccccaaa acccaaggac    7140
accctcatga tctcccggac ccctgaggtc acatgcgtgg tggtggacgt gagccacgaa    7200
gaccctgagg tcaagttcaa ctggtacgtg gacggcgtgg aggtgcataa tgccaagaca    7260
aagccgcggg aggagcagta caacagcacg taccgtgtgg tcagcgtcct caccgtcctg    7320
caccaggact ggctgaatgg caaggagtac aagtgcaagg tctccaacaa agccctccca    7380
gcccccatcg agaaaaccat ctccaaagcc aaagggcagc cccgagaacc acaggtgtac    7440
accctgcccc catcccggga tgagctgacc aagaaccagg tcagcctgac ctgcctggtc    7500
aaaggcttct atcccagcga catcgccgtg gagtgggaga gcaatgggca gccggagaac    7560
aactacaaga ccacgcctcc cgtgttggac tccgacggct ccttcttcct ctacagcaag    7620
ctcaccgtgg acaagagcag gtggcagcag gggaacgtct tctcatgctc cgtgatgcat    7680
gaggctctgc acaaccacta cacgcagaag agcctctccc tgtctccggg taaa          7734
```

<210> SEQ ID NO 6
<211> LENGTH: 2578
<212> TYPE: PRT
<213> ORGANISM: Artificial Sequence
<220> FEATURE:
<223> OTHER INFORMATION: Full Length FVIIIFc

<400> SEQUENCE: 6

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160
```

-continued

```
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
        195                 200                 205
Gln Thr Leu His Lys Phe Ile Leu Leu Phe Ala Val Phe Asp Glu Gly
    210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
        275                 280                 285
Phe Leu Glu Gly His Thr Phe Leu Val Arg Asn His Arg Gln Ala Ser
    290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
        355                 360                 365
Leu Thr Asp Ser Glu Met Asp Val Val Arg Phe Asp Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
```

```
Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
            805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
            885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
            965                 970                 975

Ser Ser Trp Gly Lys Asn Val Ser Ser Thr Glu Ser Gly Arg Leu Phe
            980                 985                 990
```

-continued

```
Lys Gly Lys Arg Ala His Gly Pro  Ala Leu Leu Thr Lys  Asp Asn Ala
        995              1000                 1005

Leu Phe Lys Val Ser Ile Ser  Leu Leu Lys Thr Asn  Lys Thr Ser
    1010            1015                 1020

Asn Asn Ser Ala Thr Asn Arg  Lys Thr His Ile Asp  Gly Pro Ser
    1025            1030                 1035

Leu Leu Ile Glu Asn Ser Pro  Ser Val Trp Gln Asn  Ile Leu Glu
    1040            1045                 1050

Ser Asp Thr Glu Phe Lys Lys  Val Thr Pro Leu Ile  His Asp Arg
    1055            1060                 1065

Met Leu Met Asp Lys Asn Ala  Thr Ala Leu Arg Leu  Asn His Met
    1070            1075                 1080

Ser Asn Lys Thr Thr Ser Ser  Lys Asn Met Glu Met  Val Gln Gln
    1085            1090                 1095

Lys Lys Glu Gly Pro Ile Pro  Pro Asp Ala Gln Asn  Pro Asp Met
    1100            1105                 1110

Ser Phe Phe Lys Met Leu Phe  Leu Pro Glu Ser Ala  Arg Trp Ile
    1115            1120                 1125

Gln Arg Thr His Gly Lys Asn  Ser Leu Asn Ser Gly  Gln Gly Pro
    1130            1135                 1140

Ser Pro Lys Gln Leu Val Ser  Leu Gly Pro Glu Lys  Ser Val Glu
    1145            1150                 1155

Gly Gln Asn Phe Leu Ser Glu  Lys Asn Lys Val Val  Val Gly Lys
    1160            1165                 1170

Gly Glu Phe Thr Lys Asp Val  Gly Leu Lys Glu Met  Val Phe Pro
    1175            1180                 1185

Ser Ser Arg Asn Leu Phe Leu  Thr Asn Leu Asp Asn  Leu His Glu
    1190            1195                 1200

Asn Asn Thr His Asn Gln Glu  Lys Lys Ile Gln Glu  Glu Ile Glu
    1205            1210                 1215

Lys Lys Glu Thr Leu Ile Gln  Glu Asn Val Val Leu  Pro Gln Ile
    1220            1225                 1230

His Thr Val Thr Gly Thr Lys  Asn Phe Met Lys Asn  Leu Phe Leu
    1235            1240                 1245

Leu Ser Thr Arg Gln Asn Val  Glu Gly Ser Tyr Asp  Gly Ala Tyr
    1250            1255                 1260

Ala Pro Val Leu Gln Asp Phe  Arg Ser Leu Asn Asp  Ser Thr Asn
    1265            1270                 1275

Arg Thr Lys Lys His Thr Ala  His Phe Ser Lys Lys  Gly Glu Glu
    1280            1285                 1290

Glu Asn Leu Glu Gly Leu Gly  Asn Gln Thr Lys Gln  Ile Val Glu
    1295            1300                 1305

Lys Tyr Ala Cys Thr Thr Arg  Ile Ser Pro Asn Thr  Ser Gln Gln
    1310            1315                 1320

Asn Phe Val Thr Gln Arg Ser  Lys Arg Ala Leu Lys  Gln Phe Arg
    1325            1330                 1335

Leu Pro Leu Glu Glu Thr Glu  Leu Glu Lys Arg Ile  Ile Val Asp
    1340            1345                 1350

Asp Thr Ser Thr Gln Trp Ser  Lys Asn Met Lys His  Leu Thr Pro
    1355            1360                 1365

Ser Thr Leu Thr Gln Ile Asp  Tyr Asn Glu Lys Glu  Lys Gly Ala
    1370            1375                 1380
```

-continued

```
Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770
```

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
1985                1990                1995

Pro Gly Val Phe Glu Thr Val Glu Met Leu Pro Ser Lys Ala Gly
2000                2005                2010

Ile Trp Arg Val Glu Cys Leu Ile Gly Glu His Leu His Ala Gly
2015                2020                2025

Met Ser Thr Leu Phe Leu Val Tyr Ser Asn Lys Cys Gln Thr Pro
2030                2035                2040

Leu Gly Met Ala Ser Gly His Ile Arg Asp Phe Gln Ile Thr Ala
2045                2050                2055

Ser Gly Gln Tyr Gly Gln Trp Ala Pro Lys Leu Ala Arg Leu His
2060                2065                2070

Tyr Ser Gly Ser Ile Asn Ala Trp Ser Thr Lys Glu Pro Phe Ser
2075                2080                2085

Trp Ile Lys Val Asp Leu Leu Ala Pro Met Ile Ile His Gly Ile
2090                2095                2100

Lys Thr Gln Gly Ala Arg Gln Lys Phe Ser Ser Leu Tyr Ile Ser
2105                2110                2115

Gln Phe Ile Ile Met Tyr Ser Leu Asp Gly Lys Lys Trp Gln Thr
2120                2125                2130

Tyr Arg Gly Asn Ser Thr Gly Thr Leu Met Val Phe Phe Gly Asn
2135                2140                2145

Val Asp Ser Ser Gly Ile Lys His Asn Ile Phe Asn Pro Pro Ile
2150                2155                2160

```
Ile Ala Arg Tyr Ile Arg Leu His Pro Thr His Tyr Ser Ile Arg
2165                2170                2175

Ser Thr Leu Arg Met Glu Leu Met Gly Cys Asp Leu Asn Ser Cys
2180                2185                2190

Ser Met Pro Leu Gly Met Glu Ser Lys Ala Ile Ser Asp Ala Gln
2195                2200                2205

Ile Thr Ala Ser Ser Tyr Phe Thr Asn Met Phe Ala Thr Trp Ser
2210                2215                2220

Pro Ser Lys Ala Arg Leu His Leu Gln Gly Arg Ser Asn Ala Trp
2225                2230                2235

Arg Pro Gln Val Asn Asn Pro Lys Glu Trp Leu Gln Val Asp Phe
2240                2245                2250

Gln Lys Thr Met Lys Val Thr Gly Val Thr Thr Gln Gly Val Lys
2255                2260                2265

Ser Leu Leu Thr Ser Met Tyr Val Lys Glu Phe Leu Ile Ser Ser
2270                2275                2280

Ser Gln Asp Gly His Gln Trp Thr Leu Phe Phe Gln Asn Gly Lys
2285                2290                2295

Val Lys Val Phe Gln Gly Asn Gln Asp Ser Phe Thr Pro Val Val
2300                2305                2310

Asn Ser Leu Asp Pro Pro Leu Leu Thr Arg Tyr Leu Arg Ile His
2315                2320                2325

Pro Gln Ser Trp Val His Gln Ile Ala Leu Arg Met Glu Val Leu
2330                2335                2340

Gly Cys Glu Ala Gln Asp Leu Tyr Asp Lys Thr His Thr Cys Pro
2345                2350                2355

Pro Cys Pro Ala Pro Glu Leu Leu Gly Gly Pro Ser Val Phe Leu
2360                2365                2370

Phe Pro Pro Lys Pro Lys Asp Thr Leu Met Ile Ser Arg Thr Pro
2375                2380                2385

Glu Val Thr Cys Val Val Val Asp Val Ser His Glu Asp Pro Glu
2390                2395                2400

Val Lys Phe Asn Trp Tyr Val Asp Gly Val Glu Val His Asn Ala
2405                2410                2415

Lys Thr Lys Pro Arg Glu Glu Gln Tyr Asn Ser Thr Tyr Arg Val
2420                2425                2430

Val Ser Val Leu Thr Val Leu His Gln Asp Trp Leu Asn Gly Lys
2435                2440                2445

Glu Tyr Lys Cys Lys Val Ser Asn Lys Ala Leu Pro Ala Pro Ile
2450                2455                2460

Glu Lys Thr Ile Ser Lys Ala Lys Gly Gln Pro Arg Glu Pro Gln
2465                2470                2475

Val Tyr Thr Leu Pro Pro Ser Arg Asp Glu Leu Thr Lys Asn Gln
2480                2485                2490

Val Ser Leu Thr Cys Leu Val Lys Gly Phe Tyr Pro Ser Asp Ile
2495                2500                2505

Ala Val Glu Trp Glu Ser Asn Gly Gln Pro Glu Asn Asn Tyr Lys
2510                2515                2520

Thr Thr Pro Pro Val Leu Asp Ser Asp Gly Ser Phe Phe Leu Tyr
2525                2530                2535

Ser Lys Leu Thr Val Asp Lys Ser Arg Trp Gln Gln Gly Asn Val
2540                2545                2550
```

```
Phe Ser Cys Ser Val Met His Glu Ala Leu His Asn His Tyr Thr
    2555                2560                2565

Gln Lys Ser Leu Ser Leu Ser Pro Gly Lys
    2570                2575

<210> SEQ ID NO 7
<211> LENGTH: 11
<212> TYPE: PRT
<213> ORGANISM: Artificial Sequence
<220> FEATURE:
<223> OTHER INFORMATION: Albumin-binding Peptide Core

<400> SEQUENCE: 7

Asp Ile Cys Leu Pro Arg Trp Gly Cys Leu Trp
1               5                   10

<210> SEQ ID NO 8
<211> LENGTH: 32
<212> TYPE: PRT
<213> ORGANISM: Artificial Sequence
<220> FEATURE:
<223> OTHER INFORMATION: CTP peptide

<400> SEQUENCE: 8

Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 9
<211> LENGTH: 28
<212> TYPE: PRT
<213> ORGANISM: Artificial Sequence
<220> FEATURE:
<223> OTHER INFORMATION: CTP peptide

<400> SEQUENCE: 9

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 10
<211> LENGTH: 20
<212> TYPE: PRT
<213> ORGANISM: Artificial Sequence
<220> FEATURE:
<223> OTHER INFORMATION: PAS peptide

<400> SEQUENCE: 10

Ala Ser Pro Ala Ala Pro Ala Pro Ala Ser Pro Ala Ala Pro Ala Pro
1               5                   10                  15

Ser Ala Pro Ala
            20

<210> SEQ ID NO 11
<211> LENGTH: 20
<212> TYPE: PRT
<213> ORGANISM: Artificial Sequence
<220> FEATURE:
<223> OTHER INFORMATION: PAS peptide
```

```
<400> SEQUENCE: 11

Ala Ala Pro Ala Ser Pro Ala Pro Ala Ala Pro Ser Ala Pro Ala Pro
1               5                   10                  15

Ala Ala Pro Ser
            20

<210> SEQ ID NO 12
<211> LENGTH: 20
<212> TYPE: PRT
<213> ORGANISM: Artificial Sequence
<220> FEATURE:
<223> OTHER INFORMATION: PAS peptide

<400> SEQUENCE: 12

Ala Pro Ser Ser Pro Ser Pro Ser Ala Pro Ser Ser Pro Ser Pro Ala
1               5                   10                  15

Ser Pro Ser Ser
            20

<210> SEQ ID NO 13
<211> LENGTH: 19
<212> TYPE: PRT
<213> ORGANISM: Artificial Sequence
<220> FEATURE:
<223> OTHER INFORMATION: PAS peptide

<400> SEQUENCE: 13

Ala Pro Ser Ser Pro Ser Pro Ser Ala Pro Ser Ser Pro Ser Pro Ala
1               5                   10                  15

Ser Pro Ser

<210> SEQ ID NO 14
<211> LENGTH: 20
<212> TYPE: PRT
<213> ORGANISM: Artificial Sequence
<220> FEATURE:
<223> OTHER INFORMATION: PAS peptide

<400> SEQUENCE: 14

Ser Ser Pro Ser Ala Pro Ser Pro Ser Ser Pro Ala Ser Pro Ser Pro
1               5                   10                  15

Ser Ser Pro Ala
            20

<210> SEQ ID NO 15
<211> LENGTH: 24
<212> TYPE: PRT
<213> ORGANISM: Artificial Sequence
<220> FEATURE:
<223> OTHER INFORMATION: PAS peptide

<400> SEQUENCE: 15

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 16
<211> LENGTH: 20
<212> TYPE: PRT
<213> ORGANISM: Artificial Sequence
<220> FEATURE:
<223> OTHER INFORMATION: PAS peptide
```

```
<400> SEQUENCE: 16

Ala Ser Ala Ala Ala Pro Ala Ala Ala Ser Ala Ala Ala Ser Ala Pro
1               5                   10                  15

Ser Ala Ala Ala
            20

<210> SEQ ID NO 17
<211> LENGTH: 21
<212> TYPE: PRT
<213> ORGANISM: Artificial Sequence
<220> FEATURE:
<223> OTHER INFORMATION: fragment of Factor VIII B domain

<400> SEQUENCE: 17

Ser Phe Ser Gln Asn Ser Arg His Pro Ser Gln Asn Pro Pro Val Leu
1               5                   10                  15

Lys Arg His Gln Arg
            20

<210> SEQ ID NO 18
<211> LENGTH: 6
<212> TYPE: PRT
<213> ORGANISM: Artificial Sequence
<220> FEATURE:
<223> OTHER INFORMATION: His tag

<400> SEQUENCE: 18

His His His His His His
1               5
```